US010400263B2

(12) United States Patent
Sinclair et al.

(10) Patent No.: US 10,400,263 B2
(45) Date of Patent: Sep. 3, 2019

(54) TRIPEPTIDE RHODAMINE COMPOUND

(71) Applicant: Kingston Uninversity Higher Education Corporation, Kingston Upon Thames (GB)

(72) Inventors: Alex Sinclair, Mitcham (GB); Mark Fielder, Ripley (GB); Adam Le Gresley, Aldershot (GB)

(73) Assignee: Kingston University Higher Education Corporation, Surrey (GB)

( * ) Notice: Subject to any disclaimer, the term of this patent is extended or adjusted under 35 U.S.C. 154(b) by 0 days.

(21) Appl. No.: 14/415,457

(22) PCT Filed: Jul. 19, 2013

(86) PCT No.: PCT/GB2013/051947
§ 371 (c)(1),
(2) Date: Jan. 16, 2015

(87) PCT Pub. No.: WO2014/013272
PCT Pub. Date: Jan. 23, 2014

(65) Prior Publication Data
US 2015/0240283 A1 Aug. 27, 2015

(30) Foreign Application Priority Data

Jul. 19, 2012 (GB) .................................. 1212853.4
Mar. 27, 2013 (GB) .................................. 1305634.6

(51) Int. Cl.
*C12Q 1/14* (2006.01)
*A61K 49/00* (2006.01)
*C07D 493/10* (2006.01)
*C09B 11/24* (2006.01)
*C12Q 1/37* (2006.01)
*C07K 5/083* (2006.01)
*G01N 33/542* (2006.01)
*C07K 5/09* (2006.01)

(52) U.S. Cl.
CPC ............ *C12Q 1/14* (2013.01); *A61K 49/0017* (2013.01); *C07D 493/10* (2013.01); *C07K 5/0808* (2013.01); *C07K 5/0817* (2013.01); *C09B 11/24* (2013.01); *C12Q 1/37* (2013.01); *G01N 33/542* (2013.01); *G01N 2333/31* (2013.01); *G01N 2333/952* (2013.01)

(58) Field of Classification Search
CPC .......... C12Q 1/14; C12Q 1/37; C07K 5/0808; C07K 5/0817; A61K 49/0017; C07D 493/10; C09B 11/24; G01N 33/542
See application file for complete search history.

(56) References Cited

U.S. PATENT DOCUMENTS

| 4,557,862 A | 12/1985 | Mangel et al. |
| 4,640,893 A * | 2/1987 | Mangel ................ C07D 493/10 435/23 |
| 2010/0047170 A1* | 2/2010 | Denmeade ....... A61K 47/48338 424/9.1 |

FOREIGN PATENT DOCUMENTS

| EP | 2 036 897 A1 | 3/2009 |
| WO | 1999/18856 | 4/1999 |
| WO | 2003/099780 A2 | 12/2003 |

OTHER PUBLICATIONS

Leytus et al. "New class of sensitive and selective fluorogenic substrates for serine proteinases" (1983), vol. 215: 253-260.*
Boonacker et al. (2003) "Fluorogenic Substrate [Ala-Pro] 2-Cresyl Violet But Not Ala-Pro-Rhodamine 110 Is Cleaved Specifically by DPPIV Activity: A Study in Living Jurkat Cells and CD26/DPPIV-transfected Jurkat Cells," The Journal of Histochemistry and Cytochemistry 51(7):959-968.
Bures et al. (2004) "High-Performance Liquid Chromatography-Based Protease Detection at the Picogram Level," Analytical Biochemistry 326(2):276-277.
CAS Registry No. 254451-57-5. (2004).
CAS Registry No. 757928-93-1. (2000).
Holliday et al. (1999) "Rapid Identification of *Staphylococcus aureus* by Using Fluorescent Staphylocoagulase Assays," J. Clin. Microbiol. 37(4):1190-1192.
Mitchell et al. (1985) "Novel Rhodamine Tripeptide Substrate for Manual and Automated Colorimetric Prothrombin Time Test," Thromb. Res. 40(3):339-349.
Molecular Probes et al. (2006) "Rhodamine 110-Based Proteinase Substrates," Molecular Probes Inc. Manuals and Protocols No. 06501.
Sinclair et al. (Mar. 18, 2013) "Development of an in situ Culture-Free Screening Test for the Rapid Detection of *Staphylococcus aureus* within Healthcare Environments," Organic and Molecular Biology 11:3307-3313.
Search Report, dated Oct. 10, 2013, corresponding to International Application No. PCT/GB2013/051947 (filed Jul. 19, 2013), parent of the present application, 5 pp.
European First Office Action, dated Jul. 5, 2016, in European Patent Application No. EP 13740356.4, a related application, 5 pp.
Palomo, Jose (Jul. 2014), "Solid-phase peptide synthesis: an overview focused on the preparation of biologically relevant peptides," RSC Advances 4:32658.

(Continued)

*Primary Examiner* — Louise W Humphrey
*Assistant Examiner* — Teresa E Knight
(74) *Attorney, Agent, or Firm* — Leydig, Voit & Mayer, Ltd.

(57) ABSTRACT

The present invention concerns rhodamine based fluorescent probes which have use in detecting coagulase-producing bacterial strains. In particular, wherein the bacterial strain is MRSA or MSSA.

8 Claims, 34 Drawing Sheets

(56) References Cited

OTHER PUBLICATIONS

Morita et al., (1977), "New Fluorogenic Substrates for α-Thrombin, Factor Xa, Kallikreins, and Urokinase," J. Biochem. 82(5):1495-1498 (Abstract Only).
Leytus et al., 1983, "*Rhodamine-based compounds as fluorogenic substrates for serine proteinases*," Biochem. J., 209:299-307.

* cited by examiner

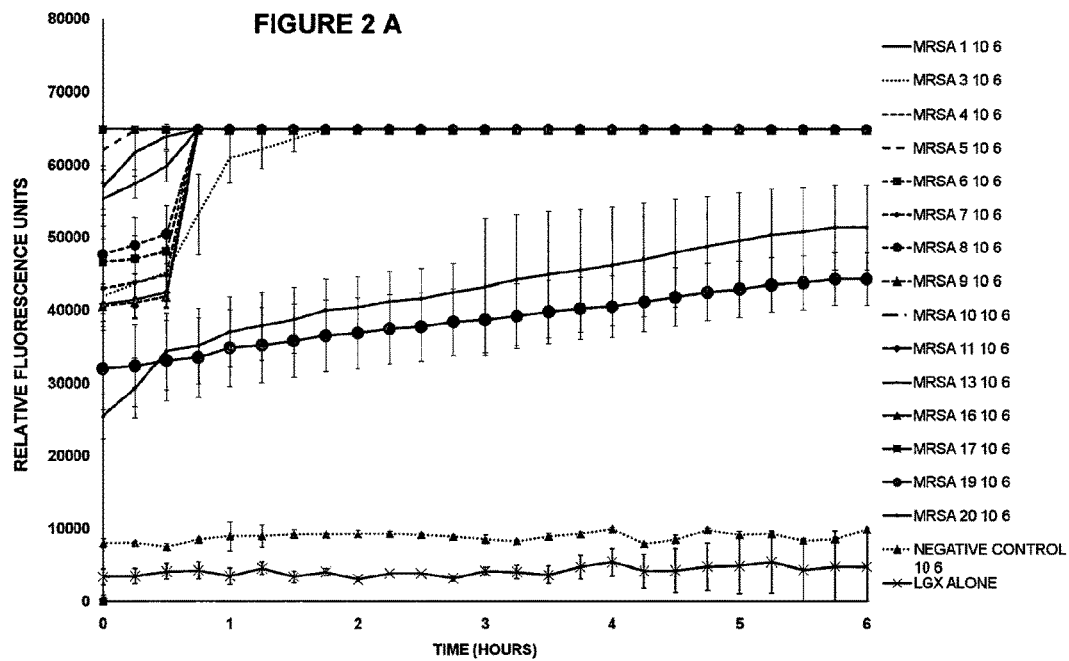
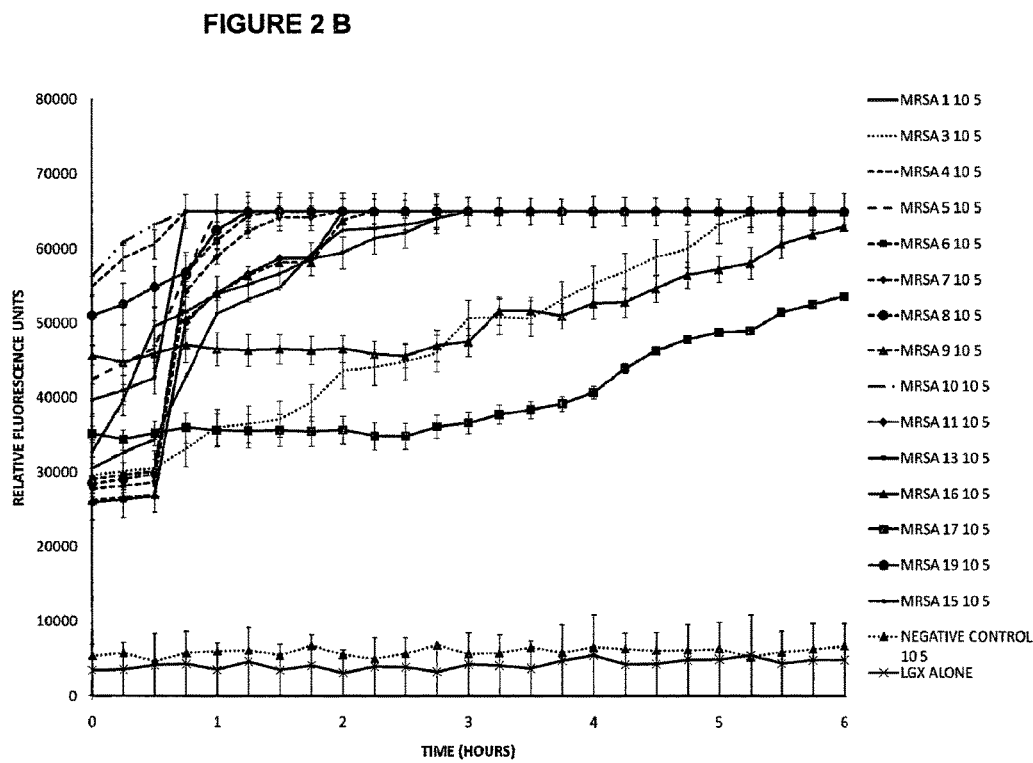

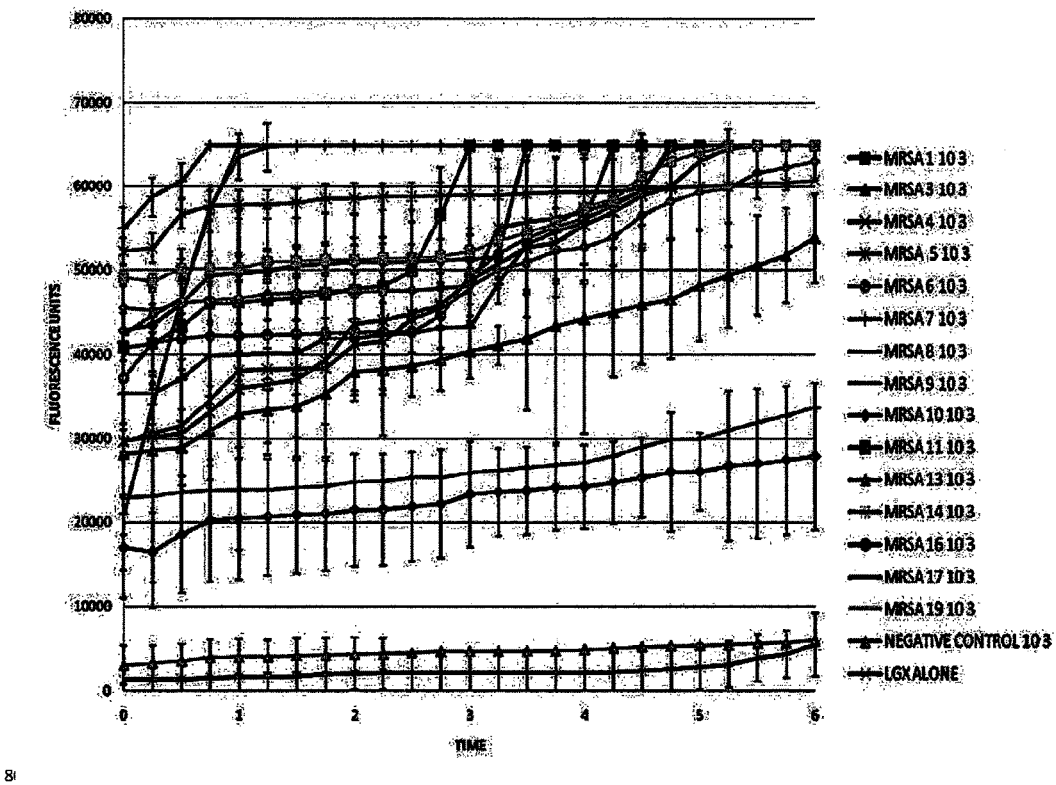
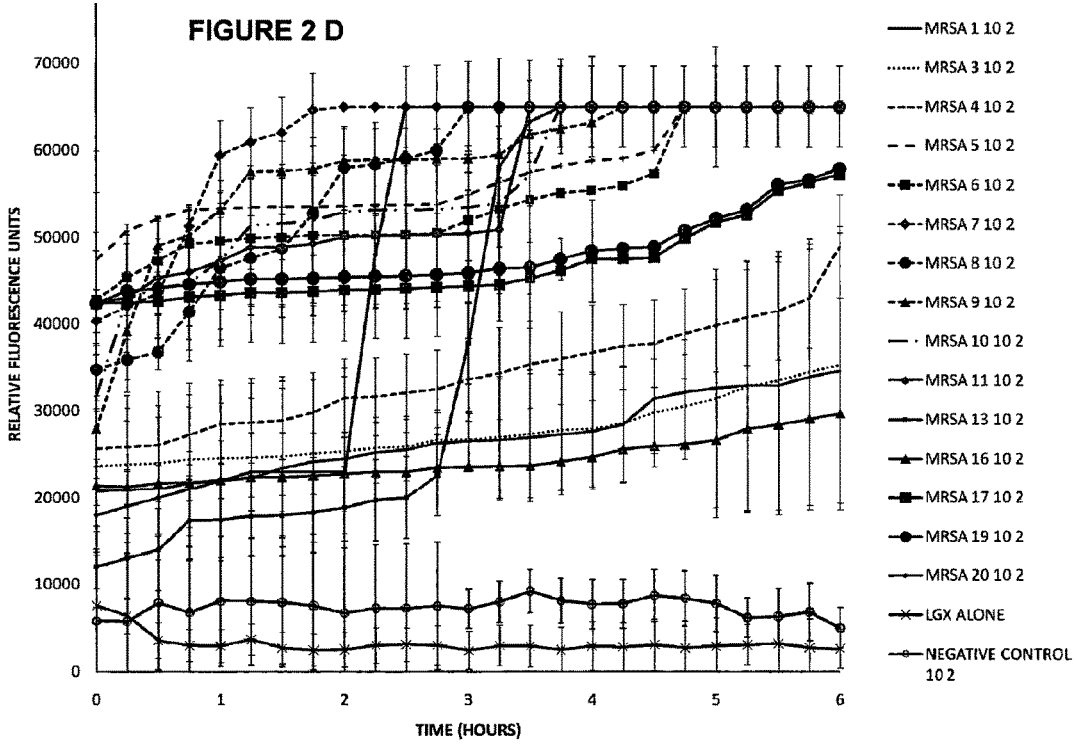

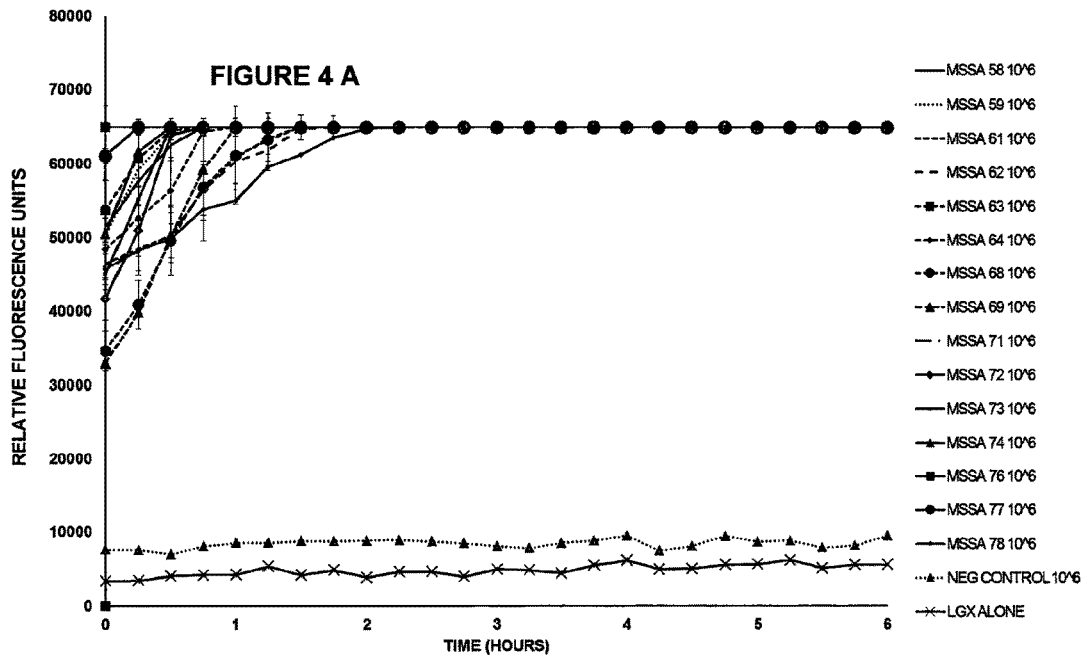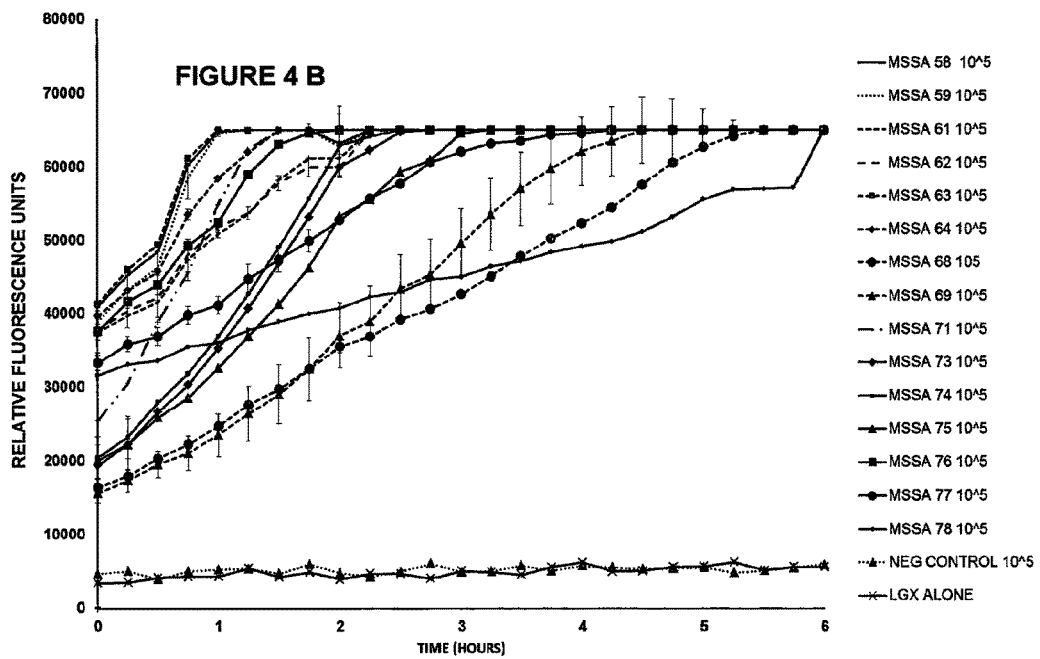

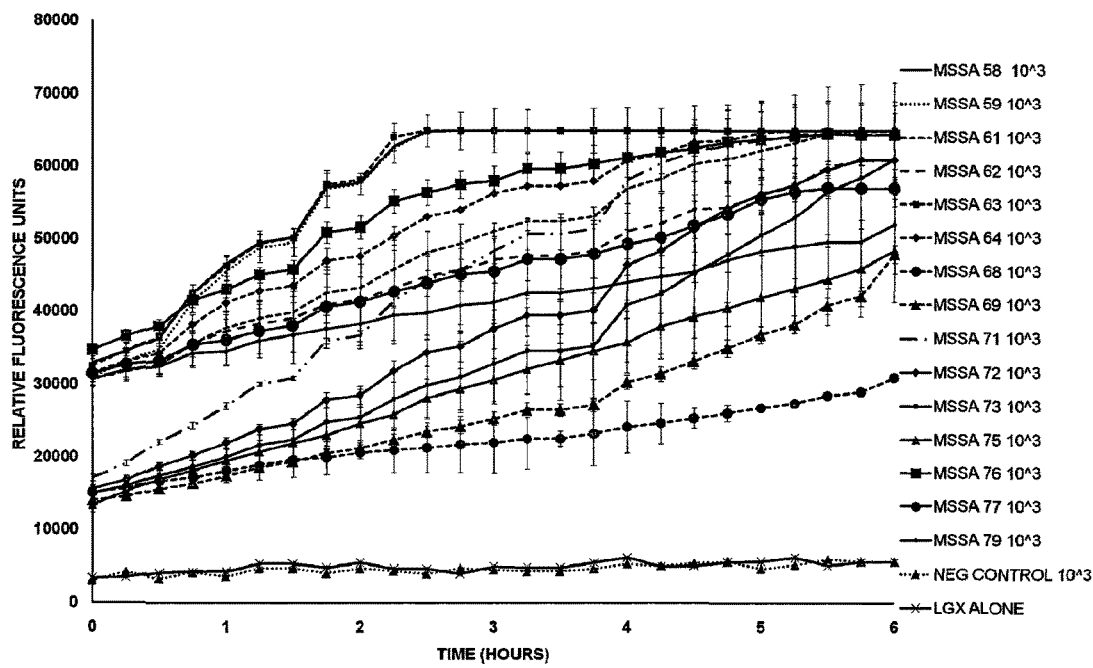
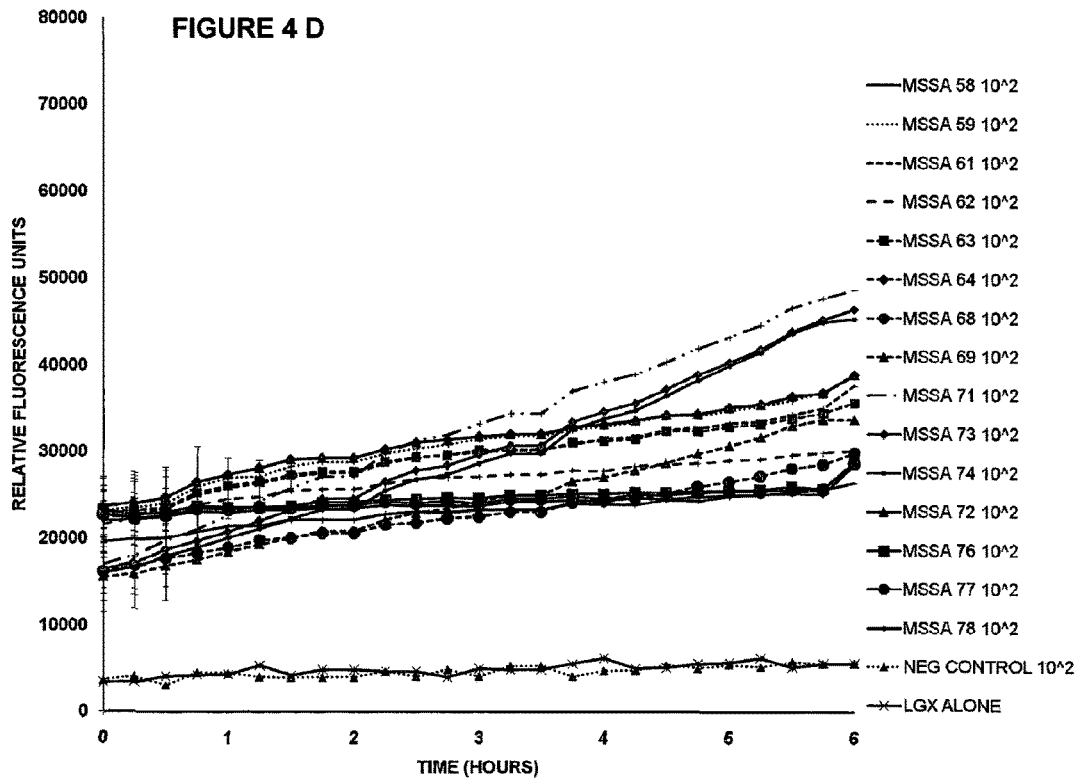

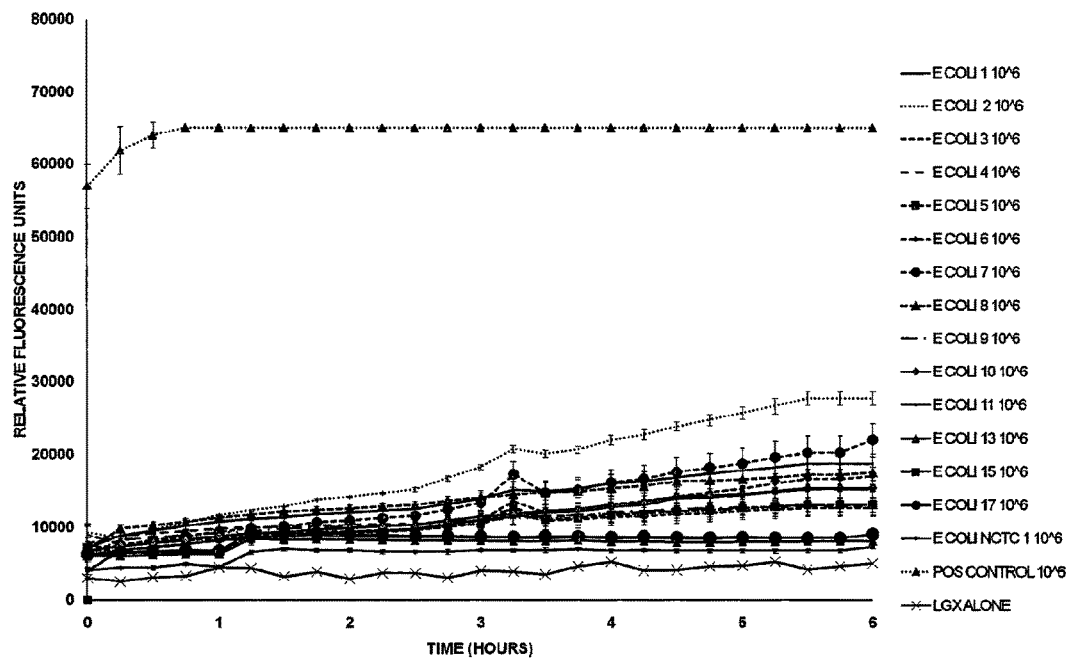
FIGURE 6 A (1)
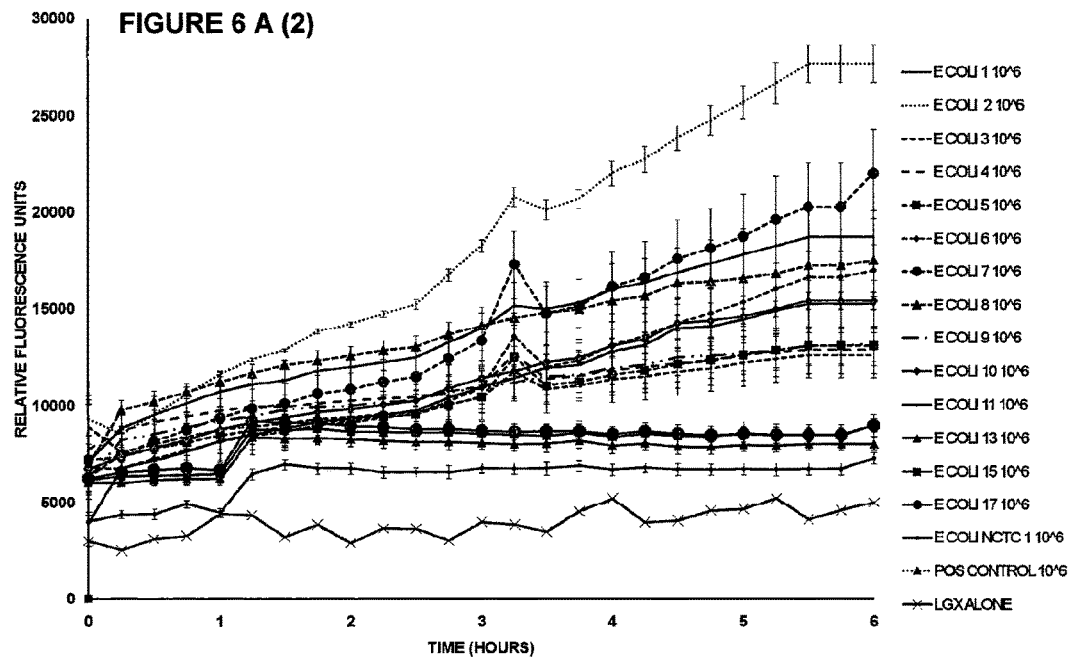
FIGURE 6 A (2)

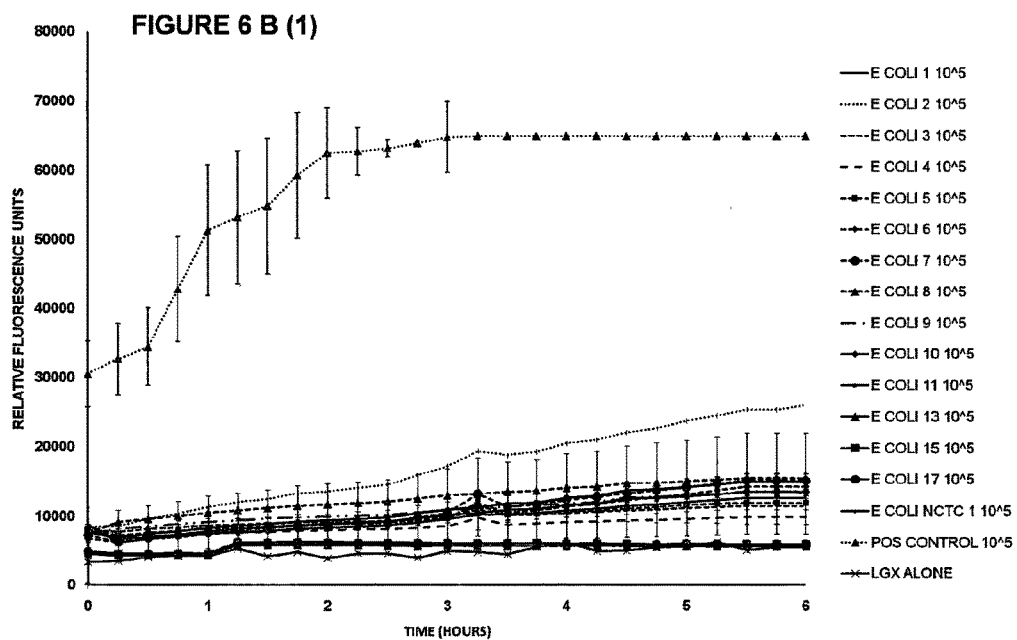
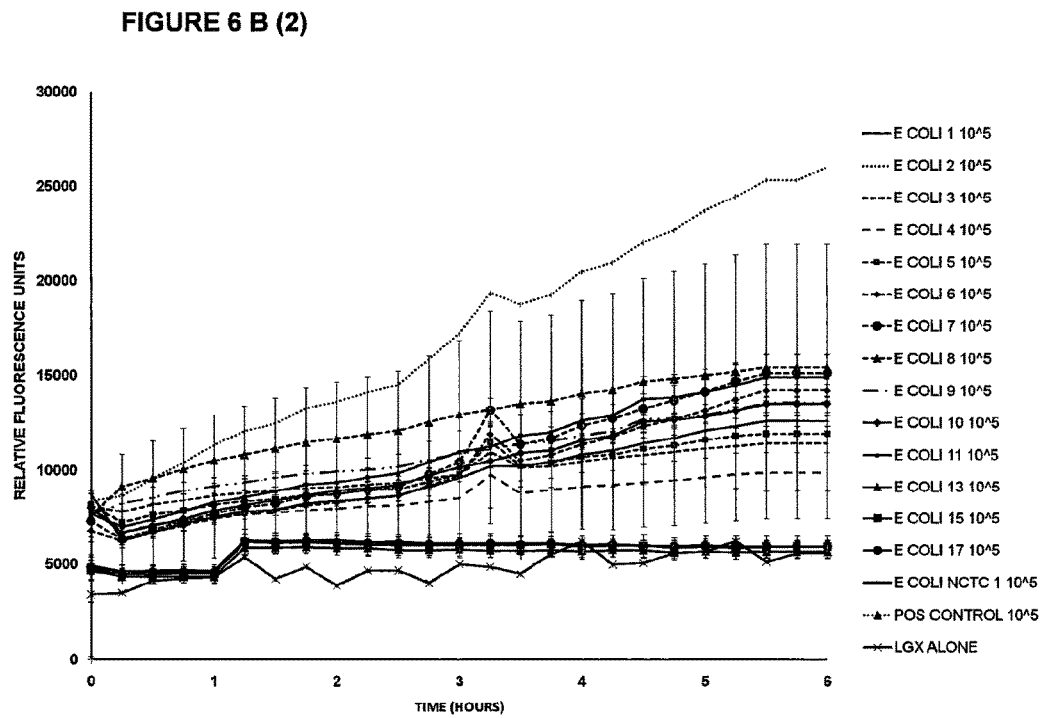

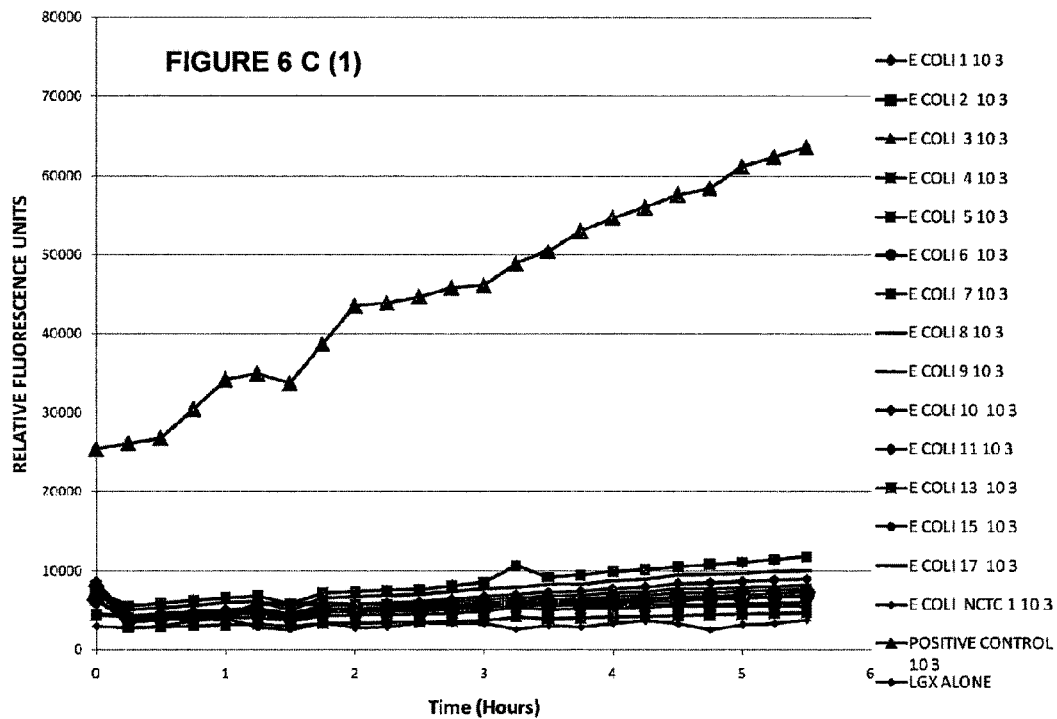
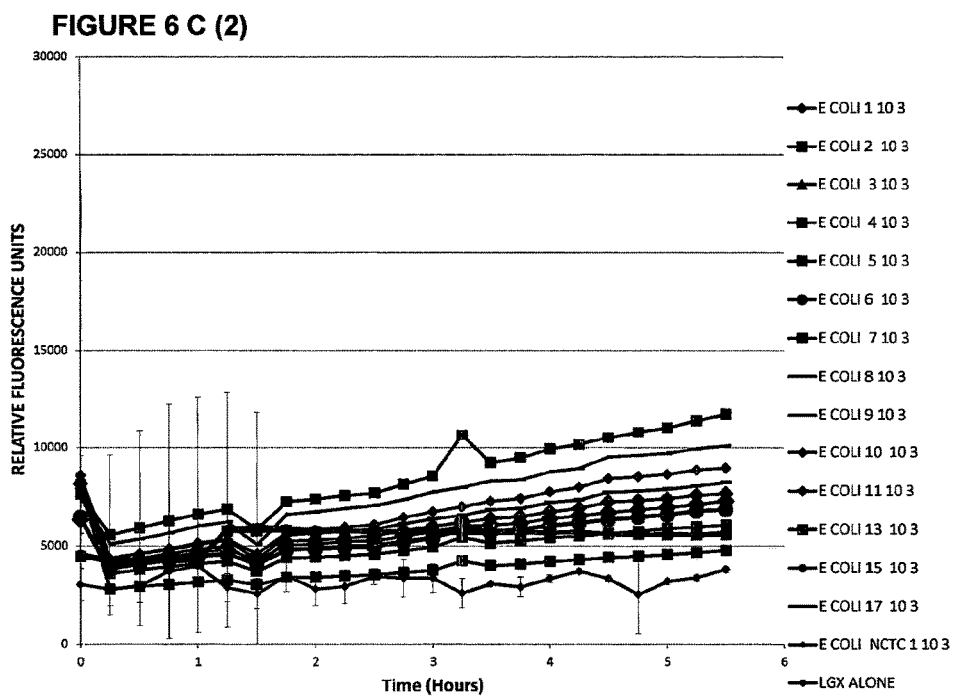

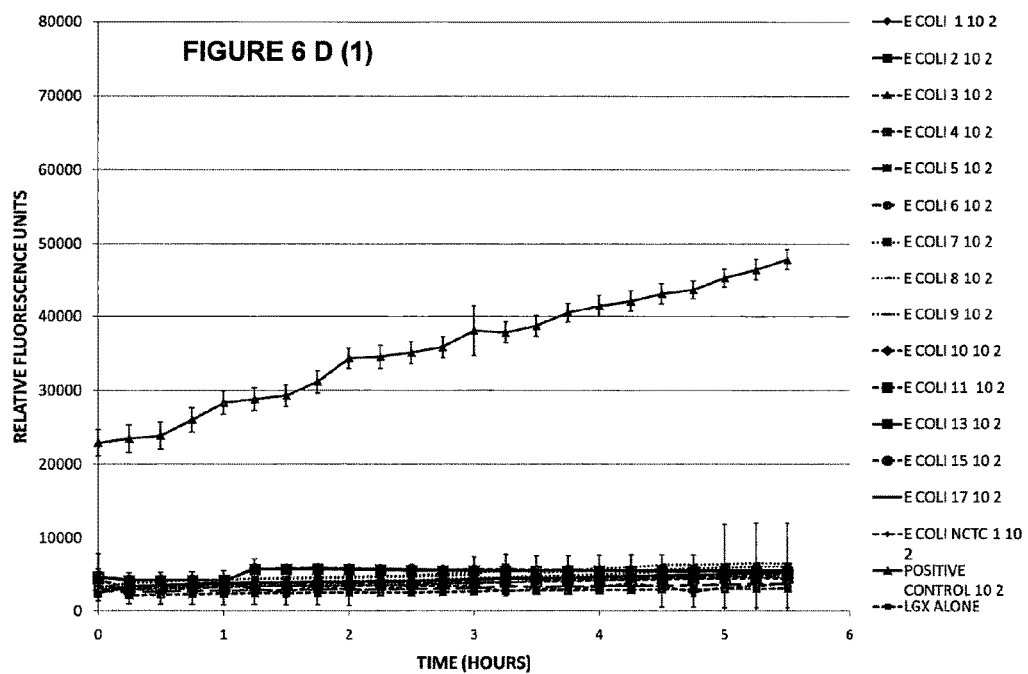
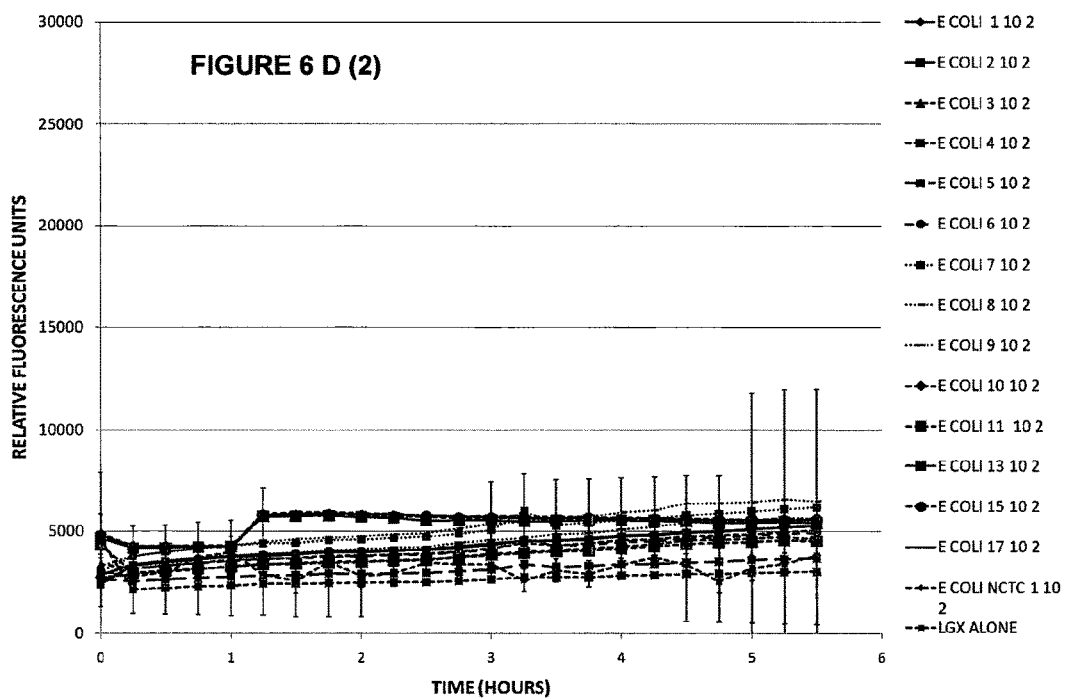

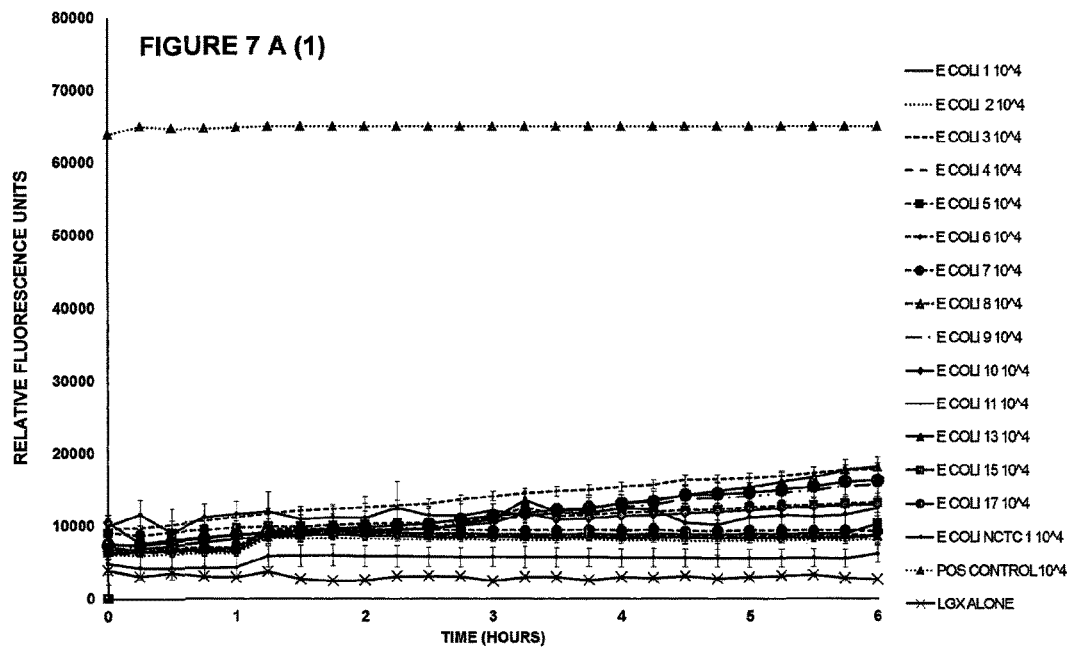
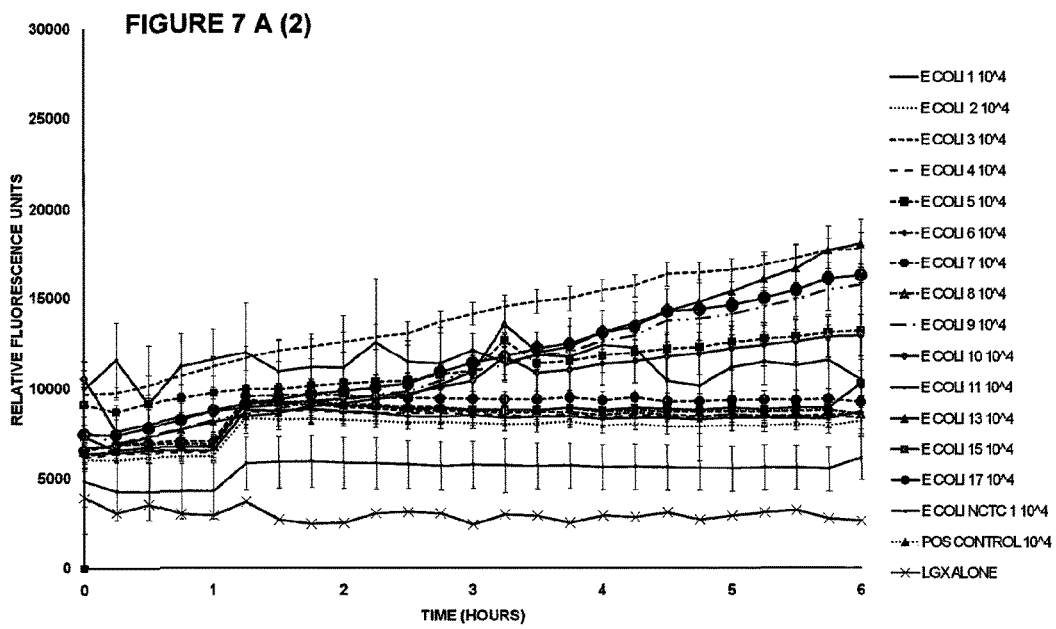

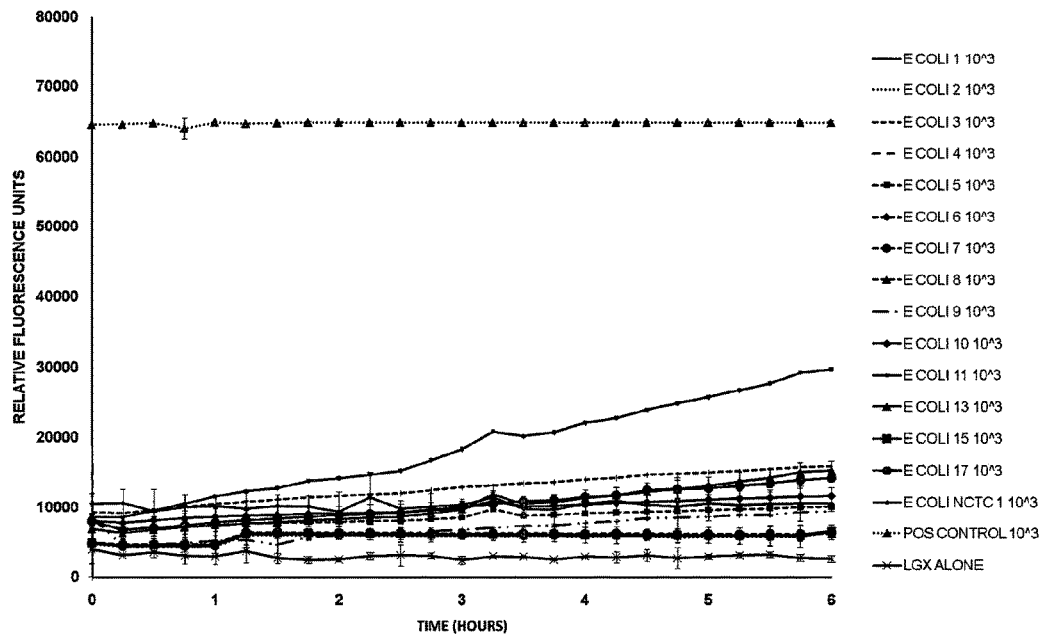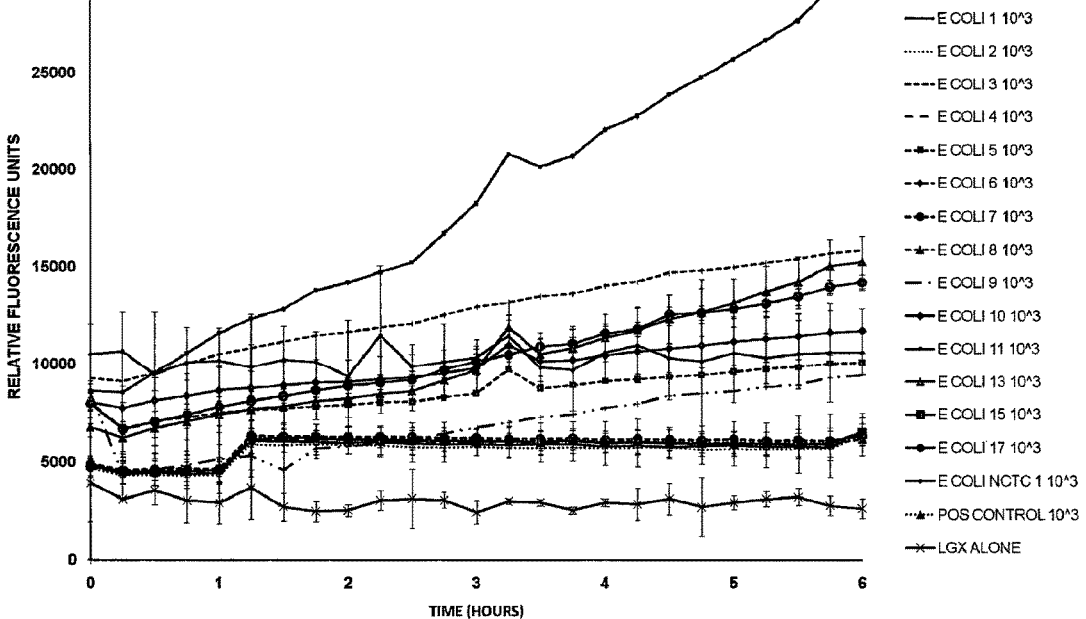

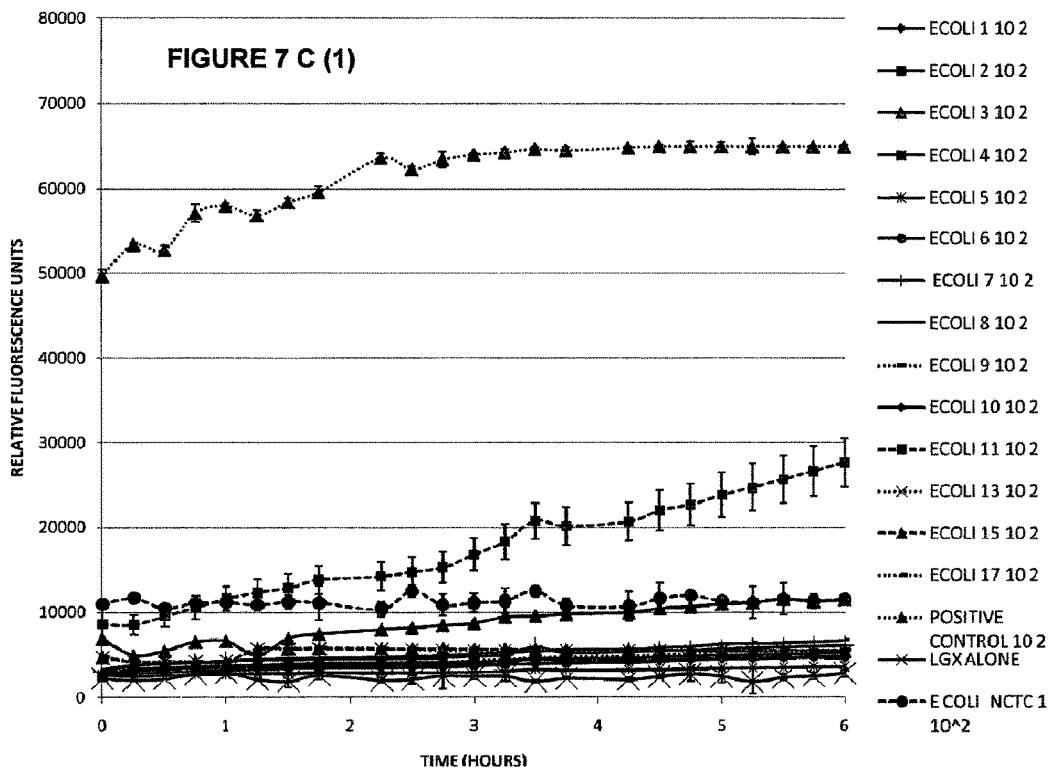
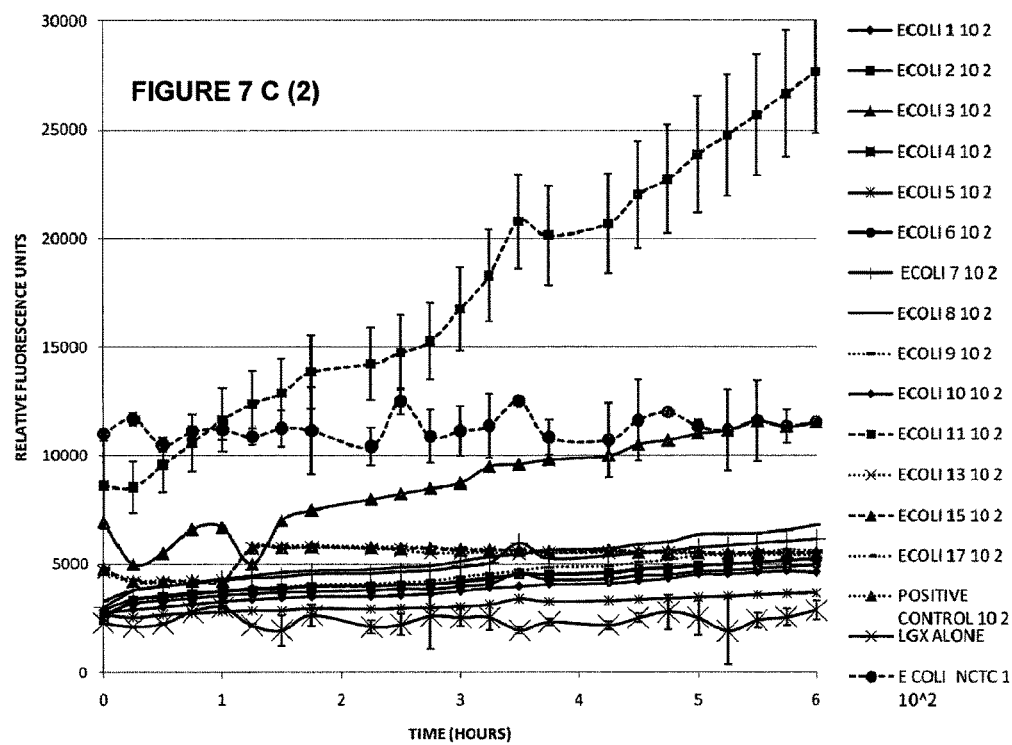

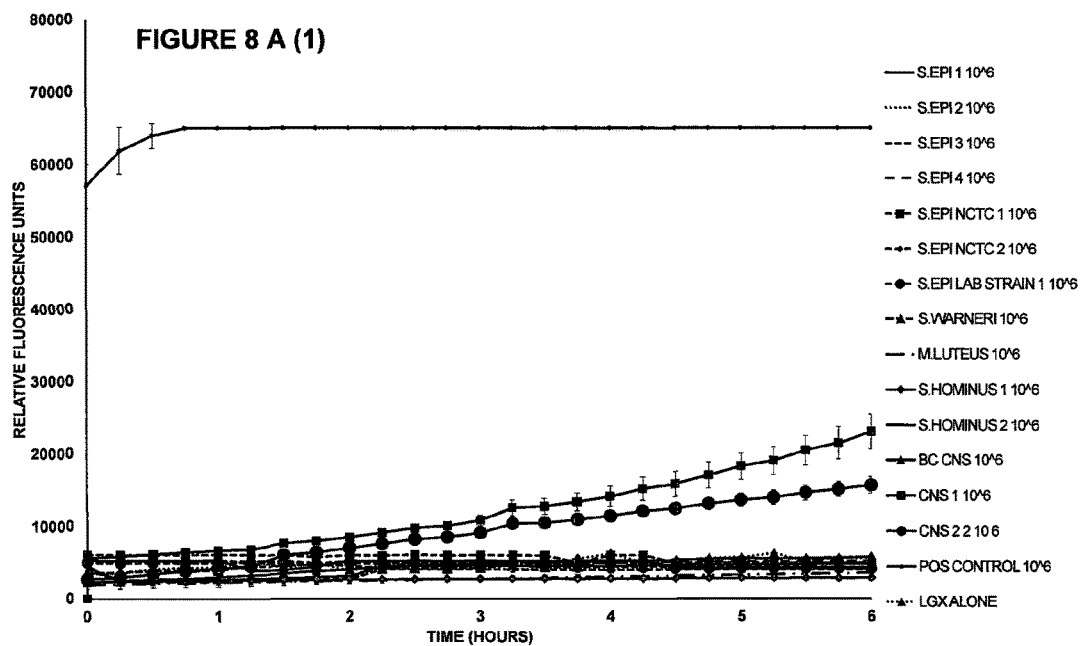
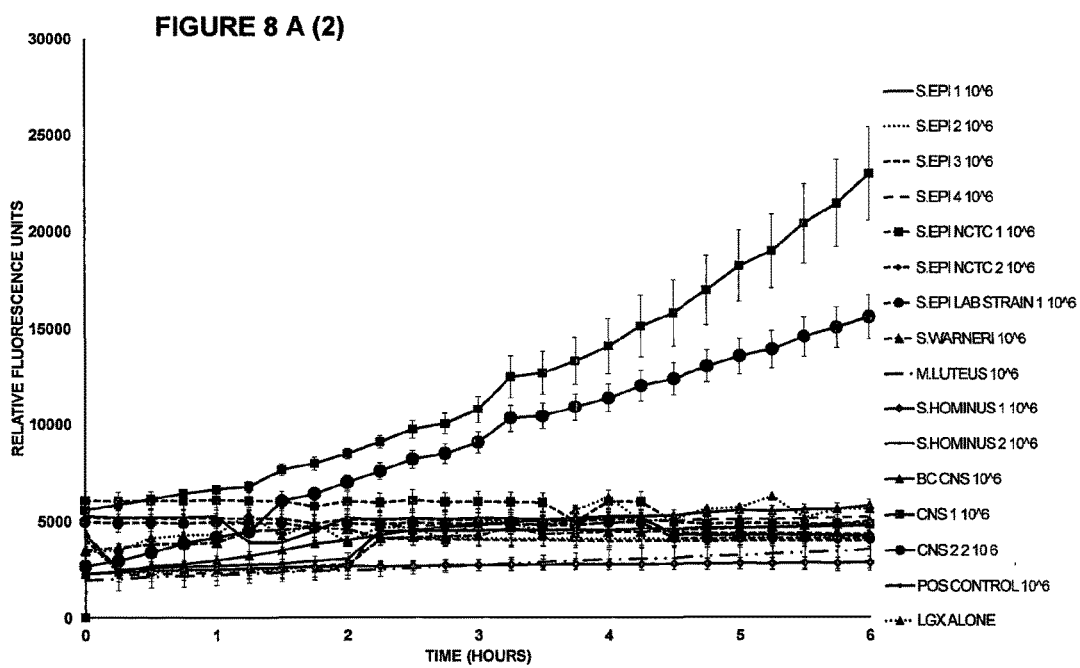

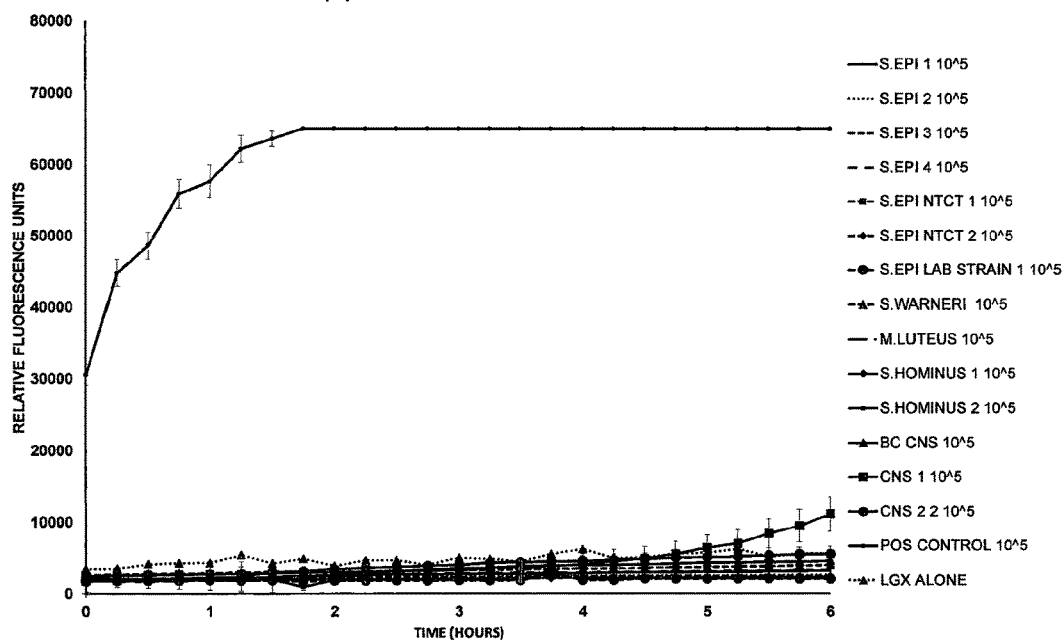
FIGURE 8 B (1)
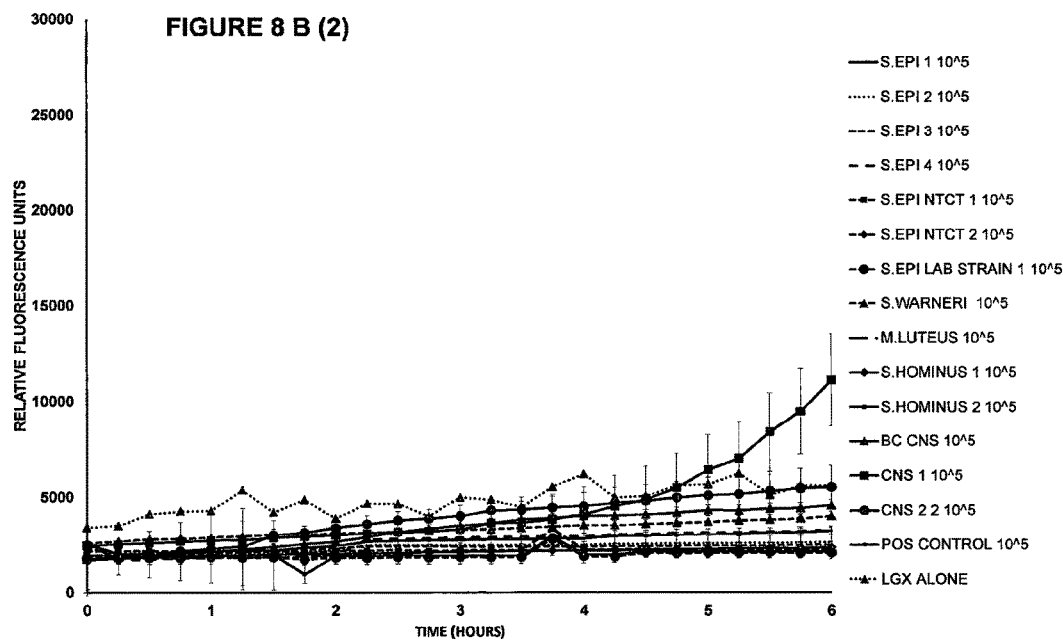
FIGURE 8 B (2)

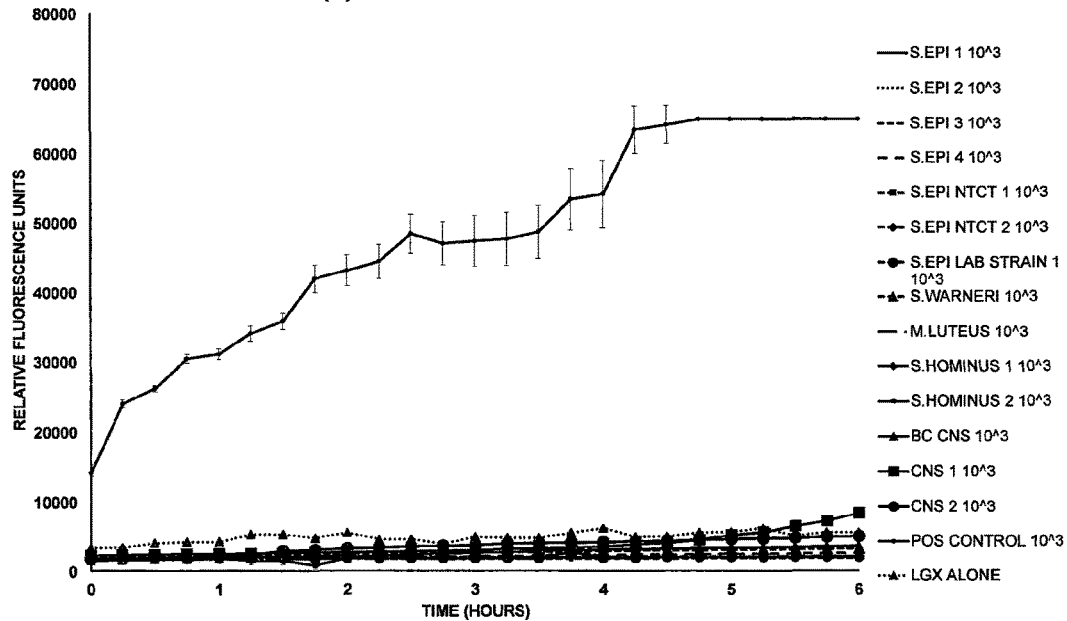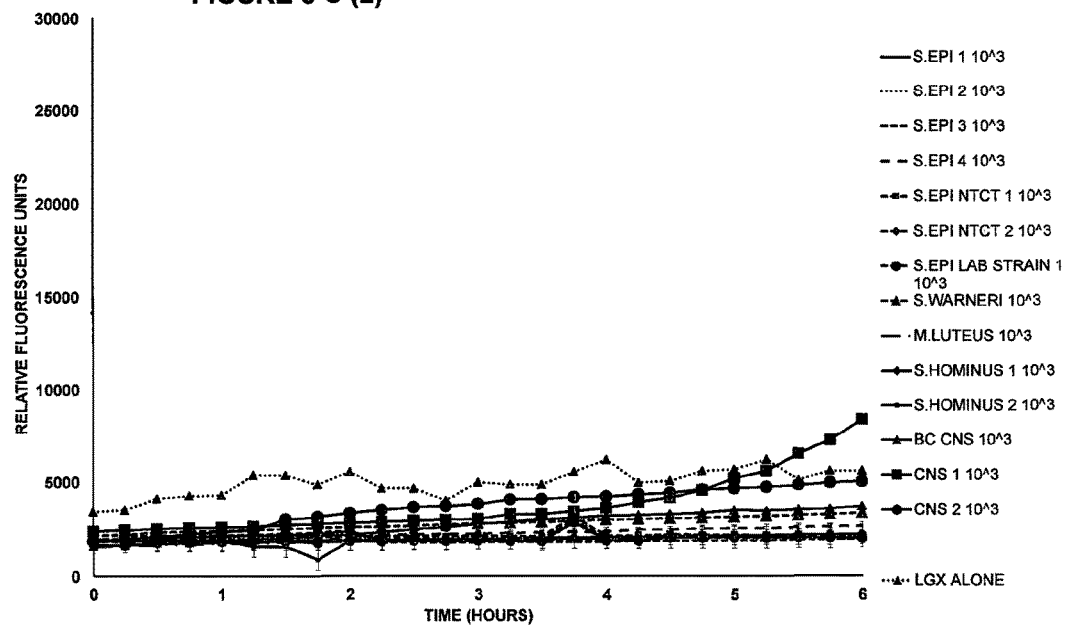

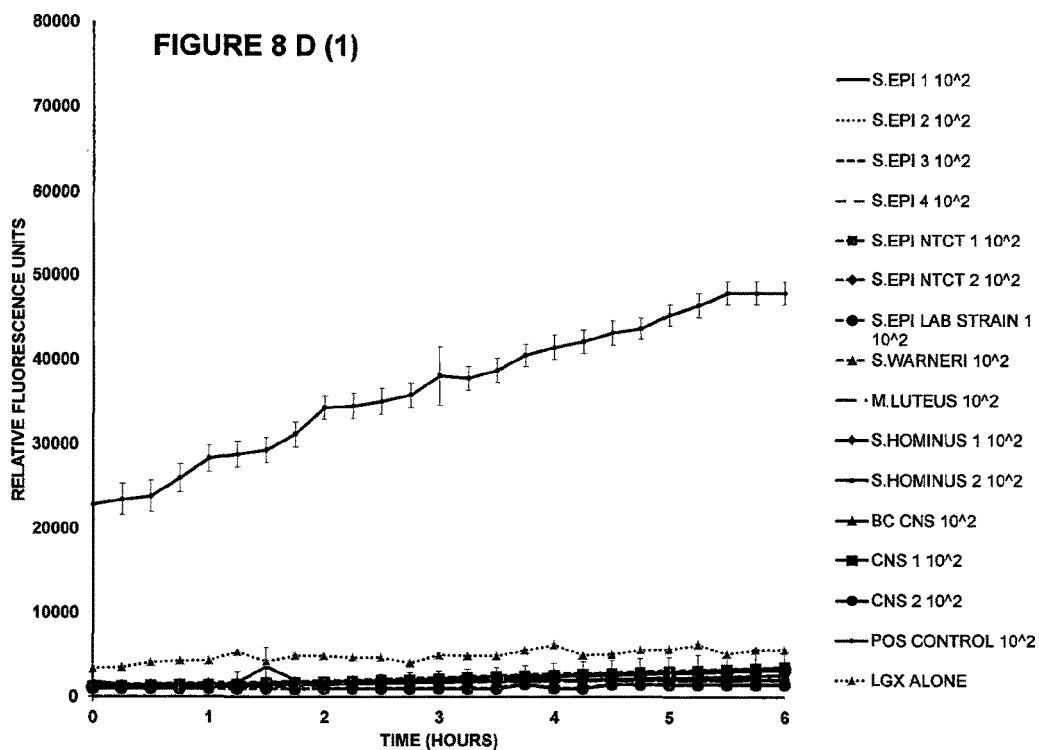
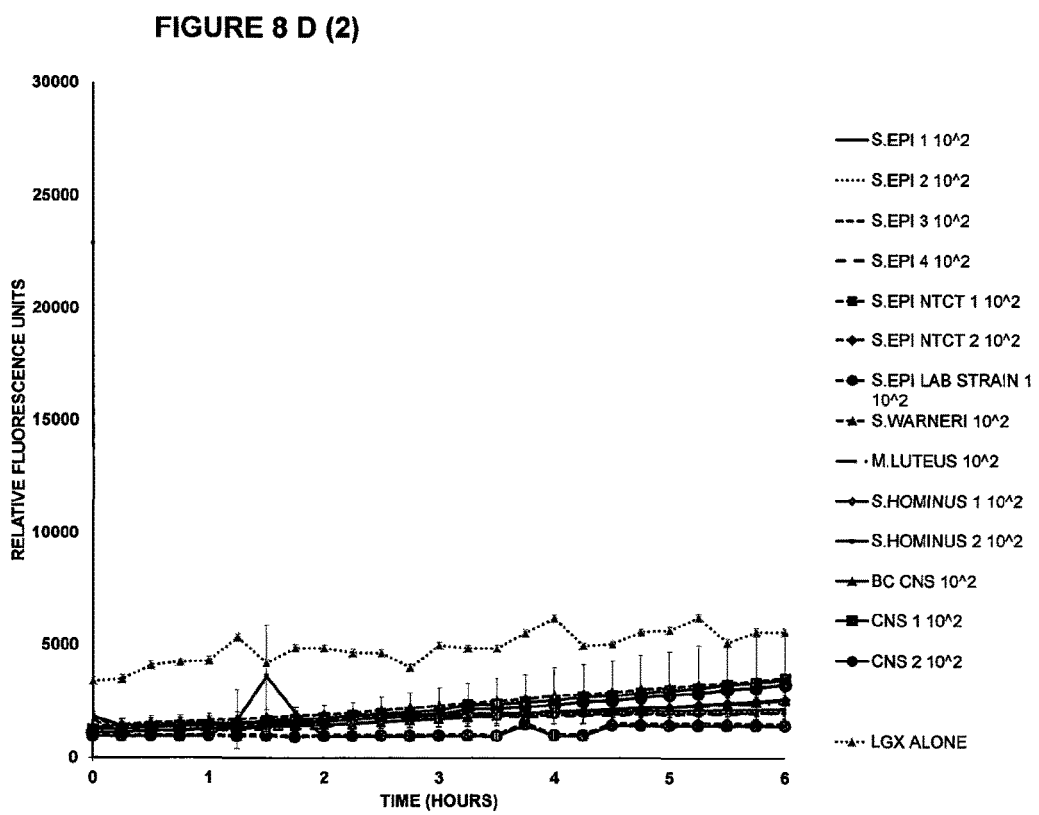

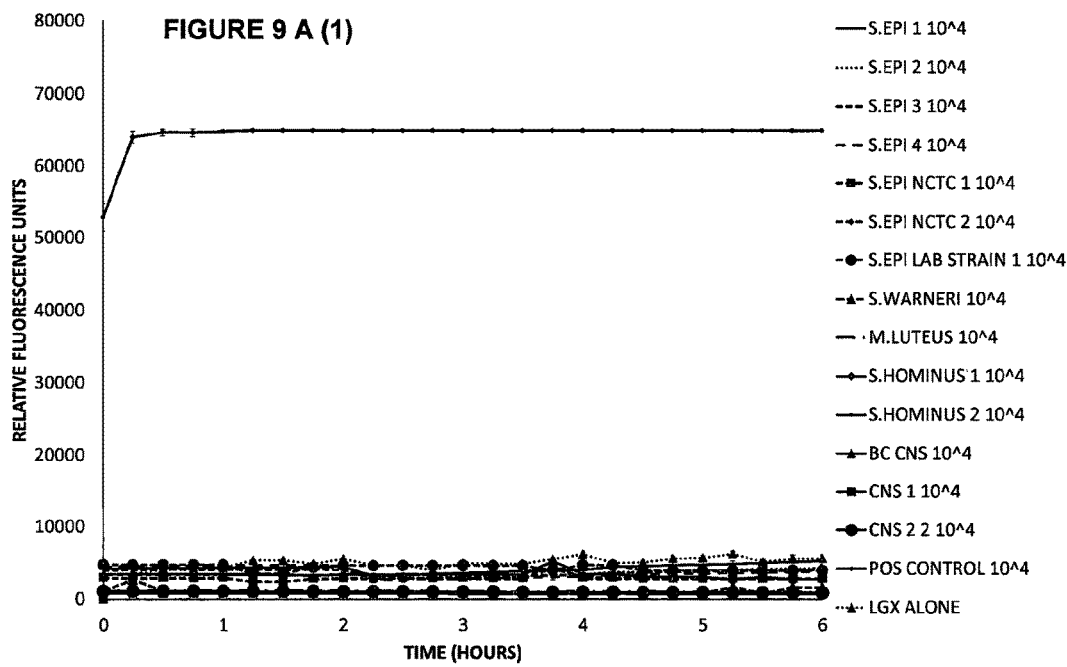
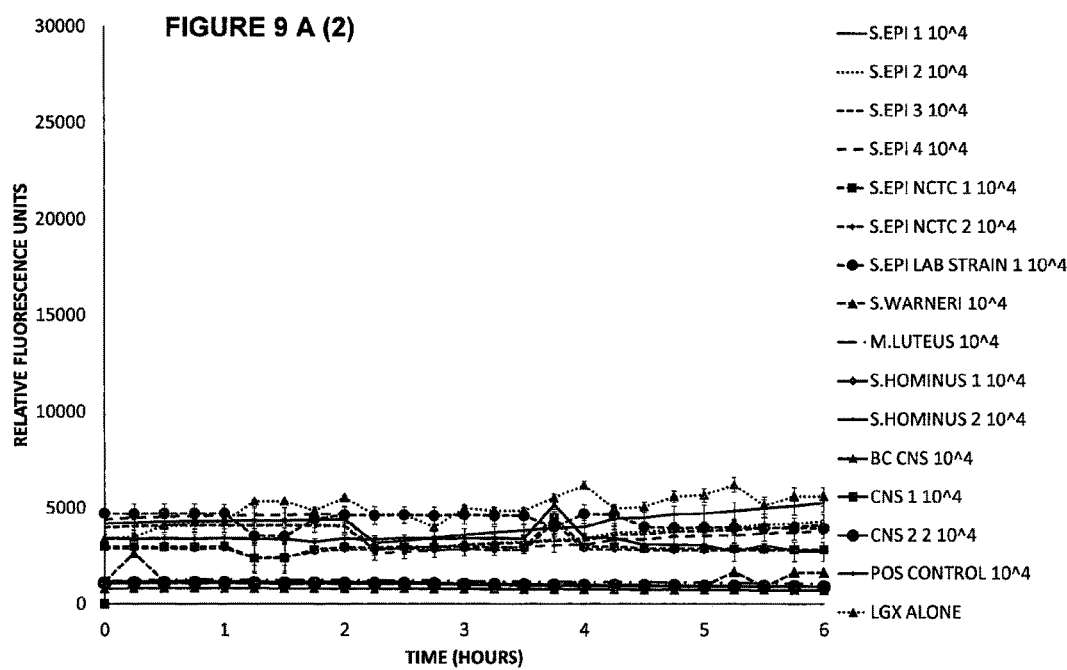

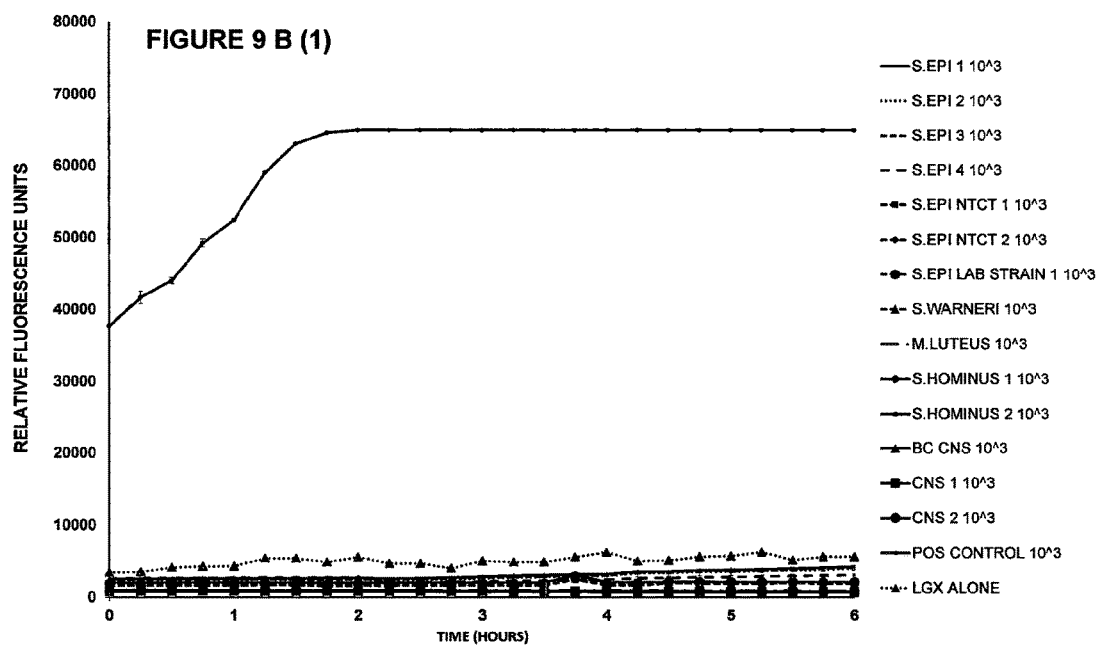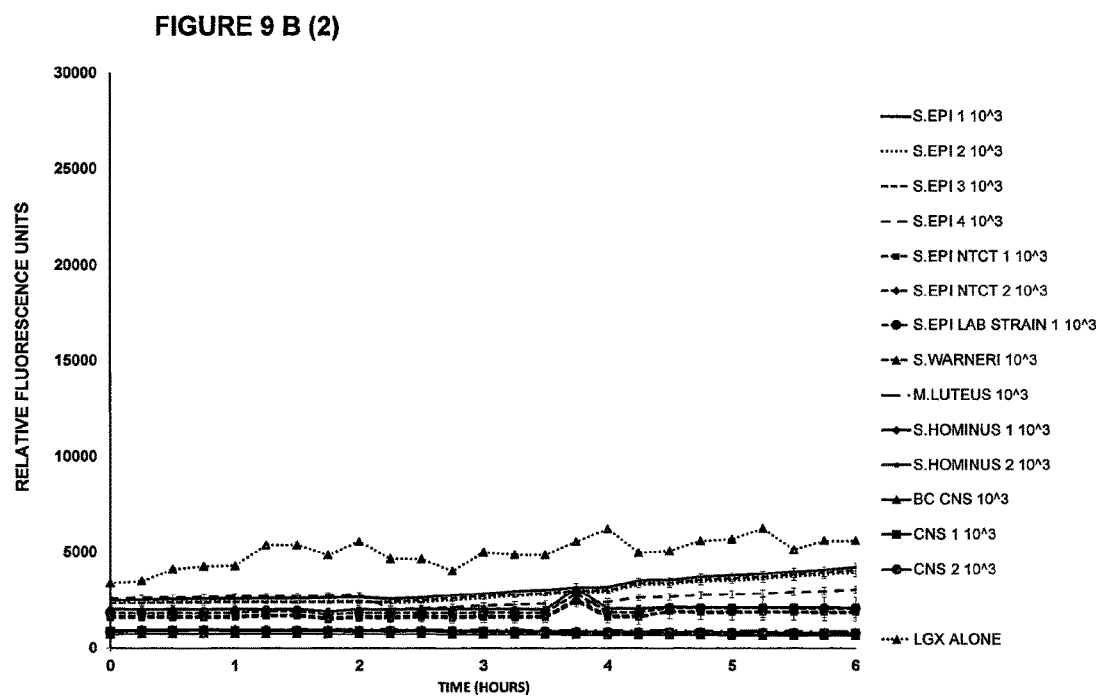

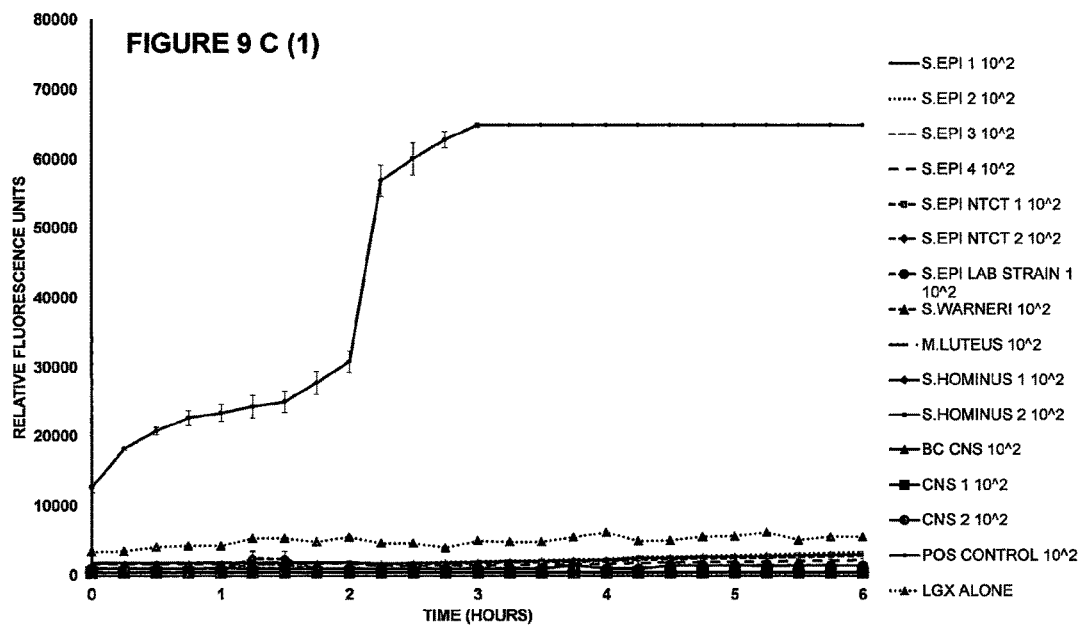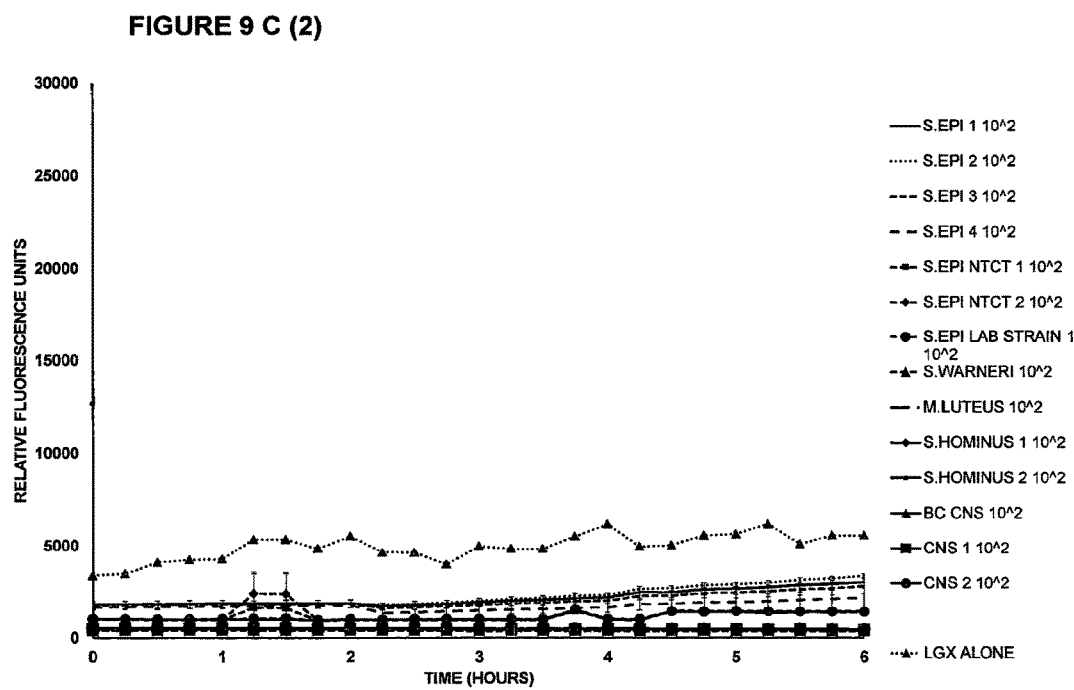

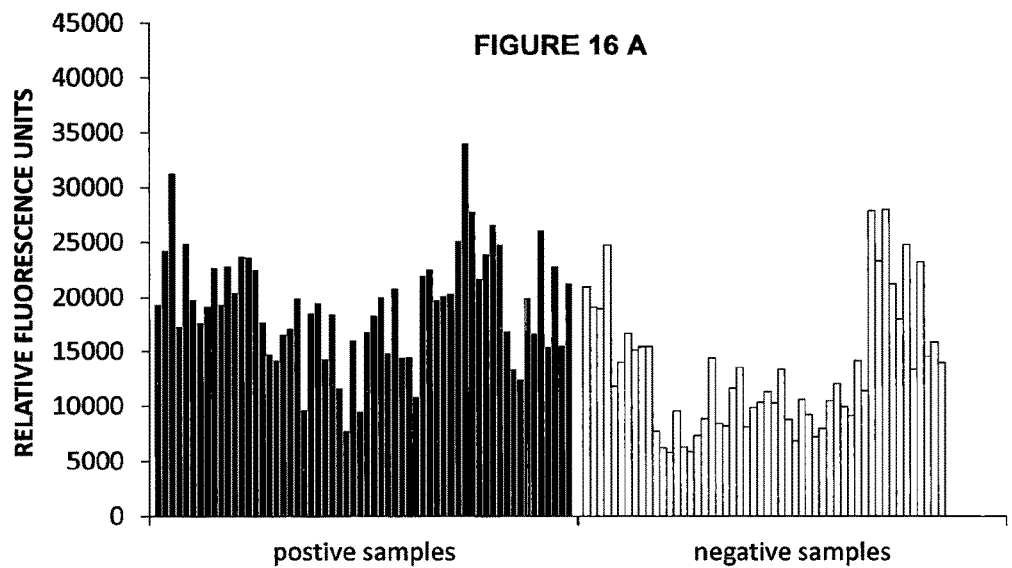
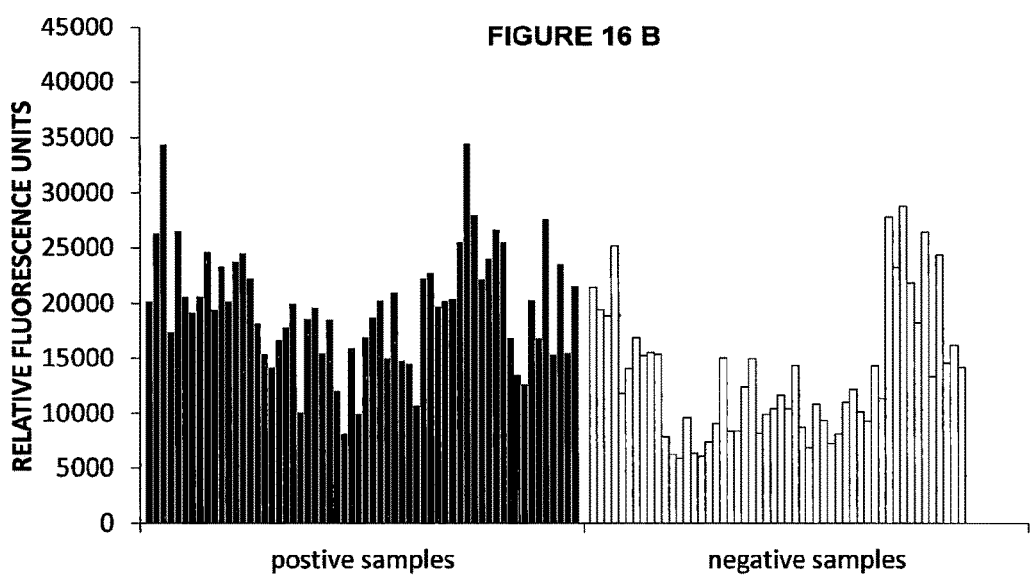

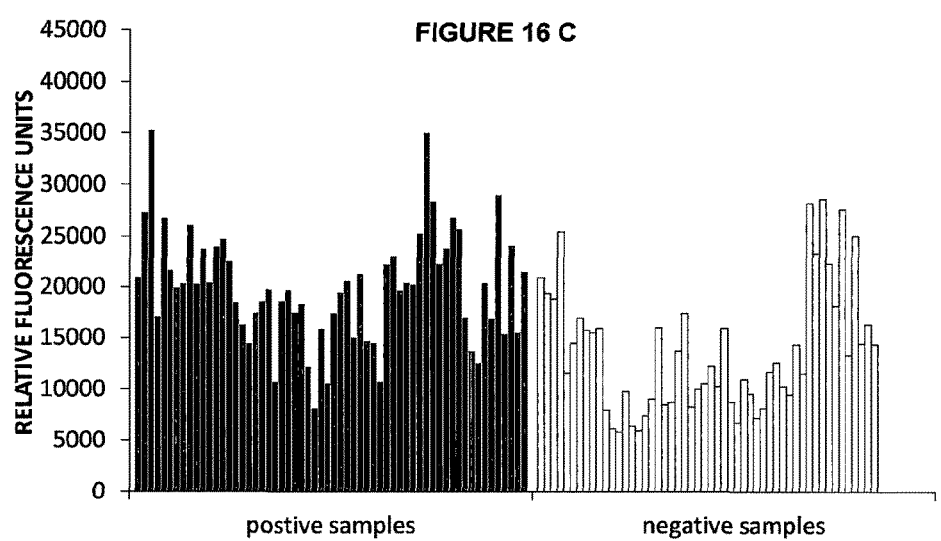

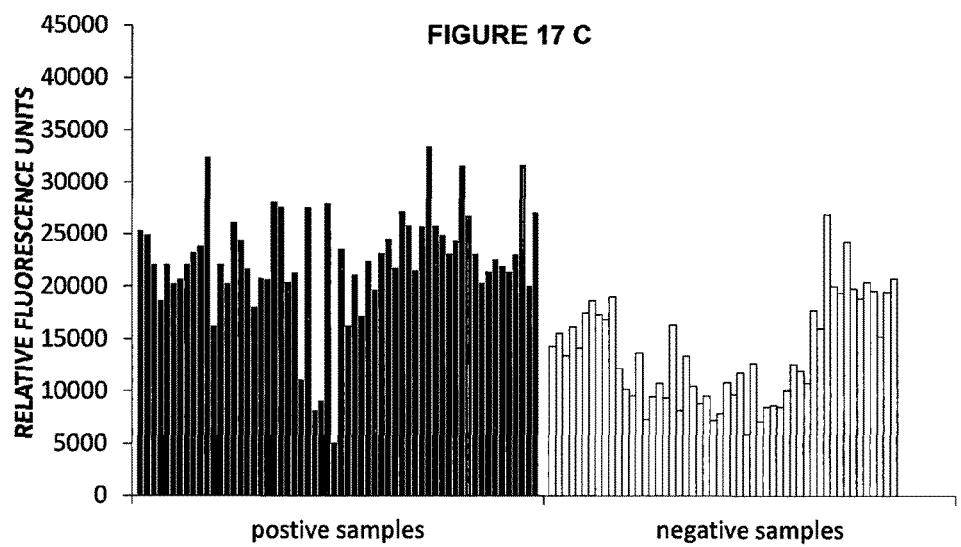

TRIPEPTIDE RHODAMINE COMPOUND

CROSS-REFERENCE TO RELATED APPLICATIONS

This application is a U.S. National Stage Application filed under 35 U.S.C. § 371 of International Application No. PCT/GB2013/051947, filed Jul. 19, 2013, which claims the benefit of Great Britain Application No. GB 1305634.6, filed Mar. 27, 2013, and Great Britain Application No. GB 1212853.4, filed Jul. 19, 2012. All three of these applications are hereby incorporated by reference in their entireties.

THE FIELD OF THE INVENTION

The present invention concerns compounds which have use in detecting coagulase-producing bacterial strains. In particular, wherein the bacterial strain is MRSA or MSSA.

BACKGROUND TO THE INVENTION

Currently, the treatment of every case of methicillin resistant *Staphylococcus aureus* (MRSA) infection costs the UK National Health Service £9000 (Wendin R: The economics of patient safety: can you afford not to be safe, Marsh Europe S.A. Report commissioned by The Royal College of Physicians, London; 2008), which amounts to more than £45 m per year.

Although there has been investment of £50 m to deep clean the hospitals, it has been reported that there has been a small increase in the number of infection cases. This may be due to the fact that there are particular target areas in a hospital environment where reoccurrence of MRSA and MSSA (methicillin susceptible *Staphylococcus aureus*) infections are more likely.

In addition, MRSA related deaths came to 1200 in 2008 (Office for National Statistics. Health indicators. *Health Stat Q.* 2008; 37:7.) and whilst this represents a drop when compared to previous years, a disproportionate number are nosocomial and demand the use of expensive antibiotics to combat. Despite this apparent levelling-off in terms of infection rate, it is vitally important to maintain vigilance and develop an in 'use' or point of care surveillance technology that allows for continued monitoring, decreased burden on the Health Service providers but also improvements in patient care.

The existing technique of swabbing and culturing is costly, time-consuming and slow to give results. This delay between swabbing and obtaining a positive or negative result undoubtedly has a human and financial cost that is, for the moment, difficult to quantify.

The magnitude of the health threat posed by *Staphylococcus aureus* (MRSA and MSSA) has not gone unnoticed by public health agencies and governments (Mackenzie, F. M, Struelens, M. J. Towner, K. J, Gould, I. M; *Clin. Microbiol. Infect.*, 2005, 11, 937-954). An increase in the number of instances of community acquired (Panton Valentine Leukocidin positive) and hospital acquired MRSA and MSSA has led many agencies to consider the current control strategies to be ineffective. Carrier screening, surveillance and molecular typing all form the tools for integrated MRSA/MSSA control strategies. However, the weakest link in this strategy is the screening and detection. Whilst the current techniques are reliable, they are costly and time-consuming.

Speed of diagnosis, detection and identification is critical in the management of an infected patient. Traditionally, diagnosis and detection uses two main approaches; the first attempts to identify the pathogen at the site of infection, whilst the second aims to determine the most appropriate treatment with the aim of reducing morbidity and mortality (Caroline Atardo Genco and Lee Wetzler; *Neisseria—Molecular Mechanisms of Pathogenesis*. Caister Academic Press. 2010). Currently the most common identification techniques either rely on biochemical profiling as seen in the API style tests or alternatively using molecular techniques such as PCR or DGGE amongst others. Most commonly a combination of techniques is used (Sintchenko, V. Magrabi, F. Tipper, S; *Medical Informatics and the Internet in Medicine*, 2007, 32, 3, 225-240).

These tests vary in terms of completion times and in the levels of precision. The time taken can vary from a few hours up to 18 hours after initial pure culture and even longer in some cases. It is also well understood that certain phenotypic markers might be altered under the influence of differing environmental conditions. On occasions, antimicrobial susceptibility profiles are also used to aid in diagnosis which requires pure culture. In such situations bacterial identification is most likely to be achieved around 48 hours after initial sample reception, which can hamper patient treatment and have potential implications in terms of infection control.

Commonly, detection methods for these pathogens involve culture in liquid or on solid media. These techniques, including a more recent chromogenic cefatoxin based agar medium, typically detect MRSA and MSSA within 20 to 48 hours especially when the initial diagnosis is presumptive as seen with non-chromogenic detection methodologies. Rapid MRSA/MSSA detection is possible using PCR and hybridisation assays. However, whilst the microbiology can be performed within 1.5 to 6 hours, sampling and transport to an appropriately equipped laboratory means in reality the best turn-around time is 24 hours after admission of a patient. This assumes the testing can be performed 7 days per week 24 hours per day. Recent trials of conventional culture methods and PCR techniques have shown there is a lack of demonstrable benefit in the case of PCR based evaluation (Harbarth, S. Fankhauser, C. Schrenzel, J; *JAMA,* 2008, 299, 1149-1157; Jeyaratnam, D. Whitty, C. J. Phillips, K; *British Medical Journal,* 2008, 336, 927-930).

Another technique, is a variant on the tube coagulase test and is predicated on a tripeptide coupled to a coumarin fluorophore, first synthesised in 1977 (Ford, M. Perry, J. D. Robson, I. Morgan, S. Holliday, M. G. Orr, K. E. Gould, F. K; *Journal of Hospital Infection,* 1999, 41, 2, 133-135; Morita, T. Katcv, H Sadaaki, I. Takada, K. Kimura, T. Sakakibara, S; *J. Biochem.* 1977, 82, 1495-1498).

This tripeptide mimics fibrogen and is cleaved by the coagulase expressed by *S. aureus* (MRSA and MSSA). Loss of the tripeptide results in a change in UV absorption of the coumarin. The sensitivity of this dye is limited and requires cell culture prior to analysis. This is based, in no small part, on the low extinction coefficient of the coumarin fluorophore.

There are three broad groups of approaches towards testing for MRSA; conventional culture, immunocapture and molecular detection. The procedure for conventional culture is time-consuming, involves a sample swab being obtained from the patient/surface, sterile transport to a microbiology lab where it can be used to inoculate a chromogenic agar plate, followed by incubation. Results are not usually available until 24 to 48 hours after the initial swab. With regard to immunocapture methods, methods such as ELISA can be used, this involves either sample culture or polymerised chain reaction (PCR) replication of the sample swab to be carried out before results can be obtained. Single swabs can be processed in approximately 6 hours, however this time drops drastically when running multiple samples. This approach can also be very expensive, requiring a dedicated PCR capable microbiology laboratory.

There are also a number of commercial kits that allow for the detection of pre-formed staphylococcal toxins, however in many cases sample culture and purification is required prior to testing, making use of these kits limited at best. An example of these kits, which is often carried out within small laboratories, is the latex agglutination kit, allowing a result to be obtained in approximately 20 to 24 hours, however there are a number of known problems with the general applicability of these tests.

Rhodamine exhibits a high extinction coefficient and pronounced shift in absorption/emission characteristics in lactone or zwitterionic forms. An existing example for the detection of generic serine proteases is the fluorogenic substrate Ala-Pro-Pro-Cresyl Violet, which is specifically cleaved by dipeptidyl peptidase IV, allowing confocal imaging of DPPIV transfected Jurkat cells (Boonacker, E. Elferink, S. Bardai, S. Fleischer, B, Van Noorden, C; *The Journal of Histochemistry and Cytochemistry*, 2003, 51, 7, 959-968).

EP 2 036 897 discloses stable rhodamine labelled Phosphoramidites and synthesis supports which can be used as a labelling reagent for labelling of oligonucleotides during oligonucleotide synthesis.

WO 03/099780 discloses enzyme assays, and more particularly to protease assays using luminogenic protease substrates that include a rhodamine-based luminophore.

There is a need for rapid diagnosis of infectious agents such as MRSA and MSSA, especially in terms of point of care technologies. Indeed many health bodies are demanding active surveillance for MRSA and MSSA.

The listing or discussion of an apparently prior-published document in this specification should not necessarily be taken as an acknowledgement that the document is part of the state of the art or is common general knowledge.

SUMMARY OF THE INVENTION

The present invention is concerned with compounds of formula I:

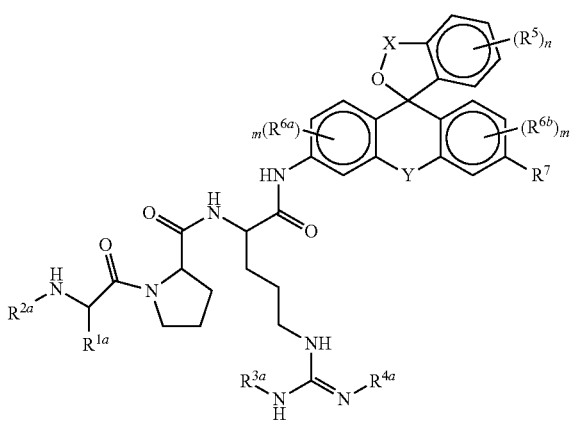

wherein

X represents C(O) or S(O)$_t$;

t represents 1 or 2;

Y represents O, S, NH or CH$_2$;

R$^7$ represents —H, —NO$_2$, —N(H)R$^f$, —N(R$^g$)R$^h$, —OR$^i$, —SR$^i$, —C(O)R$^h$, —C(O)OR$^h$, —C(O)N(H)R$^h$, —C(O)NR$_2$$^h$, —S(O)$_3$R$^h$, —S(O)$_2$N(H)R$^h$, —S(O)$_2$NR$_2$$^h$, aryl or C$_{1-6}$ alkyl, wherein the latter two groups may be optionally substituted with one or more halo or

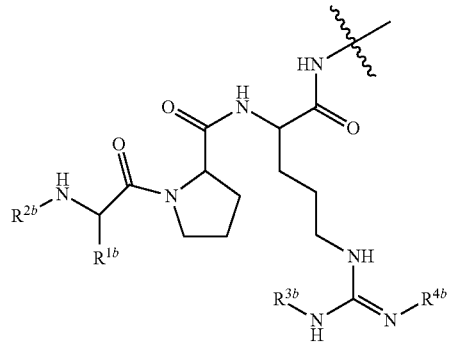

R$^{1a}$ and R$^{1b}$ each independently represent —H, aryl or C$_{1-6}$ alkyl, wherein the latter two groups are optionally substituted with one or more halo;

R$^{2a}$ and R$^{2b}$ each independently represent —H, —OR$^a$, —C(O)R$^a$, —C(O)OR$^b$, a G group, -L-aryl or —C$_{1-6}$ alkyl, wherein the latter two groups may be optionally substituted with one or more halo;

R$^{3a}$, R$^{3b}$, R$^{4a}$ and R$^{4b}$ each independently represent —H, —NO$_2$, —OH, —C(O)R$^c$ or C$_{1-6}$ alkyl, wherein the latter group is optionally substituted with one or more halo;

each R$^5$ independently represents —NO$_2$, —OR$^d$, —NR$^d$$_2$, —SR$^d$, —C(O)R$^e$, —C(O)OR$^e$, —C(O)N(H)R$^e$, —C(O)NR$_2$$^e$, —S(O)$_3$R$^e$, —S(O)$_2$N(H)R$^e$, —S(O)$_2$NR$_2$$^e$, halo, aryl or C$_{1-6}$ alkyl, wherein the latter two groups may be optionally substituted with one or more halo;

and/or any two adjacent R$^5$ groups may be joined together to form, together with the carbon atoms to which they are necessarily attached, a 5- or 6-membered aryl or cycloalkyl group, wherein the latter two groups may be optionally substituted with one or more halo;

n represents 0 to 4;

R$^{6a}$ and R$^{6b}$ independently represents —NO$_2$, —N(H)R$^f$, —N(R$^g$)R$^h$, —OR$^i$, —SR$^i$, —C(O)R$^h$, —C(O)OR$^h$, C(O)N(H)R$^h$, —C(O)NR$_2$$^h$, —S(O)$_3$R$^h$, —S(O)$_2$N(H)R$^h$, —S(O)$_2$NR$_2$$^h$, aryl or C$_{1-6}$ alkyl, wherein the latter two groups may be optionally substituted with one or more halo;

each m independently represents 0 to 3;

each R$^a$ to R$^i$ independently represents —H, aryl, C$_{1-6}$ alkyl, wherein the latter two groups may be optionally substituted with one or more halo;

L represents a direct bond or CH$_2$;

G represents any amino acid which may be further substituted.

In an embodiment of the present invention the compound does not have the structure according to formula A or formula B:

Formula A
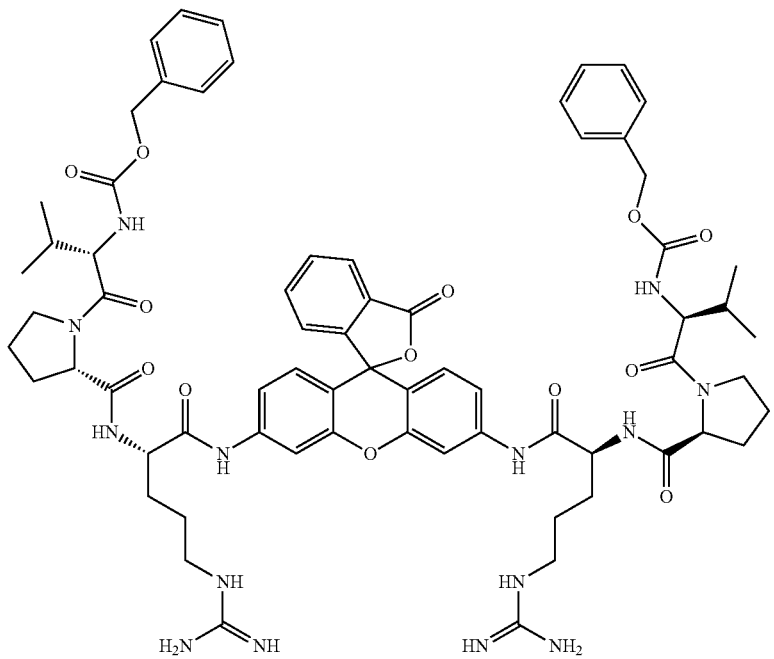
Formula B
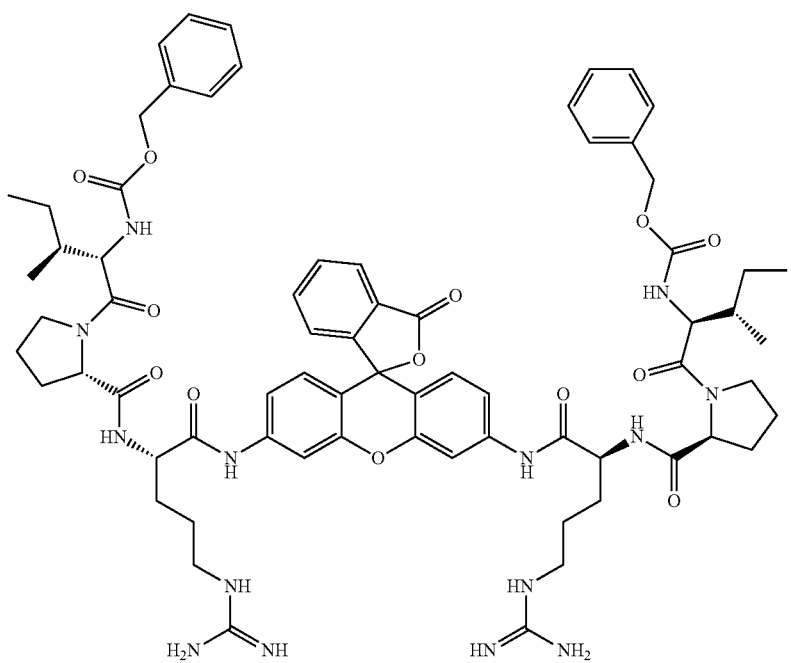

Preferably, wherein $R^7$ is represented by

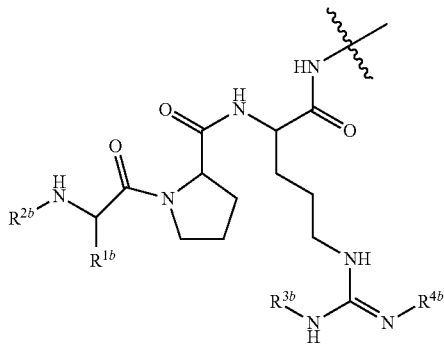

and wherein
X represents C(O) or S(O)$_t$;
t represents 1 or 2;
Y represents O, S, NH or CH$_2$;
$R^{1a}$ and $R^{1b}$ each independently represent H or C$_{1-6}$ alkyl, wherein the latter group is optionally substituted with one or more halo;
$R^{2a}$ and $R^{2b}$ each independently represent H, —C(O)R$^a$, —C(O)OR$^b$, -L-aryl or a G group;
$R^{3a}$, $R^{3b}$, $R^{4a}$ and $R^{4b}$ each independently represent H, —NO$_2$, —OH, —C(O)R$^c$ or C$_{1-6}$ alkyl, wherein the latter group is optionally substituted with one or more halo;
each $R^5$ independently represents halo, —OR$^d$, —C(O)R$^e$, aryl or C$_{1-6}$ alkyl, wherein the latter two groups may be optionally substituted with one or more halo;
and/or any two adjacent $R^5$ groups may be joined together to form, together with the carbon atoms to which they are necessarily attached, a 5- or 6-membered aryl or cycloalkyl group, wherein the latter two groups may be optionally substituted with one or more halo;
n represents 0 to 4;
$R^{6a}$ and $R^{6b}$ each independently represents —N(H)R$^f$, —N(R$^g$)R$^h$, —C(O)R$^h$, —OR$^i$, aryl or C$_{1-6}$ alkyl, wherein the latter two groups may be optionally substituted with one or more halo;
each in independently represents 0 to 3;
each $R^a$ to $R^i$ independently represents C$_{1-6}$ alkyl, optionally substituted with one or more halo;
L represents a direct bond or CH$_2$;
G represents any amino acid which may be further substituted.
In another embodiment when:
X=C(O);
Y=O
$R^{1a}$ and $R^{1b}$ are each isopropyl;
$R^{3a}$, $R^{3b}$, $R^{4a}$ and $R^{4b}$ are each H;
n is 0 for $R^5$; and
m is 0 for $R^{6a}$ and $R^{6b}$;
$R^{2a}$ and $R^{2b}$ may not each be represented by Cbz; and
In another embodiment when:
X=C(O);
Y=O
$R^{2a}$ and $R^{2b}$ are each represented by Cbz;
$R^{3a}$, $R^{3b}$, $R^{4a}$ and $R^{4b}$ are each H;
n is 0 for $R^5$; and
m is 0 for $R^{6a}$ and $R^{6b}$;
$R^{1a}$ and $R^{1b}$ may not each be sec-butyl.
Preferably, wherein $R^{1a}$ and $R^{1b}$ are independently represented by methyl, ethyl, isopropyl, butyl or isobutyl. More preferably wherein $R^{1a}$ and $R^{1b}$ are each isopropyl.

Preferably, wherein $R^{2a}$ and $R^{2b}$ are independently represented by $^t$Boc, Cbz, Bn, Bz or any amino acid however further substituted. More preferably, wherein $R^{2a}$ and $R^{2b}$ are independently represented by $^t$Boc, Bn, Bz or any amino acid however further substituted. Even more preferably, wherein $R^{2a}$ and $R^{2b}$ are each represented by $^t$Boc.
Preferably, wherein the structure is according to formula II:

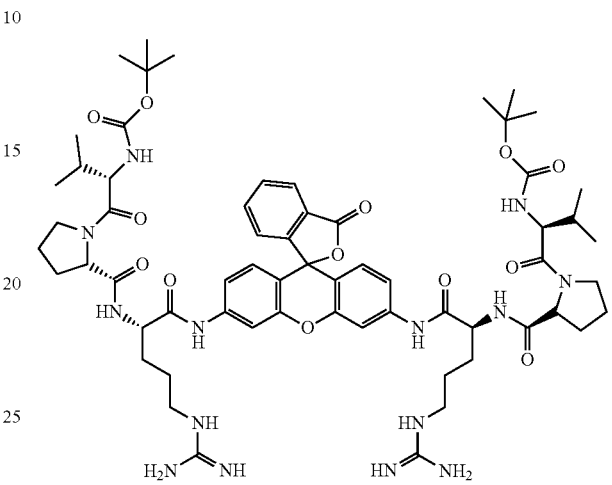

Preferably, in the compound of formula I, m is 0 for $R^{6a}$ and $R^{6b}$,
and wherein X represents C(O) or S(O)$_t$;
t represents 1 or 2;
Y represents O, S, NH or CH$_2$;
$R^5$ represents —NO$_2$, —N(H)R$^f$, —N(R$^g$)R$^h$, —OR$^i$, —SR$^i$, —C(O)R$^h$, —C(O)OR$^h$, —C(O)N(H)R$^h$, —C(O)NR$_2^h$, —S(O)$_3$R$^h$, —S(O)$_2$N(H)R$^h$, —S(O)$_2$NR$_2^h$, wherein each R$^f$ to R$^i$ are independently —H, aryl or C$_{1-6}$ alkyl, wherein the latter two groups may be optionally substituted with one or more halo;
and/or any two adjacent $R^5$ groups may be joined together to form, together with the carbon atoms to which they are necessarily attached, a 5- or 6-membered aryl or cycloalkyl group, wherein the latter two groups may be optionally substituted with one or more halo;
n represents 0 to 4, preferably 0 to 2 (e.g. 1);
$R^7$ represents —H, —NO$_2$, —N(H)R$^f$, —N(R$^g$)R$^h$, —OR$^i$, —SR$^i$, —C(O)R$^h$, —C(O)OR$^h$, —C(O)N(H)R$^h$, —C(O)NR$_2^h$, —S(O)$_3$R$^h$, —S(O)$_2$N(H)R$^h$, —S(O)$_2$NR$_2^h$, aryl or C$_{1-6}$ alkyl, wherein the latter two groups may be optionally substituted with one or more halo;
$R^{3a}$ and $R^{4a}$ each independently represent —H, —NO$_2$, —OH, —C(O)R$^c$ or —C$_{1-6}$ alkyl, wherein the latter group is optionally substituted with one or more halo;
$R^{1a}$ represents —H, -aryl or —C$_{1-6}$ alkyl, wherein the latter two groups may be optionally substituted with one or more halo;
$R^{2a}$ represents —H, —OR$^a$, —C(O)R$^a$, —C(O)OR$^b$, aryl or —C$_{1-6}$ alkyl, wherein the latter two groups may be optionally substituted with one or more halo, wherein each R$^a$ to R$^c$ are independently —H, aryl or C$_{1-6}$ alkyl, wherein the latter two groups may be optionally substituted with one or more halo.
A second aspect of the current invention provides the compound of the current invention, according to any of claims 1 to 6, for use in the detection of a coagulase-producing bacterial strain.

Preferably, wherein the bacterial strain is *Staphylococcus aureus*. Optionally, wherein the bacterial strain is MRSA or MSSA.

A third aspect of the current invention provides the use of the compound of the current invention, according to any of claims 1 to 6, for detecting coagulase-producing bacterial strains. Preferably, wherein the bacterial strain is *Staphylococcus aureus*. Optionally, wherein the bacterial strain is MRSA or MSSA.

A fourth aspect of the current invention provides the use of rhodamine coupled to the tripeptide Val-Pro-Arg for detecting coagulase-producing bacterial strains. Optionally, rhodamine is coupled to one Val-Pro-Arg tripeptide for detecting coagulase-producing bacterial strains. Alternatively, rhodamine is coupled to two Val-Pro-Arg tripeptides for detecting coagulase-producing bacterial strains. Preferably, wherein the bacterial strain is *Staphylococcus aureus*. Optionally, wherein the bacterial strain is MRSA or MSSA.

A fifth aspect of the present invention provides a method of detecting a coagulase-producing bacterial strain comprising: adding a compound of the current invention, as claimed in any one of claims 1 to 6, to a sample containing the bacterial strain; and detecting an optical response.

Advantageously, the method further comprises adding any one or both of the proteins prothrombin and prethrombin to the sample. Preferably, the method further comprises adding prethrombin to the sample.

Preferably, the optical response is a colour change within the visible region of the electromagnetic spectrum. Optionally, wherein the optical response is fluorescence.

Preferably, the sample includes a biological fluid, a tissue sample, a tissue section, a cell sample or a non-biological fluid or substrate.

Preferably, the sample is a human sample or an animal sample.

Conveniently, the sample is a food sample.

According to a sixth aspect of the current invention there is provided a kit for the detection of coagulase-producing bacterial strains comprising: the compound of the invention, as claimed in any one of claims 1 to 6; and any one or both of the proteins prothrombin and prethrombin. Preferably, the method further comprises added prethrombin to the sample.

According to a seventh aspect of the current invention there is provided the rhodamine derivatives RD1 and RD2:

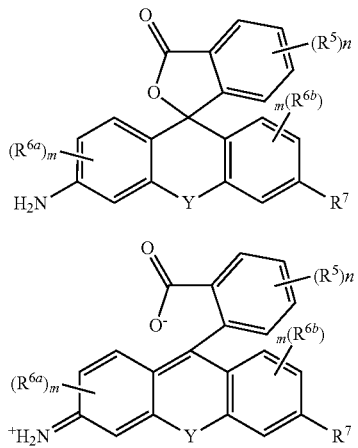

wherein independently in RD1 and RD2;
Y represents O, S, NH or CH$_2$;

$R^7$ may represent —H, —NO$_2$, —N(H)R$^f$, —N(R$^g$)R$^h$, —OR$^i$, —SR$^i$, —C(O)R$^h$, —C(O)OR$^h$, —C(O)N(H)R$^h$, —C(O)NR$_2^h$, —S(O)$_3$R$^h$, —S(O)$_2$N(H)R$^h$, —S(O)$_2$NR$_2^h$, aryl or C$_{1-6}$ alkyl, wherein the latter two groups may be optionally substituted with one or more halo;

each $R^6$ independently represents —NO$_2$, —OR$^d$, —NR$^d_2$, —SR$^d$, —C(O)R$^e$, —C(O)OR$^e$, —C(O)N(H)R$^e$, —C(O)NR$_2^e$, —S(O)$_3$R$^e$, —S(O)$_2$N(H)R$^e$, —S(O)$_2$NR$_2^e$, halo, aryl or C$_{1-6}$ alkyl, wherein the latter two groups may be optionally substituted with one or more halo;

and/or any two adjacent $R^5$ groups may be joined together to form, together with the carbon atoms to which they are necessarily attached, a 5- or 6-membered aryl or cycloalkyl group, wherein the latter two groups may be optionally substituted with one or more halo;

n represents 0 to 4;

$R^{6a}$ and $R^{6b}$ independently represents —NO$_2$, —N(H)R$^f$, —N(R$^g$)R$^h$, —OR$^i$, —SR$^i$, —C(O)R$^h$, —C(O)OR$^h$, C(O)N(H)R$^h$, —C(O)NR$_2^h$, —S(O)$_3$R$^h$, —S(O)$_2$N(H)R$^h$, —S(O)$_2$NR$_2^h$, aryl or C$_{1-6}$ alkyl, wherein the latter two groups may be optionally substituted with one or more halo;

each m independently represents 0 to 3;

each $R^d$ to $R^i$ independently represents —H, aryl, C$_{1-6}$ alkyl, wherein the latter two groups may be optionally substituted with one or more halo.

According to an eighth aspect of the current invention there is provided a method for making the compounds of the present invention wherein $R^7$ is represented by:

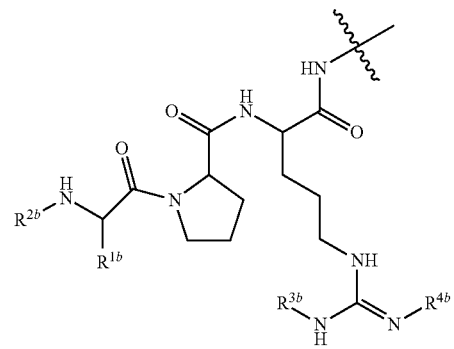

comprising the steps of:
mixing a carboxylic acid and a diamine in the presence of a peptide coupling agent;
wherein
the carboxylic acid is represented by the structure:

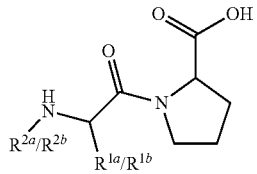

wherein $R^{1a}/R^{1b}$ represents —H, aryl or C$_{1-6}$ alkyl, wherein the latter two groups are optionally substituted with one or more halo;

$R^{2a}/R^{2b}$ represents —H, —OR$^a$, —C(O)R$^a$, —C(O)OR$^b$, a G group, -L-aryl or —C$_{1-6}$ alkyl, wherein the latter two groups may be optionally substituted with one or more halo; and the diamine is represented by the structure:

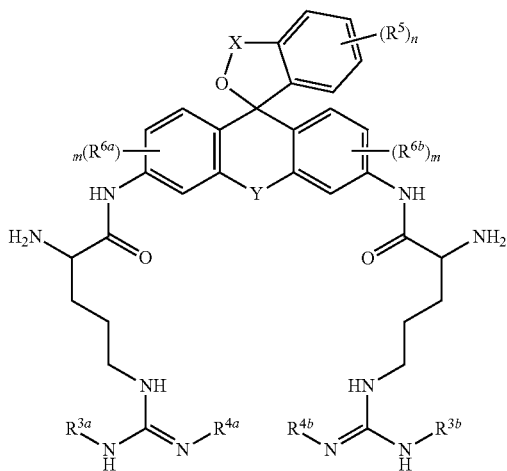

X represents C(O) or S(O)$_t$;
t represents 1 or 2;
Y represents O, S, NH or CH$_2$;
R$^{3a}$, R$^{3b}$, R$^{4a}$ and R$^{4b}$ each independently represent —H, —NO$_2$, —OH, —C(O)R$^c$ or C$_{1-6}$ alkyl, wherein the latter group is optionally substituted with one or more halo;
each R$^5$ independently represents —NO$_2$, —OR$^d$, —NR$^d_2$, —SR$^d$, —C(O)R$^e$, —C(O)OR$^e$, —C(O)N(H)R$^e$, —C(O)NR$^e_2$, —S(O)$_3$R$^e$, —S(O)$_2$N(H)R$^e$, —S(O)$_2$NR$^e_2$, halo, aryl or C$_{1-6}$ alkyl, wherein the latter two groups may be optionally substituted with one or more halo;
and/or any two adjacent R$^5$ groups may be joined together to form, together with the carbon atoms to which they are necessarily attached, a 5- or 6-membered aryl or cycloalkyl group, wherein the latter two groups may be optionally substituted with one or more halo;
n represents 0 to 4;
R$^{6a}$ and R$^{6b}$ independently represents —NO$_2$, —N(H)R$^f$, —N(R$^g$)R$^h$, —OR$^i$, —SR$^i$, —C(O)R$^h$, —C(O)OR$^h$, C(O)N(H)R$^h$, —C(O)NR$^h_2$, —S(O)$_3$R$^h$, —S(O)$_2$N(H)R$^h$, —S(O)$_2$NR$^h_2$, aryl or C$_{1-6}$ alkyl, wherein the latter two groups may be optionally substituted with one or more halo;
each m independently represents 0 to 3;
each R$^a$ to R$^i$ independently represents —H, aryl, C$_{1-6}$ alkyl, wherein the latter two groups may be optionally substituted with one or more halo.

Preferably, wherein the peptide coupling agent is a uronium peptide coupling agent such as HATU ((dimethylamino)-N,N-dimethyl(3H-[1,2,3]triazolo[4,5-b]pyridin-3-yloxy)methaniminium hexafluorophosphate), HBTU (2-(1H-benzotriazole-1-yl)-1,1,3,3-tetramethyluronium hexafluorophosphate), HCTU (O-(1H-6-chlorobenzotriazole-1-yl)-1,1,3,3-tetramethyluronium hexafluorophosphate) or COMU (1-[(1-(cyano-2-ethoxy-2-oxoethylideneaminooxy) dimethylaminomorpholino)] uronium hexafluorophosphate). More preferably, wherein the peptide coupling agent is COMU.

The present invention provides a robust, cost effective and technologically flexible platform that can be taken to the bed side and used to provide an accurate and rapid diagnosis of the type of harmful organism present in/on the patient and is achievable with the current proposal described.

The present invention provides rapid single and multiple pathogen detection via a direct swab from skin, saliva, mucous membrane, wounds, urine and faeces, being exposed to a sample of colour change indicator. A change in colour after a set period of time indicates a positive result for the pathogen and would enable the patient to be rapidly isolated and treated using current/future treatment protocols. This form of direct sampling and identification would facilitate a rapid methodology that can be used at the bedside or as a pre-admission screen represents a significant advancement in early diagnosis/screening. The earlier an infection or a carrier is identified then the sooner an effective method of treatment or containment can be put in place.

The compounds of formula I and II (both all of the compounds of formula I and formula II when limited by the provisos) are referred to hereinafter as "the compounds of the invention". The compound according to formula II is referred to hereinafter as "LGX".

The comments below relating to the compounds of the invention and their uses apply to all compounds within the definition of formula I and II. It should also be understood that in a particular aspect of the invention compounds of formula I, as restricted by the provisos, are used in the applications, uses, formulations etc discussed below.

Compounds of the invention may contain double bonds and may thus exist as E (entgegen) and Z (zusammen) geometric isomers about each individual double bond. All such isomers and mixtures thereof are included within the scope of the invention.

Compounds of the invention may also exhibit tautomerism. All tautomeric forms and mixtures thereof are included within the scope of the invention. Unless otherwise specified, alkyl groups defined herein may be straight-chain or, when there is a sufficient number (i.e. a minimum of two or three, as appropriate) of carbon atoms, be branched-chain, and/or cyclic so forming a cycloalkyl group. Such cycloalkyl groups may be monocyclic or bicyclic and may further be bridged. Further, when there is a sufficient number (i.e. a minimum of four) of carbon atoms, such groups may also be part cyclic. Such alkyl groups may also be saturated or, when there is a sufficient number (i.e. a minimum of two) of carbon atoms, be unsaturated forming, for example, an alkenyl or an alkynyl group.

The terms "halogen" or "halo", when used herein, includes fluoro, chloro, bromo and iodo.

Aryl groups that may be mentioned include C$_{6-14}$ (such as C$_{6-13}$ (e.g. C$_{6-10}$)) aryl groups. Such groups may be monocyclic or bicyclic and have between 6 and 14 ring carbon atoms, in which at least one ring is aromatic. C$_{6-14}$ aryl groups include phenyl, naphthyl and the like, such as 1,2,3,4-tetrahydronaphthyl, indenyl, indenyl and fluorenyl. Other aryl groups which may be mentioned include those where the rings are directly linked but not fused, e.g. biphenyl. The point of attachment of aryl groups may be via any atom of the ring system. However, when aryl groups are bicyclic or tricyclic, they are linked to the rest of the molecule via an aromatic ring.

For the avoidance of doubt, in cases in which the identity of two or more substituents in a compound of the invention may be the same, the actual identities of the respective substituents are not in any way interdependent. For example, in the situation in which X$^1$ and X$^2$ both represent a halogen, the halogens in question may be the same or different.

The substituents R$^1$ and R$^2$ etc in final compounds of the invention or relevant intermediates may be modified one or more times, after or during the processes described above by way of methods that are well known to those skilled in the art. Examples of such methods include substitutions, reductions, oxidations, alkylations, acylations, hydrolyses, esterifications, etherifications, halogenations or nitrations. Such reactions may result in the formation of a symmetric or asymmetric final compound of the invention or intermediate. The precursor groups can be changed to a different such group, or to the groups defined in formula I, at any time during the reaction sequence. In this respect, the skilled person may also refer to "*Comprehensive Organic Functional Group Transformations*" by A. R. Katritzky, O. Meth-Cohn and C. W. Rees, Pergamon Press, 1995.

Compounds of the invention may be isolated from their reaction mixtures using conventional techniques (e.g. recrystallisations).

It will be appreciated by those skilled in the art that, in the processes described above and hereinafter, the functional groups of intermediate compounds may need to be protected by protecting groups. The protection and deprotection of functional groups may take place before or after a reaction in the above-mentioned schemes.

Protecting groups may be removed in accordance with techniques that are well known to those skilled in the art and as described hereinafter. For example, protected compounds/intermediates described herein may be converted chemically to unprotected compounds using standard deprotection techniques. By 'protecting group' we also include suitable alternative groups that are precursors to the actual group that it is desired to protect. For example, instead of a 'standard' amino protecting group, a nitro or azido group may be employed to effectively serve as an amino protecting group, which groups may be later converted (having served the purpose of acting as a protecting group) to the amino group, for example under standard reduction conditions described herein.

The type of chemistry involved will dictate the need, and type, of protecting groups as well as the sequence for accomplishing the synthesis.

The use of protecting groups is fully described in "*Protective Groups in Organic Synthesis*", $3^{rd}$ edition, T. W. Greene & P. G. M. Wutz, Wiley-Interscience (1999).

The term "coagulase-producing bacterial strain" as used herein refers to a bacterial strain that produces the enzyme coagulase.

BRIEF DESCRIPTION OF THE DRAWINGS

The present invention will now be described, by way of example, with reference to the accompanying figures, in which:

FIG. 2A shows MRSA $10^6$ Concentration with 50 μM LGX;

FIG. 2B shows MRSA $10^5$ Concentration with 50 μM LGX;

FIG. 2C shows MRSA $10^3$ Concentration with 50 μM LGX;

FIG. 2D shows MRSA $10^2$ Concentration with 50 μM LGX;

FIG. 4A shows MSSA $10^6$ Concentration with 50 μM LGX;

FIG. 4B shows MSSA $10^5$ Concentration with 50 μM LGX;

FIG. 4C shows MSSA $10^3$ Concentration with 50 μM LGX;

FIG. 4D shows MSSA $10^2$ Concentration with 50 μM LGX;

FIG. 6A (1) shows *E. coli* $10^6$ Concentration with 50 μM LGX;

FIG. 6A (2) (decreased Y axis value): *E. coli* $10^5$ Concentration with 50 μM LGX;

FIG. 6B (1) shows *E. coli* $10^5$ Concentration with 50 μM LGX;

FIG. 6B (2) shows (decreased Y axis value): *E. coli* $10^5$ Concentration with 50 μM LGX;

FIG. 6C (1) shows *E. coli* $10^3$ Concentration with 50 μM LGX;

FIG. 6C (2) shows (decreased Y axis value): *E. coli* $10^3$ Concentration with 50 μM LGX;

FIG. 6D (1) shows *E. coli* $10^2$ Concentration with 50 μM LGX;

FIG. 6D (2) shows (decreased Y axis value): *E. coli* $10^2$ Concentration with 50 μM LGX;

FIG. 7A (1) shows *E. coli* $10^4$ Concentration with 100 μM LGX;

FIG. 7A (2) shows (decreased Y axis value): *E. coli* $10^4$ Concentration with 100 μM LGX;

FIG. 7B (1) shows *E. coli* $10^3$ Concentration with 100 μM LGX;

FIG. 7B (2) shows (decreased Y axis value): *E. coli* $10^3$ Concentration with 100 μM LGX;

FIG. 7C (1) shows *E. coli* $10^2$ Concentration with 100 μM LGX;

FIG. 7C (2) shows (decreased Y axis value): *E. coli* $10^2$ Concentration with 100 μM LGX;

FIG. 8A (1) shows Coagulase Negative *Staphylocci* $10^6$ Concentration with 50 μM LGX;

FIG. 8A (2) shows (decreased Y axis value): Coagulase Negative *Staphylocci* $10^6$ Concentration with 50 μM LGX;

FIG. 8B (1) Coagulase Negative *Staphylocci* $10^5$ Concentration with 50 μM LG;

FIG. 8B (2) shows (decreased Y axis value): Coagulase Negative *Staphylocci* $10^5$ Concentration with 50 μM LGX;

FIG. 8C (1) shows Coagulase Negative *Staphylocci* $10^3$ Concentration with 50 μM LGX;

FIG. 8C (2) shows (decreased Y axis value): Coagulase Negative *Staphylocci* $10^3$ Concentration with 50 μM LGX;

FIG. 8D (1) shows Coagulase Negative *Staphylocci* $10^2$ Concentration with 50 μM LGX;

FIG. 8D (2) shows (decreased Y axis value): Coagulase Negative *Staphylocci* $10^2$ Concentration with 50 μM LGX;

FIG. 9A (1) shows Coagulase Negative *Staphylocci* $10^4$ Concentration with 100 μM LGX;

FIG. 9A (2) shows (decreased Y axis value) Coagulase Negative *Staphylocci* $10^4$ Concentration with 100 μM LGX;

FIG. 9B (1) shows Coagulase Negative *Staphylocci* $10^3$ Concentration with 100 μM LGX;

FIG. 9B (2) shows (decreased Y axis value): Coagulase Negative *Staphylocci* $10^3$ Concentration with 50 μM LGX;

FIG. 9C (1) shows Coagulase Negative *Staphylocci* $10^2$ Concentration with 50 μM LGX;

FIG. 9C (2) shows (decreased Y axis value): Coagulase Negative *Staphylocci* $10^2$ Concentration with 50 μM LGX;

FIG. 16A shows the detection of *S. aureus* in samples by standard techniques and the relative fluorescence of the samples with 100 μM LGX with 1× prothrombin at 15 minutes.

FIG. 16B shows the detection of *S. aureus* in samples by standard techniques and the relative fluorescence of the samples with 100 μM LGX with 1× prothrombin at 30 minutes.

FIG. 16C shows the detection of *S. aureus* in samples by standard techniques and the relative fluorescence of the samples with 100 μM LGX with 1× prothrombin at 60 minutes.

DETAILED DESCRIPTION OF THE INVENTION

Figure 1:
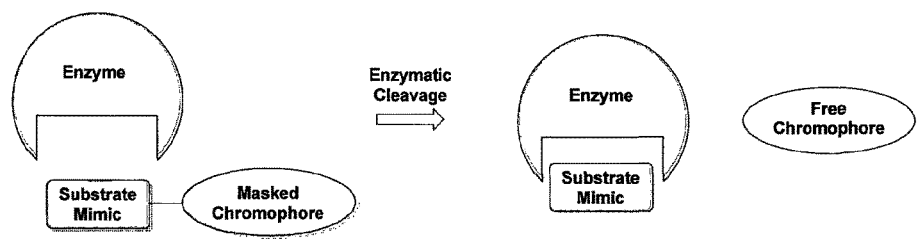
FIG. 1 illustrates the use of a substrate-coupled dye system which is used as a bacterial detecting agent.

The present invention involves the use of rhodamine coupled to the tripeptide Val-Pro-Arg. This generates a bacterial detecting agent for detecting coagulase-producing bacterial strains. In particular, the present invention is concerned with *Staphylococcus aureus* coagulase-specific dye systems which are used as a point of care tool to detect MSSA and MRSA within any healthcare based environment (see FIG. 1).

The key advantages that substrate-coupled dye system according to the present invention has over the highly specific and reliable ELISA and western blotting techniques for protein identification are;

no need for use of expensive monoclonal antibodies;
 no need for reagents for plate development;
 no protracting incubation time for cell culture or pre-enrichment;
 rapid detection (parts per billion quantities of, for example, rhodamine are visible to the naked eye);
 it can be used to detect enzymes in multiple matrices e.g. including directly on surfaces potential for equally high sensitivity to PCR/ELISA techniques The existing molecular method relies upon on MRSA/MSSA coagulase detection. Boc-Val-Pro-Arg-7-AMC (see below) was first reported in 1977 (Ford et al).

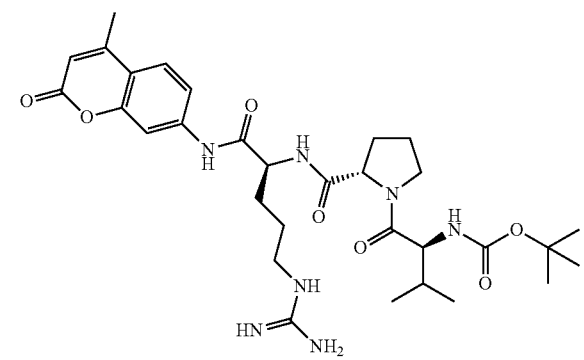 [SMILES: Cc1cc(=O)oc2cc(NC(=O)[C@H](CCCNC(=N)N)NC(=O)[C@@H]3CCCN3C(=O)[C@@H](NC(=O)OC(C)(C)C)C(C)C)ccc12]

The tripeptide had been identified as a substrate that mimics fibrogen and cleavage of the tripeptide from the aminomethylcoumarin (AMC) by MRSA coagulase complex results in a shift in the fluorescence and UV spectrum of the compound. This shift can be used to identify the coagulase and consequently the MRSA. One of the drawbacks is sensitivity, requiring cell culture techniques (24 hours), for sufficient quantities of coagulase to be externally expressed for detection to be possible. The other drawback is that there is no colour change observable to the human eye. A further issue is high cost of the BOC-Val-Pro-Arg-7-AMC (Sigma-Aldrich), sufficient for the testing of only small numbers (<5) of samples.

The choice of rhodamine as the chromophore is based on its ability to co-exist as a red zwitterion or colourless lactone. This switch is exploited by attaching a peptide bond to the pendant rhodamine amine groups, thus converting them into electron-deficient amide groups, rendering the coloured zwitterionic structure unable to form. Upon cleavage of the amide bond/s, the zwitterionic form, which is preferred in aqueous solution, will automatically form, granting a substantial change in colour, from colourless to fluorescent yellow.

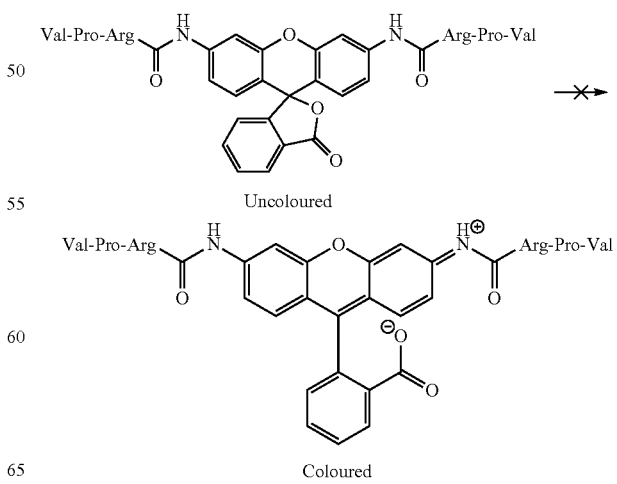

The Val-Pro-Arg tripeptide sequence is known to be a recognisable substrate for staphylothrombin, a complex formed by SA expression of staphylocoagulase and prothrombin. The staphylothrombin complex mistakes the tripeptide for part of the fibrogen protein, which it converts to fibrin. The amidase activity of the staphylothrombin complex is specific to this tripeptide sequence as indicated in previous research and the use of this compound and is the basis of the current commercial tube coagulase test.

LGX is a compound which functions in much the same way, but works as a staphylothrombin assay which is much more sensitive to a given concentration of staphylothrombin, and therefore the number of SA colony forming units.

The estimate of enhanced sensitivity is predicated on the presence of two substrate tripeptides on one dye molecule, essentially doubling the concentration and the fact that coumarin dyes have an extinction coefficient of 20,000 (although not within the visible region), compared to rhodamine extinction coefficient of 110,000.

The current commercial dyes absorb in the UV region at 372 nm and therefore no visible colour change results and fluorescence spectrophotometry must be used to detect the loss of the tripeptide. In the case of the novel compound LGX, it is possible to detect a change within the visible region (488 nm) and therefore, cheaper colorimetery spectrophotometers can be used.

For enhanced sensitivity, however, LGX also has a distinct fluorescence profile, which can also be exploited. The enhanced sensitivity of LGX means that the same quantity of staphylothrombin (and therefore SA colony forming units) can be determined over a much shorter timescale. An alternative view is that smaller quantities of SA bacteria could be identified over the same time period.

LGX works as a staphylothrombin assay to be used in the detection of MRSA and MSSA and is 10 times as sensitive as the existing commercial dye system.

It is to be appreciated that the compound, method and kit of the invention may be used in to detect MSSA and MRSA within any healthcare based environment or agricultural environment. The compound, method and kit of the invention may also be used in to detect MSSA and MRSA in any food or beverage product.

Embodiment 1

In a preferred embodiment of the present invention $R^7$ of formula I is represented by

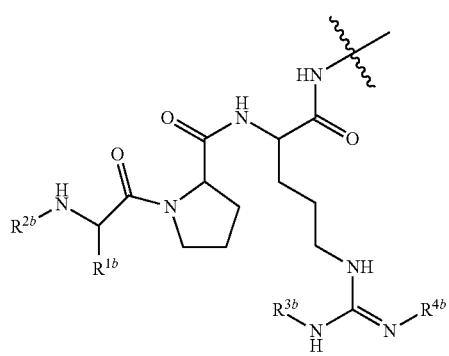

This embodiment is Embodiment 1 of the present invention.

In a preferred embodiment of Embodiment 1, X is C(O).

In a preferred embodiment of Embodiment 1, Y is O, S or NH, preferably O.

In a preferred embodiment of Embodiment 1, $R^{1a}$ and $R^{1b}$ are each independently methyl, ethyl, propyl, isopropyl, butyl, iso-butyl, sec-butyl or tert-butyl, preferably ethyl, propyl, isopropyl, most preferably propyl or isopropyl. In an embodiment of Embodiment 1, $R^{1a}$ and $R^{1b}$ are identical.

In a preferred embodiment of Embodiment 1, $R^{2a}$ and $R^{2b}$ are each independently —H, —OR$^a$, —C(O)R$^a$, —C(O)OR$^b$, preferably C(O)R$^a$ or —C(O)OR$^b$, preferably where $R^a$ and $R^b$ are each independently a methyl, ethyl, propyl, isopropyl, butyl, iso-butyl, sec-butyl or tert-butyl, preferably isopropyl, butyl, iso-butyl, sec-butyl or tert-butyl, most preferably tert-butyl. In an embodiment of Embodiment 1, $R^{2a}$ and $R^{2b}$ are identical.

In a preferred embodiment of Embodiment 1, $R^{3a}$ and $R^{3b}$ are each independently a —H, methyl, ethyl, propyl, isopropyl, butyl, iso-butyl, sec-butyl or tert-butyl, preferably —H, methyl or ethyl, most preferably —H. In an embodiment of Embodiment 1, $R^{3a}$ and $R^{3b}$ are identical.

In a preferred embodiment of Embodiment 1, $R^{4a}$ and $R^{4b}$ are each independently a —H, methyl, ethyl, propyl, isopropyl, butyl, iso-butyl, sec-butyl or tert-butyl, preferably —H, methyl or ethyl, most preferably —H. In an embodiment of Embodiment 1, $R^{4a}$ and $R^{4b}$ are identical.

In embodiments where the any of the substituent groups are aryl or $C_{1-6}$ alkyl, or contain an aryl or $C_{1-6}$ alkyl group, the aryl or $C_{1-6}$ alkyl group may be substituted with one or more halo substituents. In preferred embodiments, they are substituted with 1 to 10 halo substituents, more preferably 1 to 7 and most preferably 1 to 4.

In a preferred embodiment of Embodiment 1, n is 0 or 1, preferably 0.

In a preferred embodiment of Embodiment 1, m is 0 or 1 for both $R^{6a}$ and $R^{6b}$, preferably 0.

When $R^5$ is present, it may occupy any vacant position on the aryl ring. In preferred embodiments $R^5$ occupies the -meta and/or -para position of the aryl ring.

In a preferred embodiment of Embodiment 1:

X is C(O);

Y is O, S or NH, most preferably O;

$R^{1a}$ and $R^{1b}$ are each independently ethyl, propyl, or isopropyl, most preferably isopropyl;

$R^{2a}$ and $R^{2b}$ are each independently C(O)R$^a$ or —C(O)OR$^b$, where $R^a$ and $R^b$ are each preferably isopropyl, butyl, iso-butyl, sec-butyl or tert-butyl, most preferably tert-butyl;

$R^{3a}$ and $R^{3b}$ are each independently —H, methyl or ethyl, most preferably —H;

$R^{4a}$ and $R^{4b}$ are each independently —H, methyl or ethyl, most preferably, —H;

n is 0 or 1, most preferably 0; and m is 0 or 1 for both $R^{6a}$ and $R^{6b}$, most preferably 0.

In a preferred embodiment of Embodiment 1 there is provided,

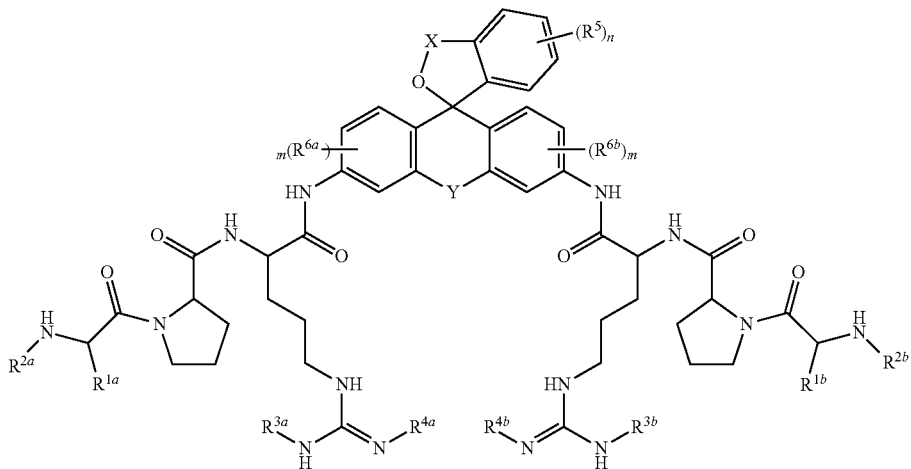

wherein
X represents C(O) or S(O)$_t$;
t represents 1 or 2;
Y represents O, S, NH or CH$_2$;
R$^{1a}$ and R$^{1b}$ each independently represent H or C$_{1-6}$ alkyl, wherein the latter group is optionally substituted with one or more halo;
R$^{2a}$ and R$^{2b}$ each independently represent H, —C(O)R$^a$, —C(O)OR$^b$, -L-aryl or a G group;
R$^{3a}$, R$^{3b}$, R$^{4a}$ and R$^{4b}$ each independently represent H, —NO$_2$, —OH, —C(O)R$^c$ or C$_{1-6}$ alkyl, wherein the latter group is optionally substituted with one or more halo;
each R$^5$ independently represents halo, —OR$^d$, —C(O)R$^e$, aryl or C$_{1-6}$ alkyl, wherein the latter two groups may be optionally substituted with one or more halo;
and/or any two adjacent R$^5$ groups may be joined together to form, together with the carbon atoms to which they are necessarily attached, a 5- or 6-membered aryl or cycloalkyl group, wherein the latter two groups may be optionally substituted with one or more halo;
n represents 0 to 4;
each R$^6$ independently represents —N(H)R$^f$, —N(R$^g$)R$^h$, —C(O)R$^h$, —OR$^i$, aryl or C$_{1-6}$ alkyl, wherein the latter two groups may be optionally substituted with one or more halo;

each m independently represents 0 to 3;
each R$^a$ to R$^i$ independently represents C$_{1-6}$ alkyl, optionally substituted with one or more halo;
L represents a direct bond or CH$_2$;
G represents any amino acid which may be further substituted.

In an embodiment of the present invention when:
X=C(O);
Y=O;
R$^{1a}$ and R$^{1b}$ are each isopropyl;
R$^{3a}$, R$^{3b}$, R$^{4a}$ and R$^{4b}$ are each H; and
n is 0 for R$^5$; and
m is 0 for R$^{6a}$ and R$^{6b}$;
R$^{2a}$ and R$^{2b}$ may not each be represented by Cbz.

In an embodiment of the present invention when:
X=C(O);
Y=O;
R$^{2a}$ and R$^{2b}$ are each represented by Cbz;
R$^{3a}$, R$^{3b}$, R$^{4a}$ and R$^{4b}$ are each H;
n is 0 for R$^5$; and
m is 0 for R$^{6a}$ and R$^{6b}$;
R$^{1a}$ and R$^{1b}$ may not be each be sec-butyl.

In a more preferred embodiment of Embodiment 1 there is provided a compound according to formula III:

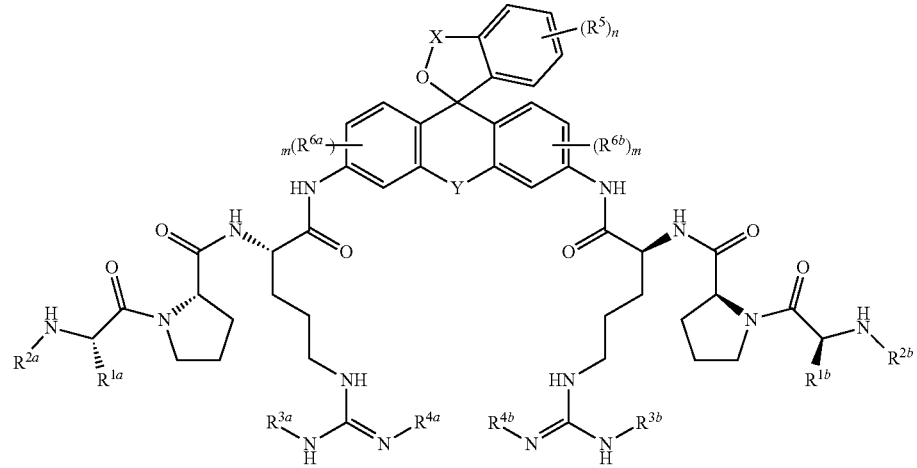

In another embodiment of Embodiment 1 there is provided a compound according to formula IIIa:

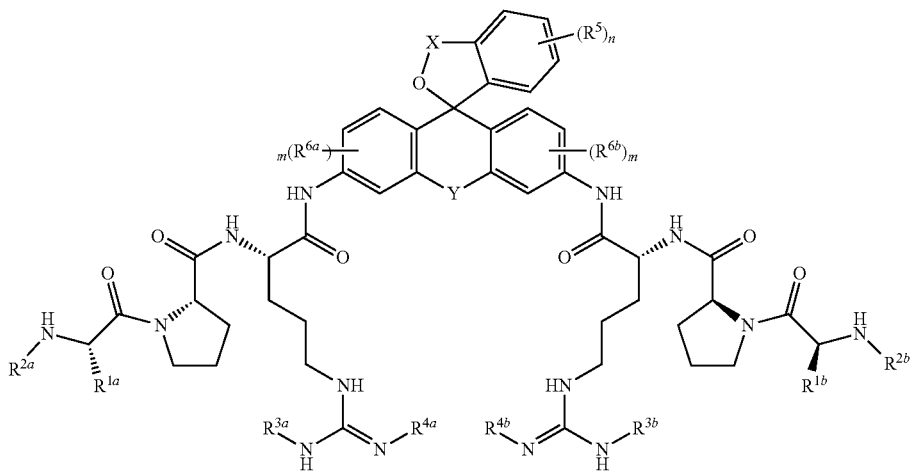

In a further embodiment of Embodiment 1 there is provided a compound according to formula IIIb:

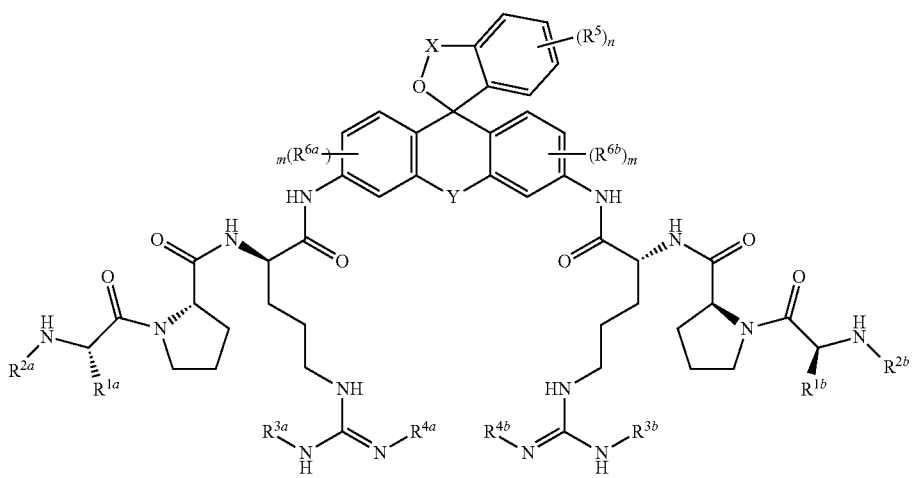

In an aspect of the present invention, there is provided a mixture of the compounds depicted by formula III, formula IIIa and formula IIIb optionally wherein:

the compound of formula III is present in an amount of about 95.0% to about 100% by weight of the mixture;

the compound of formula IIIa is present in an amount of about 0.1% to about 5.0% by weight of the mixture; and the compound of formula IIIb is present in an amount from about 0.001% to about 0.1% by weight of the mixture.

For example, the compound of formula III is present in an amount of about 97.0% to about 99.5% by weight of the mixture;

the compound of formula IIIa is present in an amount of about 1.0% to about 3.0% by weight of the mixture; and the compound of formula IIIb is present in an amount from about 0.01% to about 0.05% by weight of the mixture.

In a particularly preferred embodiment of Embodiment 1, there is provided a compound according to formula II:

Formula II
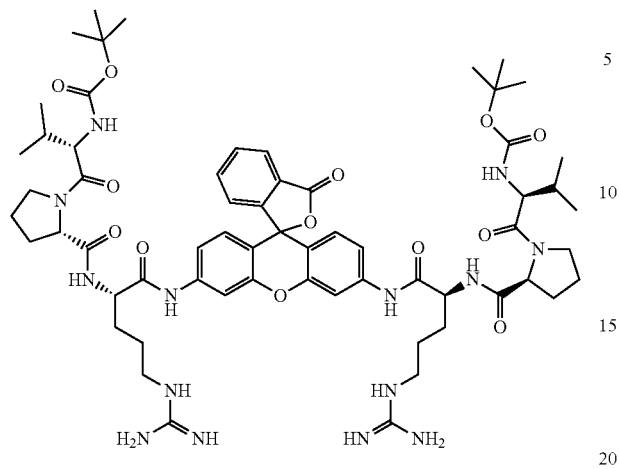
In another embodiment of Embodiment 1 there is provided a compound according to formula IIa and formula IIb:
Formula IIa
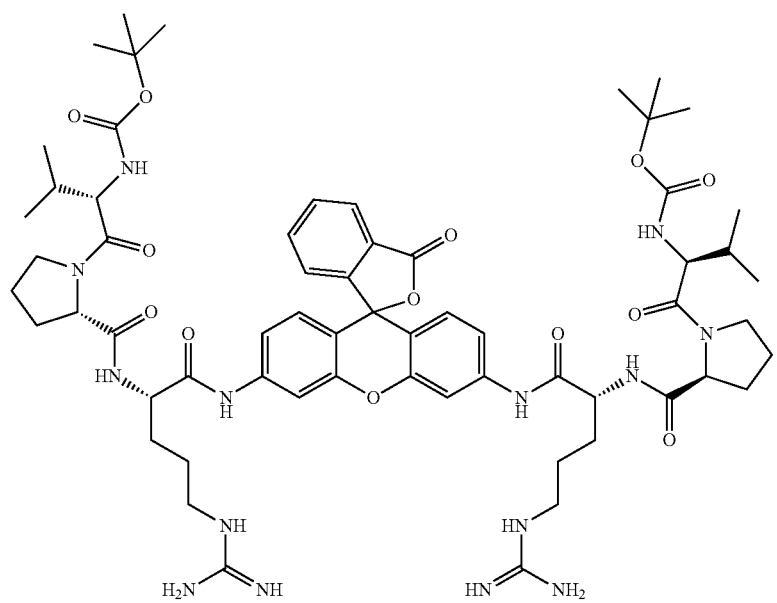

Formula IIb

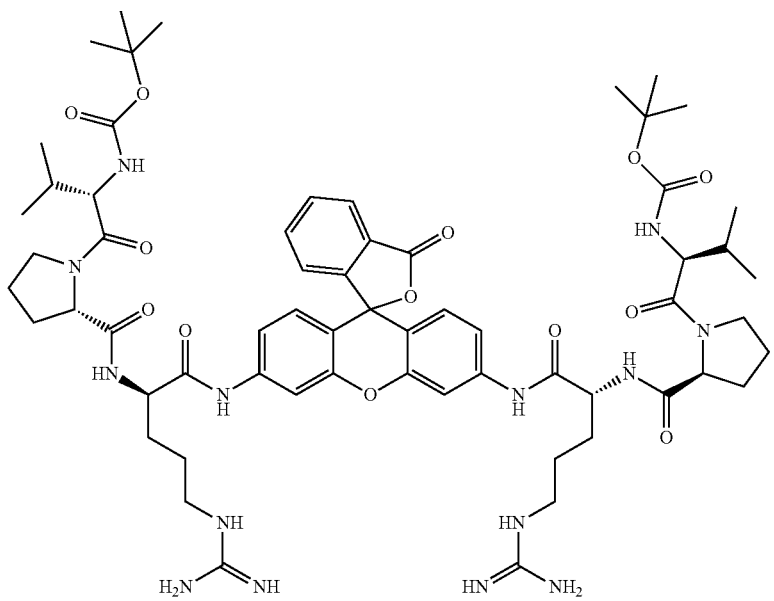

In another aspect of the present invention, there is provided a mixture of the compounds depicted by formula II, formula IIa and formula IIb optionally wherein:

the compound of formula II is present in an amount of about 95.0% to about 100% by weight of the mixture;

the compound of formula IIa is present in an amount of about 0.1% to about 5.0% by weight of the mixture; and the compound of formula IIb is present in an amount from about 0.001% to about 0.1% by weight of the mixture.

Embodiment 2

In a preferred embodiment of the present invention m of formula I is 0 for both $R^{6a}$ and $R^{6b}$.

This embodiment is Embodiment 2 of the present invention.

In a preferred embodiment of Embodiment 2, X is C(O).

In a preferred embodiment of Embodiment 2, Y is O, S or NH, preferably O.

In a preferred embodiment of Embodiment 2, $R^{1a}$ is a methyl, ethyl, propyl, isopropyl, butyl, iso-butyl, sec-butyl or tert-butyl, preferably ethyl, propyl, isopropyl, more preferably propyl or isopropyl, most preferably isopropyl.

In a preferred embodiment of Embodiment 2, $R^{2a}$ is —H, —OR$^a$, —C(O)R$^a$, —C(O)OR$^b$, preferably C(O)R$^a$ or —C(O)OR$^b$, preferably where R$^a$ and R$^b$ are each independently a methyl, ethyl, propyl, isopropyl, butyl, iso-butyl, sec-butyl or tert-butyl, preferably isopropyl, butyl, iso-butyl, sec-butyl or tert-butyl, most preferably tert-butyl.

In a preferred embodiment of Embodiment 2, $R^{3a}$ and $R^{4a}$ each independently represent —H, —NO$_2$, —OH, —C(O)R$^c$ or —C$_{1-6}$ alkyl, wherein the latter group is optionally substituted with one or more halo, preferably —H, methyl, ethyl, propyl, isopropyl, butyl, iso-butyl, sec-butyl or tert-butyl, preferably —H, methyl or ethyl, most preferably —H. In an embodiment of Embodiment 1, $R^{3a}$ and $R^{4a}$ are identical.

In a preferred embodiment of Embodiment 2, $R^5$ and $R^7$ are each independently —NO$_2$, or —OR$^i$, wherein each R$^i$ is independently —H, aryl or C$_{1-6}$ alkyl, wherein the latter two groups may be optionally substituted with one or more halo, and $R^7$ may be —H. In a preferred embodiment R$^i$ is a C$_{1-3}$ alkyl, preferably methyl or ethyl, most preferably methyl.

In embodiments where the any of the substituent groups are aryl or C$_{1-6}$ alkyl, or contain an aryl or C$_{1-6}$ alkyl group, the aryl or C$_{1-6}$ alkyl group may be substituted with one or more halo substituents. In preferred embodiments, they are substituted with 1 to 10 halo substituents, more preferably 1 to 7 and most preferably 1 to 4.

In a preferred embodiment of Embodiment 2, n is 0 or 1.

In Embodiment 2, preferred combinations of $R^5$ and $R^7$ are:

$R^5$ is not present (i.e. n=0), and $R^7$ is —H, —OMe or —NO$_2$; and $R^5$ (n=1) is —OMe or —NO$_2$ and $R^7$ is —H, —OMe or —NO$_2$.

When $R^5$ is present, it may occupy any vacant position on the aryl ring. In preferred embodiments $R^5$ occupies the -meta and/or -para position of the aryl ring.

In a preferred embodiment of Embodiment 2:

X is C(O);

Y is O, S or NH;

$R^{1a}$ is ethyl, propyl, or isopropyl, most preferably isopropyl;

$R^{2a}$ is —C(O)R$^a$ or —C(O)OR$^b$, where R$^a$ and R$^b$ are each preferably isopropyl, butyl, iso-butyl, sec-butyl or tert-butyl, most preferably tert-butyl;

$R^{3a}$ and $R^{4a}$ are independently —H, methyl or ethyl, most preferably —H;

$R^5$ and $R^{6b}$, if present, are each independently —NO$_2$, or —OR$^i$ where R$^i$ is a C$_{1-3}$ alkyl, most preferably methyl; and n is 0 or 1.

In very preferred embodiments of Embodiment 2 the following structures are provided:

-continued
SFG1
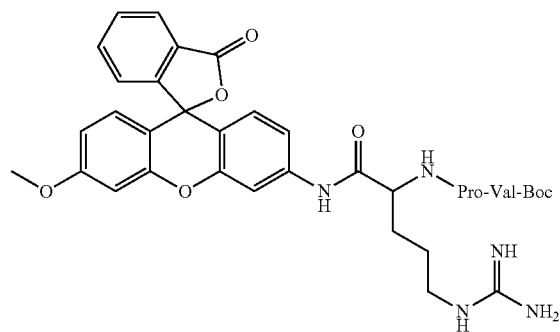
SFG5
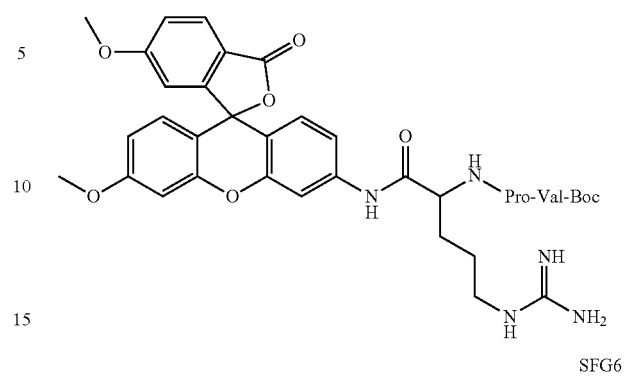
SFG2
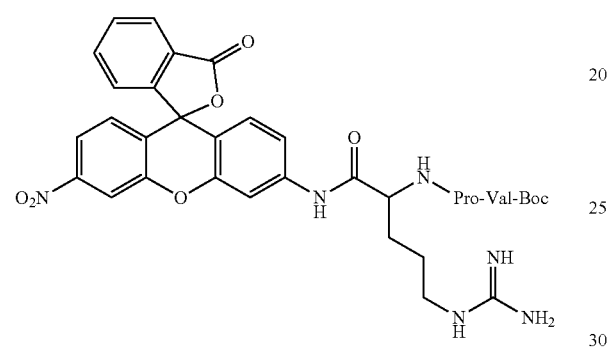
SFG6
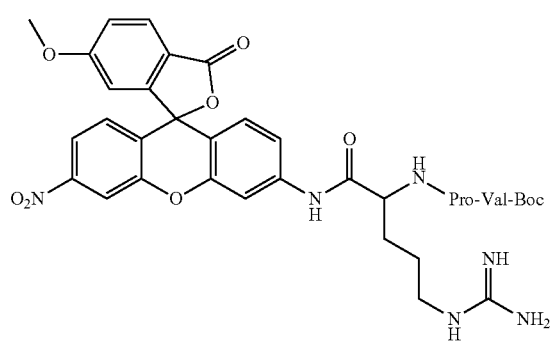
SFG3
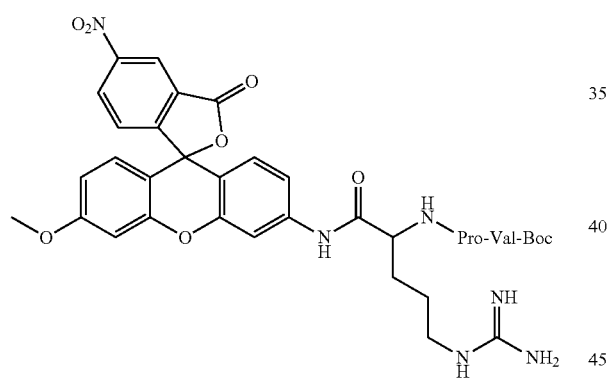
SFG7
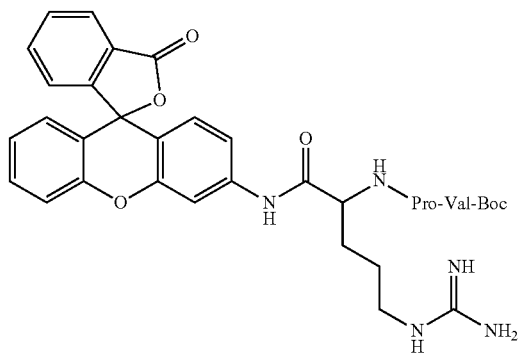
SFG4
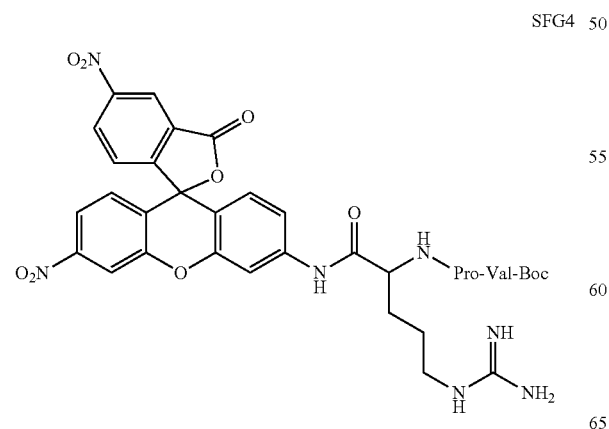
SFG8
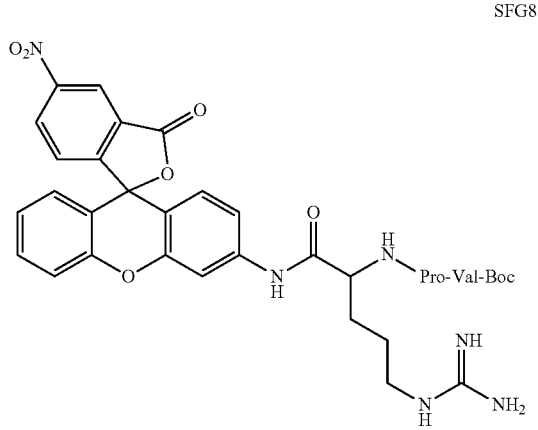

SFG9

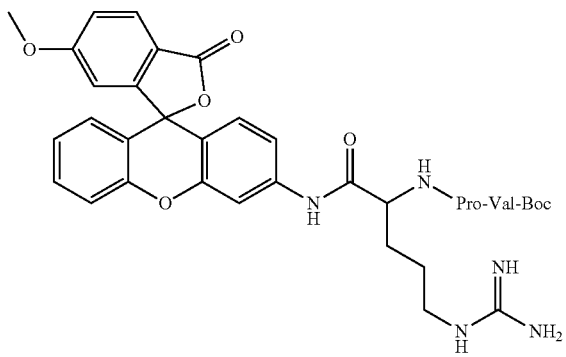

According to another aspect of the present invention there is provided the rhodamine derivatives RD1 and RD2:

RD1

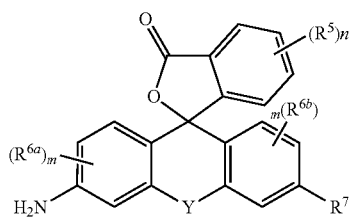

halo, aryl or $C_{1-6}$ alkyl, wherein the latter two groups may be optionally substituted with one or more halo;

and/or any two adjacent $R^5$ groups may be joined together to form, together with the carbon atoms to which they are necessarily attached, a 5- or 6-membered aryl or cycloalkyl group, wherein the latter two groups may be optionally substituted with one or more halo;

n represents 0 to 4;

$R^{6a}$ and $R^{6b}$ independently represents —$NO_2$, —N(H)$R^f$, —N($R^g$)$R^h$, —O$R^i$, —S$R^i$, —C(O)$R^h$, —C(O)O$R^h$, C(O)N(H)$R^h$, —C(O)N$R_2^h$, —S(O)$_3R^h$, —S(O)$_2$N(H)$R^h$, —S(O)$_2$N$R_2^h$, aryl or $C_{1-6}$ alkyl, wherein the latter two groups may be optionally substituted with one or more halo;

each m independently represents 0 to 3;

each $R^d$ to $R^i$ independently represents —H, aryl, $C_{1-6}$ alkyl, wherein the latter two groups may be optionally substituted with one or more halo.

In an embodiment, when the compounds of Embodiment 2 are cleaved by coagulase enzymes from a coagulase-producing bacterial strain, the rhodamine derivative RD1 is produced. In aqueous solutions the rhodamine derivative RD1 will exist predominantly as the fluorescent rhodamine derivative RD2. The fluorescence profiles of the fluorescent rhodamine derivatives RD2 are dependent on the electron donating/electron withdrawing properties of the substituent groups present on the aromatic rings. Accordingly, the detection wavelength and minimum detection concentration of the rhodamine derivatives can be modulated by altering the number and positioning of electron donating/electron withdrawing substituents on the aromatic moieties.

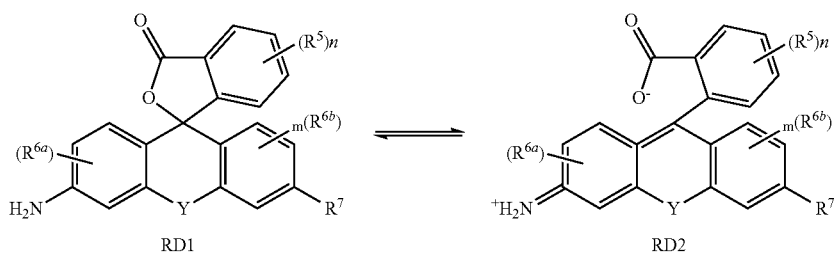

Upon enzymatic cleavage of the amide bond linking the tripeptide sidechain to the rhodamine core in the very preferred compounds of Embodiment 2 (SFG1 to SFG9), the following RD1 rhodamine derivatives are produced.

-continued

RD2

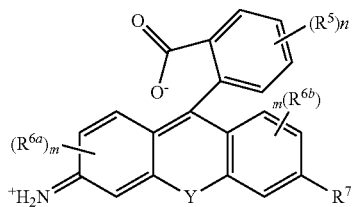

wherein independently in RD1 and RD2;

Y represents O, S, NH or $CH_2$;

$R^7$ may represent —H, —$NO_2$, —N(H)$R^f$, —N($R^g$)$R^h$, —O$R^i$, —S$R^i$, —C(O)$R^h$, —C(O)O$R^h$, —C(O)N(H)$R^h$, —C(O)N$R_2^h$, —S(O)$_3R^h$, —S(O)$_2$N(H)$R^h$, —S(O)$_2$N$R_2^h$, aryl or $C_{1-6}$ alkyl, wherein the latter two groups may be optionally substituted with one or more halo;

each $R^5$ independently represents —$NO_2$, —O$R^d$, —N$R^d_2$, —S$R^d$, —C(O)$R^e$, —C(O)O$R^e$, —C(O)N(H)$R^e$, —C(O)N$R_2^e$, —S(O)$_3R^e$, —S(O)$_2$N(H)$R^e$, —S(O)$_2$N$R_2^e$,

SFG1-RD1

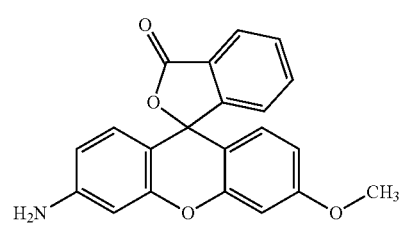

SFG2-RD1
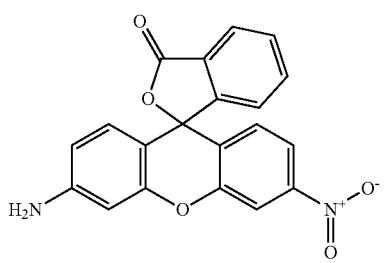

SFG3-RD1
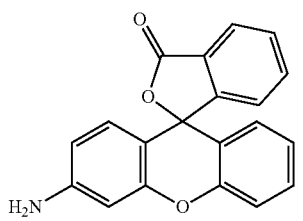

SFG4-RD1
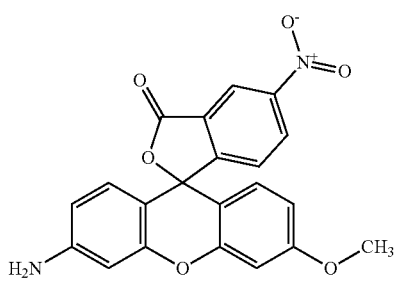

SFG5-RD1
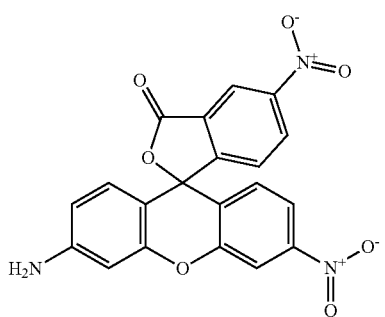

SFG6-RD1
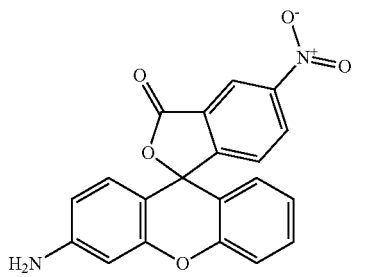

SFG7-RD1
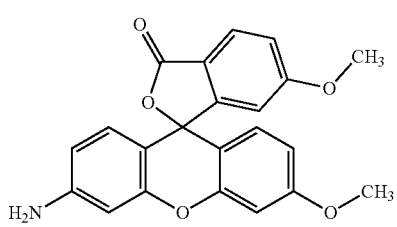

SFG8-RD1
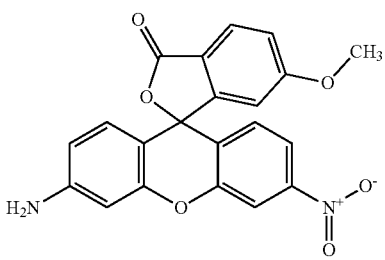

SFG9-RD1
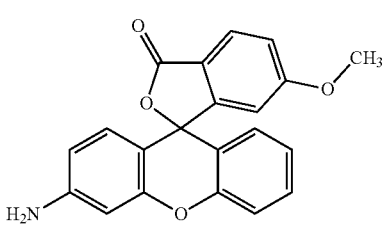

Experimental

To ensure that the effect of staphylocoagulase on fluorescence potential of the compounds of the present invention was not a strain specific phenomenon and was indeed a species specific reaction, various clinical isolates of MRSA (sample name 1-3-12, 13, 15-17, 19-20 inclusive), MSSA (sample name 58-59, 61-64, 66-69, 71, 74 and 65-78 inclusive), and 68-76), *E-coli* (sample name 1-11, 12, 15, and 17, and 1 NTCT strain), and coagulase negative *Staphylococal* species (*S. epidermidis* 1-4, Coagulase negative *S. epidermidis* (CNS), *S. hominus, S. warneri, M. Luteus* and 2 laboratory strains of *S. epidermidis* were cultured on nutrient agar prior to being grown overnight in nutrient broth under shaking conditions at 37° C. Each sample was rinsed liberally in sterile 1×PBS and varying concentrations of bacterial suspension from $10^0$-$10^6$ were generated by serial dilution in 1×PBS. Additionally, bacterial cultures were furthermore maintained on nutrient agar to assess the coagulase status of the isolate.

To determine the effects of varying bacterial concentrations with respect to bacterial strains and concentrations of the compounds according to the present invention on staphylocoagulase activity, 100 and 50 μM solutions containing LGX were prepared in 1×PBS with the addition of 0.05 M Tris Buffer and 0.1 M NaCl to maintain a pH of 8.5 using LGX dissolved in MeOH so that final concentration of methanol was no more than 2.5%. Furthermore, an appropriate concentration (100 μM and 50 μM, respectively) of human prothrombin was added to the solution.

90 μl of 50 μM or 100 μM of prepared LGX solution was added to varying concentrations of bacteria ($10^6$, $10^5$, $10^3$, $10^2$ and $10^4$, $10^3$, $10^2$, $10^0$, respectively) in a microtitre plate and staphylocoagulase activity determined by fluorescence spectrophotometry exhibiting excitation at 488 nm and emission at 525 nm at 15 minute intervals over a 6 hour time period. The plate reader used was a Fluostar Optima, and the plates used were Nunclon Surface 96 well plates. Positive controls for each experiment was a strain of MRSA, and the negative control for each experiment was a strain of *E. coli*, both of which were picked at random to ensure there was no bias within the data. A 1:1 ratio of the LGX solution with PBS was also assayed as "LGX alone" sample, which has been designated as a black line on the graphs below. n=3 cultures were assayed in each case.

In tandem with all fluorometric assays using LGX, the positive/negative/false positive status of coagulase present in each respective bacterial isolates was determined, using a staphylase text kit (Oxoid), under manufacturer's instructions. Loopfuls of bacteria, which had been cultured overnight on agar, were assayed based on coagulase mediated clumping of fibrinogen-sensitised ovine blood cells. As opposed to being a colourometric or fluorometric assay, providing instant visible coagulation of the reagents following exposure to bacteria. n=3 cultures were assayed in each case.

To ensure that the effect of staphylocoagulase on fluorescence potential of the LGX compound was not a strain specific phenomenon and was indeed a species specific reaction, 20 clinical isolates of MRSA were assayed under the same conditions as detailed above, and have been designated the nomenclature MRSA 1-20. Using the staphylase test, all isolates were confirmed to be coagulase positive. As can be observed in FIG. 2A-2D, whereby LGX concentration was at 50 µM and bacterial concentration was $10^6$, $10^5$, $10^3$ and $10^2$, there is a considerable degree of variation in the efficacy of the compound with regard to fluorescence reaching its maximum over time in varying bacterial strains, however, at a $10^6$ bacterial concentration, the maximum level was reached by 2 hours for all samples, whereas at $10^5$, $10^3$ and $10^2$, fluorescence tended to reach maximum at varying times.

It is evident from these results that at high bacterial concentrations of some strains of MRSA ($10^6$), there was an almost instantaneous reaction, with fluorescence reaching the maximum reading of 65,000 RFU within 2 hours in the majority (90%). 10% of the samples failed to reach maximum, however, these were significantly higher than the LGX alone and negative control by several orders of magnitude. At a lower concentration ($10^5$) of both MRSA, a more gradual increase in fluorescence was observed, with fluorescence reaching the maximum reading of 65,000 RFU within 2 hours in the majority (60%). However, 20% of the samples failed to reach maximum fluorescence, within 5 hours, yet, there is still a highly significant discrimination between these "slower" strains than the negative control even at 6 hours.

At even lower concentration ($10^3$ and $10^2$) of MRSA samples, a more gradual increase in fluorescence was observed, with fluorescence reaching the maximum reading of 65,000 RFU within 4 hours in the majority (60% and 40%, respectively). However, 40% and 60% of the samples, respectively, failed to reach maximum fluorescence, within the 6 hour time frame of the experiment, however again there is still a highly significant discrimination between these samples at 6 hours. It is important to note that, in spite of the vast variance in efficacy across the bacterial strains, fluorescence is still significantly higher in all samples when compared to the negative control, where fluorescence remains consistently low across the 6 hour time period.

Figure 3:
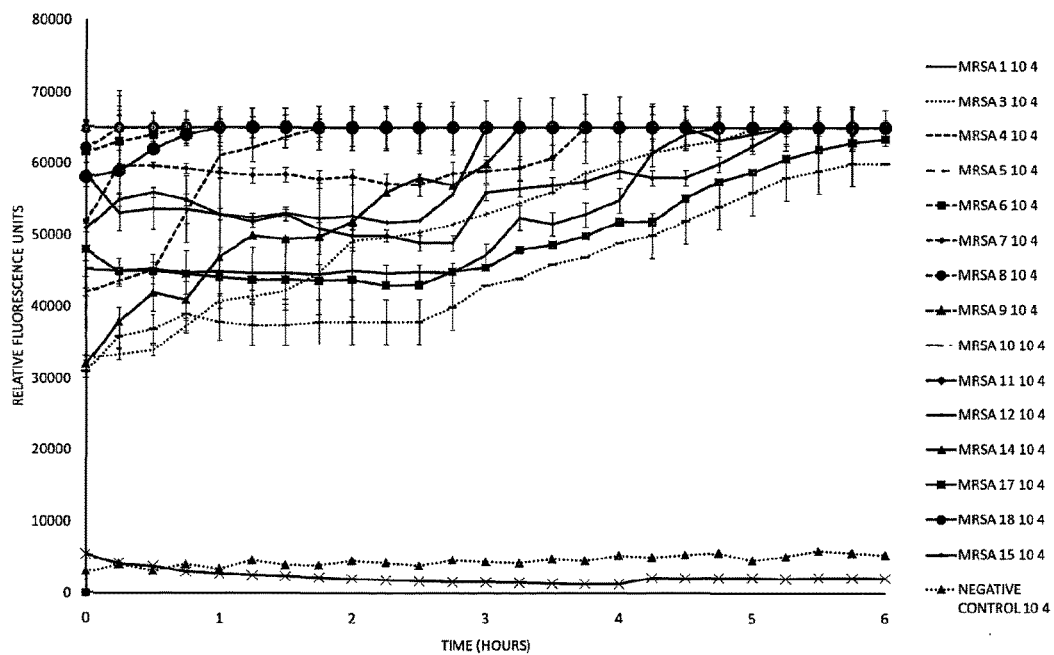
FIG. 3A shows MRSA $10^4$ Concentration with 100 μM LGX.
FIG. 3B shows MRSA $10^3$ Concentration with 100 μM LGX.
FIG. 3C shows MRSA $10^2$ Concentration with 100 μM LGX.
Figure 3:
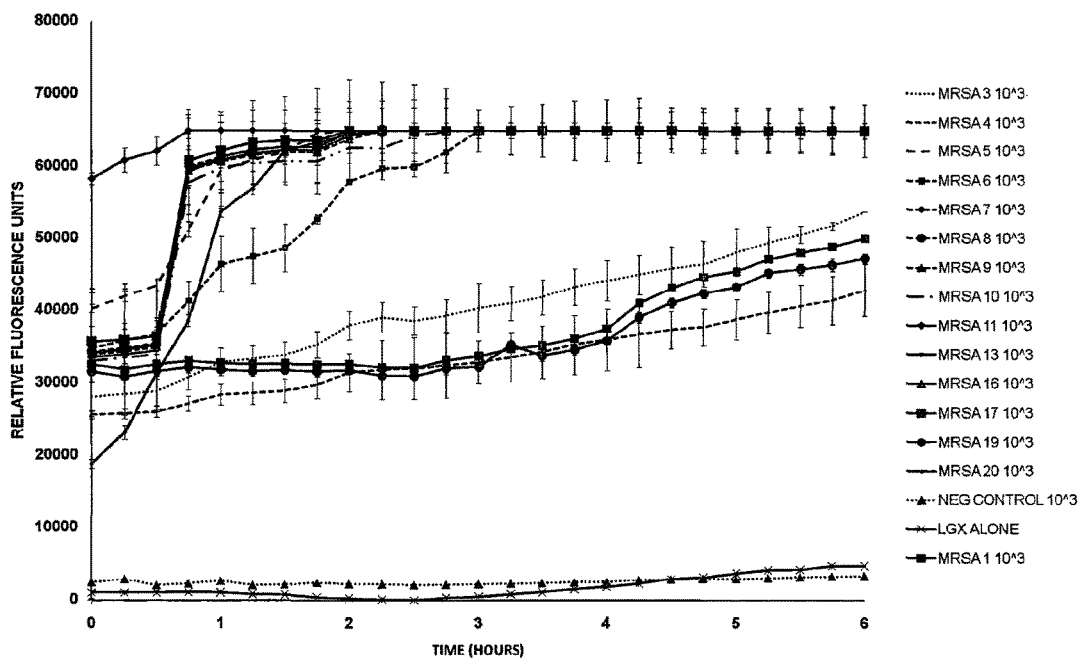
Figure 3:
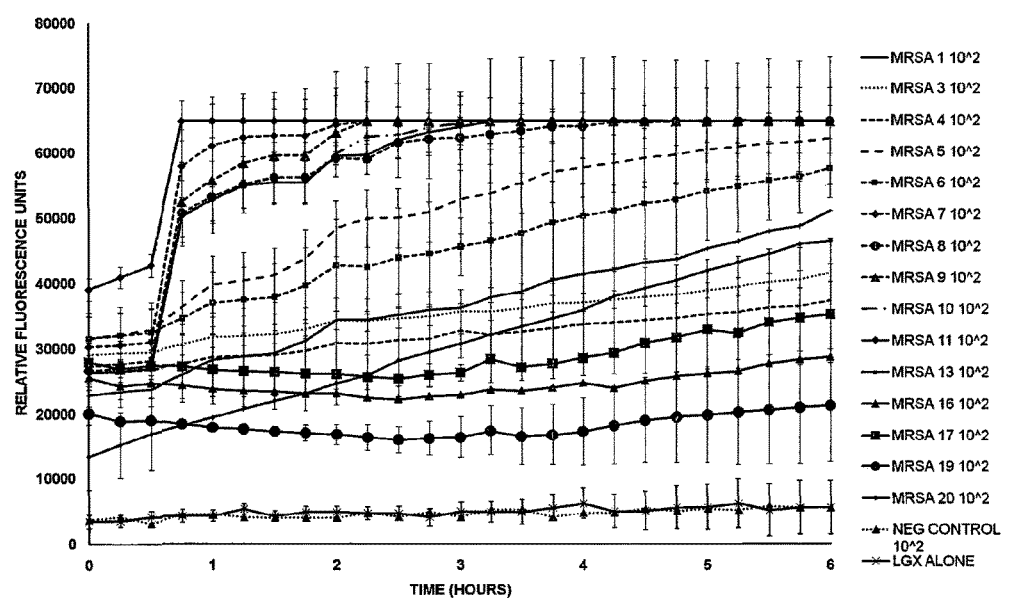

Further to this, using higher concentrations (100 µM) LGX and lower ($10^4$, $10^3$ and $10^3$) bacterial concentrations, as demonstrated in FIG. 3 A-D, results were again consistent with what was observed in FIGS. 2A-D, whereby at higher bacterial concentrations, fluorescence reached its upper limits within 2 hours in 50% of the samples ($10^4$), in 40% of the samples within 3 hours ($10^3$) or within 4 hours in 40% of the samples ($10^2$). Over the 6 hours time period, 90% of MRSA at $10^4$ concentration reached maximum fluorescence, whereas at lower concentrations of $10^3$ and $10^4$, 40% of isolates failed to reach maximum fluorescence, however, a distinction between MRSA strains and the negative control and LGX alone can be observed in all cases, whereby the negative control remained low and failed to demonstrate any increase over time.

20 clinical isolates of MSSA were assayed under the same conditions as detailed above, and have been designated the nomenclature MSSA 58-65, and 68-76. Using the staphylase test, all isolates were confirmed to be coagulase positive. As can be observed in FIG. 4A-D, whereby LGX concentration was at 50 µM and bacterial concentration was $10^6$, $10^5$, $10^3$ and $10^2$, there is a considerable degree of variation in the efficacy of the compound with regard to fluorescence reaching its maximum over time in varying bacterial strains, however, at a $10^6$ bacterial concentration, the maximum level was reached by 2 hours, whereas at $10^5$, $10^3$ and $10^2$, fluorescence tended to reach maximum at varying times. It is evident from these results that at high bacterial concentrations of some strains MSSA ($10^6$), there was an almost instantaneous reaction, with fluorescence reaching the maximum reading of 65,000 RFU in all samples within 1 hour and 45 minutes.

At a lower concentration ($10^5$) of both MSSA, a more gradual increase in fluorescence was observed, with fluorescence reaching the maximum reading of 65,000 RFU within 2 hours in the majority (75%). Only 5% of the samples failed to reach maximum fluorescence, within 6 hours, however again, this was significantly higher than the negative control and LGX alone. At even lower concentration ($10^3$) of MSSA samples, a more gradual increase in fluorescence was observed, with fluorescence reaching the maximum reading of 65,000 RFU in 25% of the samples within 2.5 hours, and within 6 hours 60% of samples had reached maximum fluorescence in the $10^3$ isolates. In the $10^2$ concentration samples, no samples reached maximum fluorescence, yet again, discrimination between MSSA at this concentration and the negative control was observed.

Figure 5:
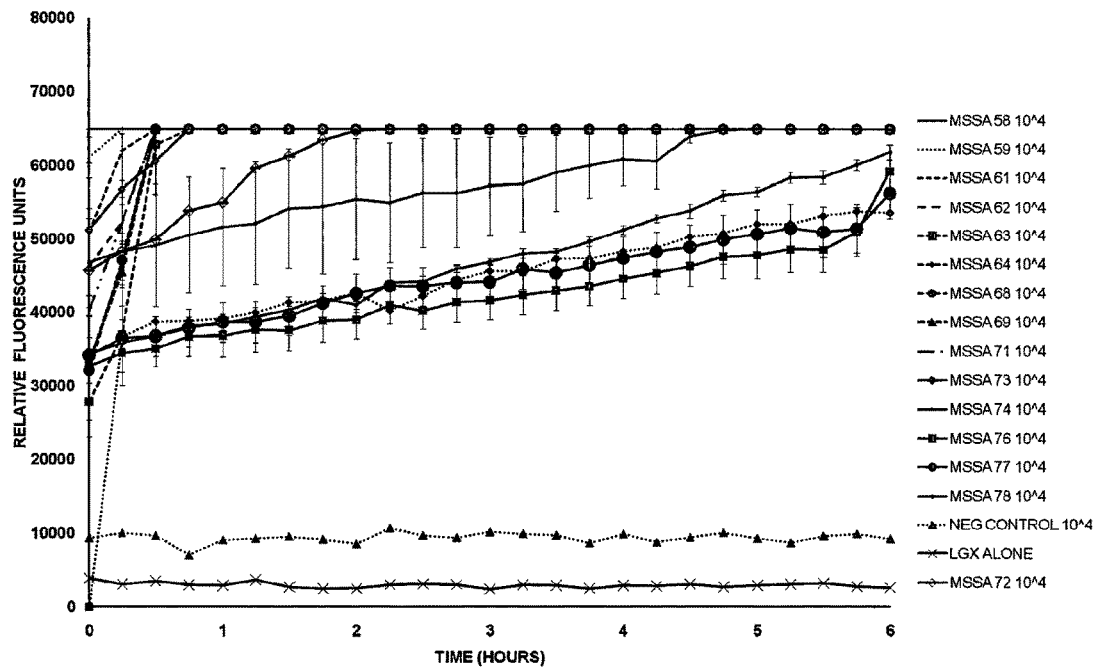
FIG. 5A shows MSSA $10^4$ Concentration with 100 μM LGX.
FIG. 5B shows MSSA $10^3$ Concentration with 100 μM LGX.
FIG. 5C shows MSSA $10^2$ Concentration with 100 μM LGX.
Figure 5:
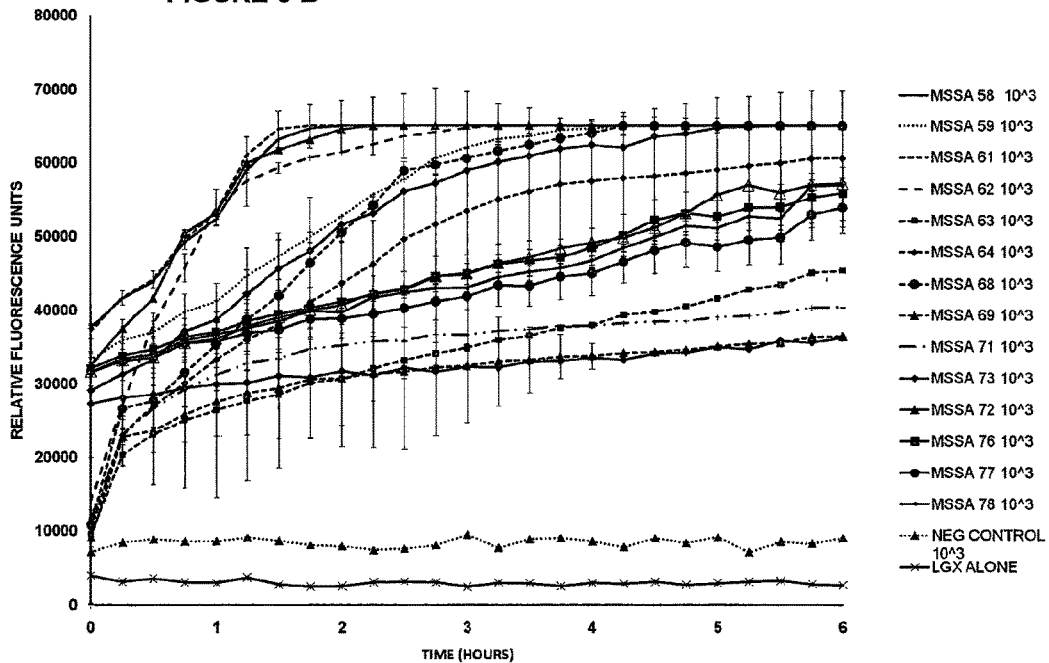
Figure 5:
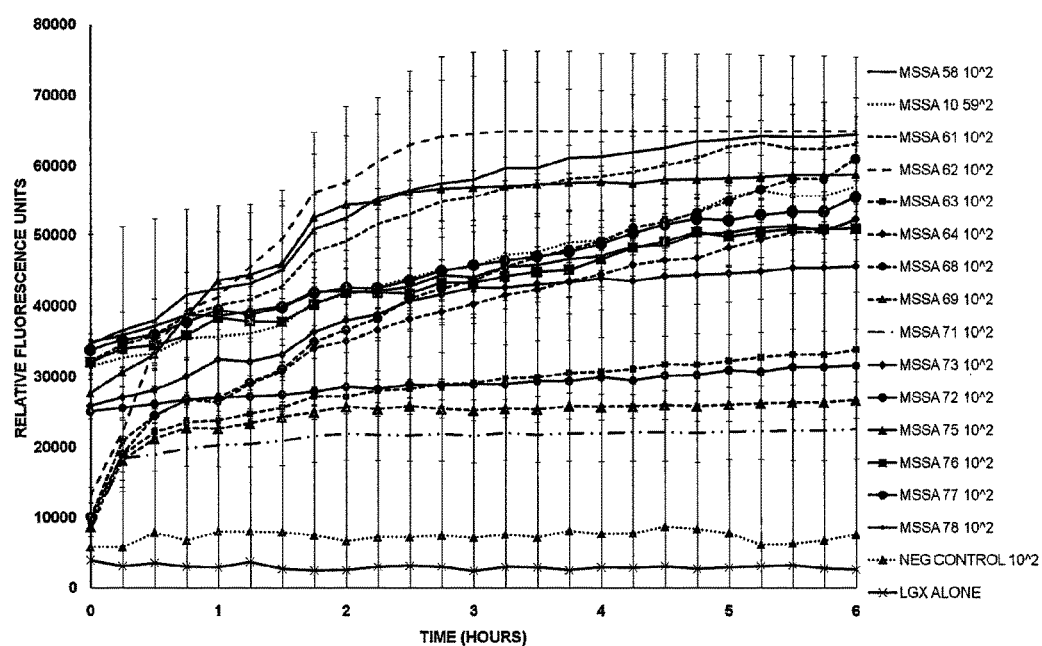

Further to this, using higher concentrations (100 µM) LGX and lower ($10^4$, $10^3$ and $10^3$) bacterial concentrations, as demonstrated in FIGS. 5A-C, results were again consistent with what was observed in FIG. 2A-D, whereby at higher bacterial concentrations, fluorescence reached its upper limits within 1 hours in 70% of the samples ($10^4$), yet, at this concentration, 20% of samples remained below maximum fluorescence, yet results still maintained a differentiation between MSSA and the negative control. 45% of the samples reached maximum fluorescence within 4 hours in the $10^3$ samples, or within 2 hours in 5% of the samples and 25% of the samples over a 6 hour time period ($10^2$). Again, all samples at both $10^3$ and $10^2$ demonstrated a significant discrimination between the presence of MRSA at any concentration and the negative control, again whereby the negative control remained low and failed to demonstrate any increase over time.

To further demonstrate the discriminatory potential of LGX, between coagulase positive MRSA and MSSA and coagulase negative bacterial species, various strains of *E. coli* and proven coagulase negative *staphylocci* were assayed in conjunction with a positive control (MRSA). FIGS. 6, A-D (1 & 2), demonstrates the effect of the presence of high concentrations ($10^6$, $10^5$, $10^3$ and $10^2$) of *E. coli* strains on amide cleavage induced fluorescence of LGX, designated the nomenclature *E. coli* 1-20. It is important to note that graphs have been separated into 1 and 2, 1 being reaching 80000 units on the Y axis and 2 demonstrating a Y axis reaching maximum of 30000, to illustrate the differences in fluorescence units within *E. coli* samples alone.

At $10^6$, $10^5$ and $10^3$ concentrations, fluorescence readings reach a maximum almost immediately or within an hour for the positive control, or at 6 hours for the lower concentrations, whereas the coagulase negative strains of *staphylococci* remain consistently low and tend to not deviate from a baseline level throughout the duration of the experiment. On occasion, there are instances at which fluorescence falls below baseline level, which may be suggestive of hydrolysis of the compound or an alternative mechanism which may affect the fluorescence potential of LGX. It important to note that there is no discrimination between the coagulase negative *staphylococci* at any concentration or at any time point, and results remain consistent throughout the experiment.

Again, as demonstrated by the results depicted in FIGS. 7A-C (1 & 2), and consistent with the data presented in FIG. 4, lower concentrations of the respective bacterial strains ($10^4$, $10^3$ and $10^3$) were assayed in the presence of 100 µM LGX solution and results tended to follow the same pattern, whereby fluorescence, which is relative to staphylocoagulase activity, had a tendency to reach a maximum within 3 hours at all concentrations in MRSA, whereas coagulase negative bacterial strains remained consistently low across the 6 hour time period.

FIGS. 8, A-D (1 & 2), demonstrates the effect of the presence of high concentrations ($10^6$, $10^5$, $10^3$ and $10^2$) of *S. Epidermidis* species, CNS strains, laboratory strains, *S. Hominus, S. Warneri* and *M. luteus*, all of which are coagulase negative, on amide cleavage induced fluorescence of LGX, in comparison to coagulase positive MRSA. It is important to note that graphs have been separated into 1 and 2, 1 being reaching 80000 units on the Y axis and 2 demonstrating a Y axis reaching maximum of 30000, to illustrate the differences in fluorescence units within staphyloccal samples alone. Using the staphylase test, all isolates were confirmed to be coagulase negative, with the exception being *M. luteus*, which proved to demonstrate a false positive result. At $10^6$, $10^6$ and $10^3$ concentrations, fluorescence readings reach a maximum almost immediately or within an hour for the positive control, whereas the coagulase negative strains of *staphylococci* remain consistently low and tend to not deviate from a baseline level throughout the duration of the experiment. On occasion, there are instances at which fluorescence falls below baseline level, which may be suggestive of hydrolysis of the compound or an alternative mechanism which may affect the fluorescence potential of LGX.

It important to note that there is no discrimination between the coagulase negative *staphylococci* and the negative control at any concentration or at any time point, and results remain consistent throughout the experiment. Again, as demonstrated by the results depicted in FIGS. 9A-C (1 & 2), and consistent with the data presented in FIG. 3, lower concentrations of the respective bacterial strains ($10^4$, $10^3$ and $10^3$) were assayed in the presence of 100 µM LGX solution and results tended to follow the same pattern, whereby fluorescence, which is relative to staphylocoagulase activity had a tendency to reach a maximum within 3 hours at all concentrations in MRSA, whereas coagulase negative bacterial strains remained consistently low across the 6 hour time period.

The data shown within this study have amply demonstrated the use of LGX to determine the presence of MRSA and MSSA within a sample, when compared to coagulase negative bacterial strains. Using a large number of isolates, the ability of LGX to rapidly detect the presence of staphylocoagulase in a sample, which is culture independent, abolishes the potential to show a false positive result, and can detect a low concentration of bacteria within a sample, which is based on time. More traditional methods of bacterial detection and diagnosis of infection requires an overnight culture, followed by lab based tests, and potentially more confirmatory tests such as ELISA and PCR, whereas this system may provide a potential for the rapid detection of a bacterium without the need for such a lengthy time period, a "point of care" tool, facilitating prompt diagnosis and treatment of infection.

Conclusions

Across a broad spectrum of bacterial isolates, the use of this system in the identification of MRSA and MSSA in clinical samples or within a laboratory setting requires no culturing and can detect the presence of bacteria as low as $10^2$ concentrations.

Using 50 µM of LGX and $10^4$ and above cell concentrations of both MRSA and MSSA, a fluorescence reading in excess of 20,000 within 30 minutes is considered to be a positive result, however, at $10^3$ and $10^2$ cell concentrations of MRSA and MSSA, 5% and 20%, of isolates, respectively, failed to reach this level of fluorescence, within this 30 minute time limit.

Increasing the concentration of LGX to 100 µM bears a significant effect on the sensitivity and selectivity at lower bacterial concentrations. At $10^3$ cell concentration and above, 100% of MRSA and MSSA samples tested to date gave a fluorescence reading greater than 20,000 within 30 minutes, indicating a positive result. At $10^2$ concentrations of bacteria, a fluorescence reading of 20,000 is achieved within 1 hour in 95% and 90% of MRSA and MSSA samples, respectively.

No response above 5000 fluorescence units was observed in *E. coli* and coagulase negative *staphylococci* at either 50 µM or 100 µM concentrations of LGX within this 1 hour time frame.

At a 50 µM concentration of LGX and using all concentrations of bacteria, more than 80% MRSA and MSSA show a significant absorbance of above 20,000 fluorescence units after 1 hour, whereas 0% of *E. coli* and coagulase negative *staphylocci* show the same response over the same time period.

The Potential of
N-t-BOC-Val-Pro-Arg-7-Amido-4-Methylcoumarin
to Detect Varying Bacterial Species at Varying
Bacterial Concentrations In order to compare and contrast the efficacy of the LGX system, with a similar, well established means of detecting staphylocoagulase (N-t-BOC-val-pro-arg-7-amido-4-methylcoumarin), it was necessary to assess the same spectra of bacterial species and concentrations under the same parameters as used in the LGX system, and also using the same methods which have already been characterised (Ford et al, 1999). As we have already demonstrated, the LGX system effectively detects low bacterial concentrations at a relatively low concentration of compound, and also potently distinguishes between coagulase positive MRSA and MSSA, and coagulase negative *E. coli* and *S. epidermidis*.

As described for the LGX system, clinical isolates of Methicillin Resistant *Staphylococcus Aureus* (MRSA), Methicillin Sensitive *Staphylococcus Aureus* (MSSA), *Staphylococcus Epidermidis* and *Eschericia coli* were cultured on nutrient agar prior to being grown overnight in nutrient broth under shaking conditions at 37° C. To determine the effects of varying bacterial concentrations with respect to bacterial strains and N-t-BOC-val-pro-arg-7-amido-4-methylcoumarin concentrations on staphylocoagulase activity, a direct comparison between the LGX system and the existing use of N-t-BOC-val-pro-arg-7-amido-4-methylcoumarin as a means of detecting staphylocoagulase was necessary (Ford et al, 1999).

100 µM and 500 µM solutions of coumarin solution were prepared in 1×PBS with the addition of 0.05 M Tris Buffer and 0.1 M NaCl to maintain a pH of 8.5 using N-t-BOC-val-pro-arg-7-amido-4-methylcoumarin dissolved in MeOH. Furthermore, 100 µM and 500 µM of human prothrombin was added to the solution. 90 µl of 50 µM or 100 µM of N-t-BOC-val-pro-arg-7-amido-4-methylcoumarin solution was added to varying concentrations of bacteria ($10^6$, $10^5$, $10^4$, $10^3$, $10^2$ and $10^0$, respectively) in a microliter plate and staphylocoagulase activity determined by fluorescence spectrophotometry (Excitation of 355 nm, Emmission of 460 nm) at 15 minute intervals over a 6 hour time period. N=3 cultures were assayed in each case. As with the LXG system, the plate reader used was a Fluostar Optima, and the plates used were Nunclon Surface 96 well plates.

Figure 10:
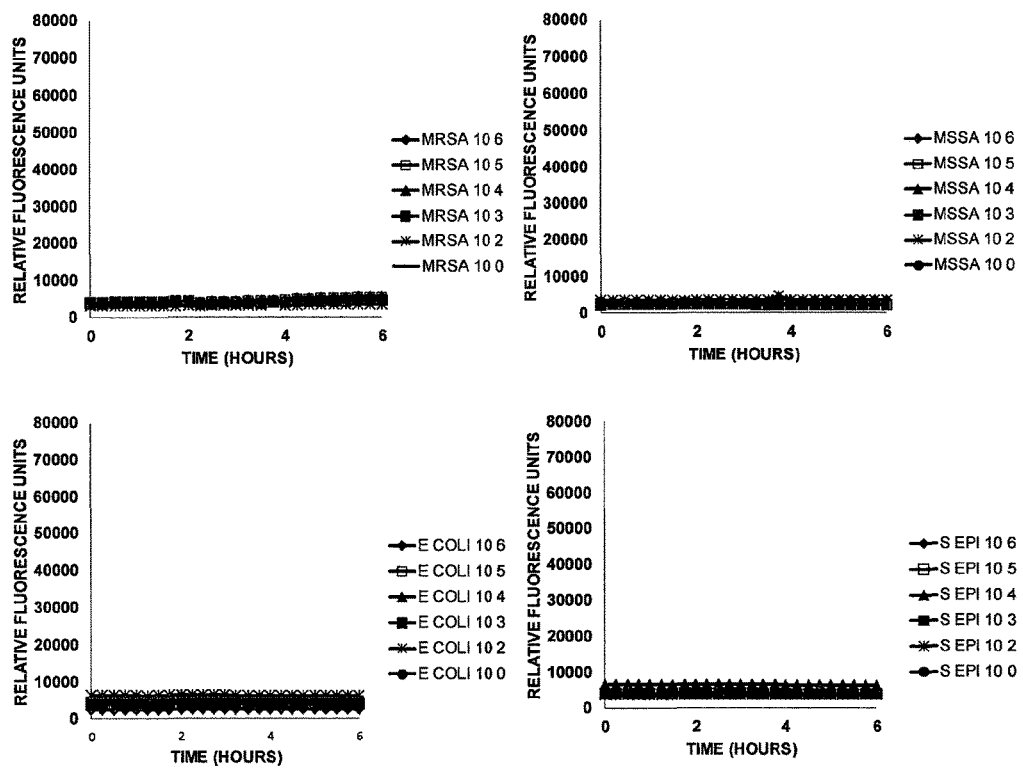
FIG. 10 shows the effects of 500 μM N-t-BOC-val-pro-arg-7-amido-4-methylcoumarin on staphylocoagulase mediated fluorescence in varying bacterial species.

FIG. 10 demonstrates the effect of the presence of varying concentrations of MRSA, MSSA, *S. epidermidis* and *E. coli* on the fluorescence of 500 µM N-t-BOC-val-pro-arg-7-amido-4-methylcoumarin, using the same parameters as used in the LGX system. It is evident from these results that at high bacterial concentrations of all bacterial species ($10^6$), there was little discrimination between the fluorescence of all samples, which is certainly the opposite of what is observed in the LGX system, with the exception being MSSA at $10^6$, whereby a slight increase was observed, but was significantly less than what one would observe using LGX. Further to this, at both high and low concentrations of MRSA, MSSA, *S. epidermidis* and *E. coli*, no increase in fluorescence was observed and results remained consistently low for all bacterial species over the 6 hour time period, thus demonstrating that the use of N-t-BOC-val-pro-arg-7-amido-4-methylcoumarin does not harbour the potential to discriminate between bacterial species at a low concentration.

Figure 11:
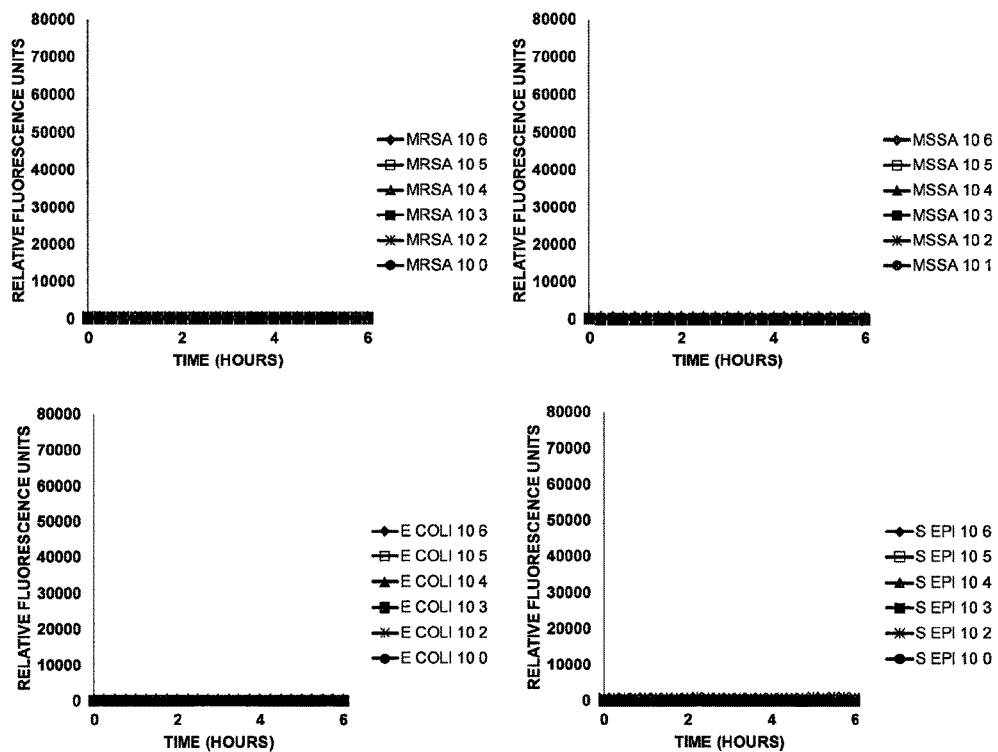
FIG. 11 shows the effects of 100 μM N-t-BOC-val-pro-arg-7-amido-4-methylcoumarin on staphylocoagulase mediated fluorescence in varying bacterial species.

FIG. 11 demonstrates the effect of the presence of varying concentrations of MRSA, MSSA, *S. epidermidis* and *E. coli* on the fluorescence potential of 100 µM N-t-BOC-val-pro-arg-7-amido-4-methylcoumarin. Again, it can be seen that at high bacterial concentrations of MRSA and MSSA ($10^6$ and $10^5$), there is no discrimination between bacterial samples, and this pattern prevails at lower bacterial concentrations in all bacterial species. Again, unlike the LGX system, and consistent with the data presented in FIG. 10, exceptionally high concentrations of N-t-BOC-val-pro-arg-7-amido-4-methylcoumarin were not capable of distinguishing between bacterial species at low concentrations over a 6 hour time period.

Figure 12:
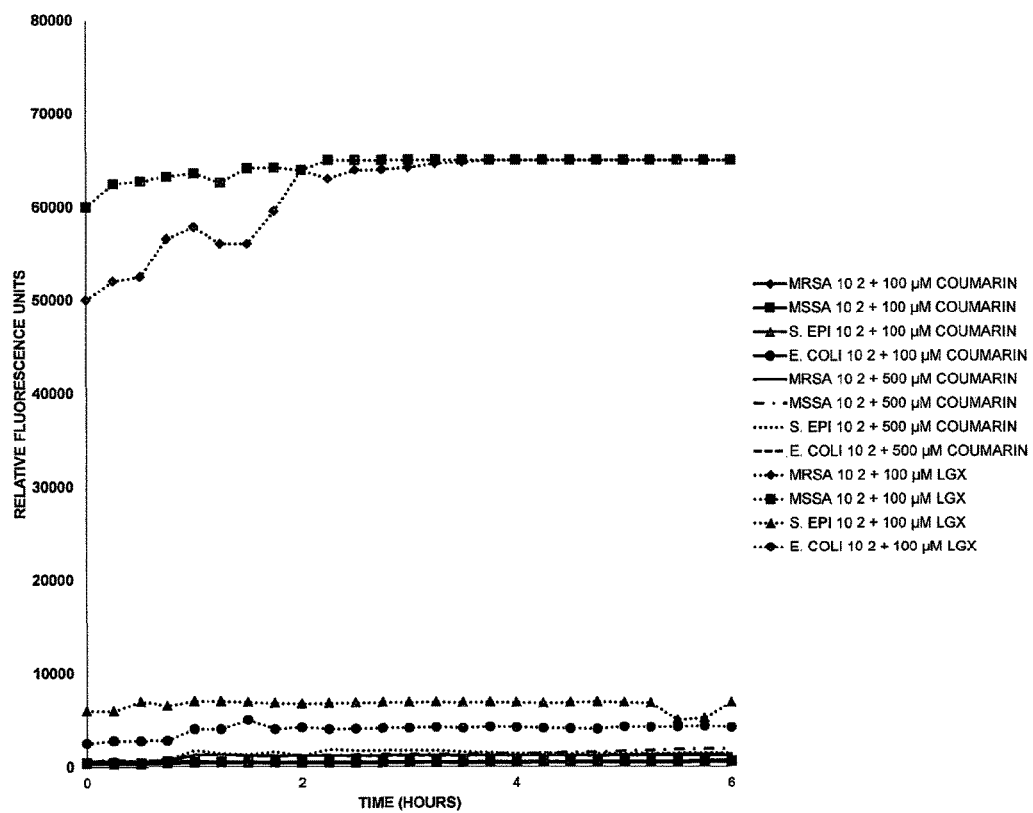
FIG. 12 shows a direct comparison between 100 μM and 500 μM N-t-BOC-val-pro-arg-7-amido-4-methylcoumarin on staphylocoagulase mediated fluorescence in varying bacterial species and 100 μM LGX on staphylocoagulase mediated fluorescence in varying bacterial species.

FIG. 12 demonstrates the comparison between 100 and 500 µm N-t-BOC-val-pro-arg-7-amido-4-methylcoumarin and 100 µm LGX in MRSA, MSSA, *E. coli* and *S. Epidermidis* at a $10^2$ concentration, which would be considered to be a "normal" level of bacteria. It is vastly evident that in MRSA and MSSA samples at this concentration, there is no comparison between the LGX system and -t-BOC-val-pro-arg-7-amido-4-methylcoumarin- the use of LGX by far produces a superior response in terms of selectivity and speed at a lower concentration than that of the coumarin system.

The LGX system facilitates the production of an instantaneous and increased fluorescent response, even at very low bacterial concentrations, and bears the potential to determine the presence of MRSA and MSSA far more significantly than N-t-BOC-val-pro-arg-7-amido-4-methylcoumarin. The speed and selectivity of the LGX system, as demonstrated in these data, shows that this new system may prove to be a vital tool in the detection of coagulase positive bacteria, more so than the systems which are already in place.

The first generation synthesis of the prototype active molecule (LGX) has been accomplished utilising liquid phase peptide synthesis, taking advantage of the highly reactive coupling reagents Oxyma, COMU® and EDCI. Firstly, the rhodamine is coupled to a suitably protected arginine residue (Boc-(Z)$_2$-Arg) utilising EDCI and Oxyma in pyridine/DMF. The two Boc protecting groups are them removed using TFA, before the Rhod(Arg(Z)$_2$NH$_2$)$_2$ is further coupled to the boo protected peptide dimer (Boc-Val-Pro). Finally deprotection under hydrogenation conditions remove the Cbz protecting groups yielding LGX.

Clinical isolates of Methicillin Resistant *Staphylococcus Aureus* (MRSA), Methicillin Sensitive *Staphylococcus Aureus* (MSSA), *Staphylococcus Epidermidis*, *Eschericia coli* and other staphyloccal species were cultured on nutrient agar prior to being grown overnight in nutrient broth under shaking conditions at 37° C. Each sample was rinsed liberally in sterile 1×PBS and varying concentrations of bacterial suspension from $10^{20}$-$10^6$ were generated by serial dilution in 1×PBS. Additionally, bacterial cultures were furthermore maintained on nutrient agar to assess the coagulase status of the isolate.

To determine the effects of varying bacterial concentrations with respect to bacterial strains and LGX concentrations on staphylocoagulase activity, 100 and 50 µM solutions of LGX were prepared in 1×PBS with the addition of 0.05 M Tris Buffer and 0.1 M NaCl to maintain a pH of 8.5 using LGX dissolved in MeOH so that final concentration of methanol was no more than 2.5%. Furthermore, an appropriate concentration (100 µM and 50 µM, respectively) of human prothrombin was added to the solution. 90 µl of LGX solution in addition to each respective bacterial isolate at varying concentrations was added to a microtitre plate. Staphylocoagulase activity resulting from cleavage of amide bonds within the compound was determined using fluorescence spectrophotometry exhibiting excitation at 488 nm and emission at 525 nm at 15 minute intervals over a 6 hour time period. n=3 cultures were assayed in each case. The plate reader used was a Fluostar Optima, and the plates used were Nunclon Surface 96 well plates.

Tests were also run to validate that the methanol had no adverse effects on the growth of a number of bacterial strains up to a ~5% methanol solution. Varying concentrations of methanol (0.25%, 0.5%, 1%, 2.5 5, 4% and 5%) were incubated with each bacterial species also at varying concentrations ($10^2$-$10^6$) for 2 hours prior to plating on nutrient agar to assess the effects of the solvent on bacterial viability. Plates were incubated overnight at 37° C. and the number of colonies was counted and it was found that up to 4% methanol, bacterial viability was not compromised at all bacteria concentrations, thus providing the optimum concentration to both maintain compound solubility and ensure bacterial cell viability to be 2.5%.

To compare the efficacy of this staphylocoagulase assay with current, well established "gold standard" methods of coagulase detection such as a coumarin assay, coagulase test and latex agglutination test, bacterial isolates were prepared in suspension as above and clinical isolates of each respective strain was cultured overnight on nutrient agar. 90 µl of bacterial suspension was added to a solution consisting of 100 µM solutions of N-t-BOC-val-pro-arg-7-amido-4-methylcoumarin prepared in 1×PBS with the addition of 0.05 M Tris Buffer and 0.1 M NaCl to maintain a pH of 8.5. Staphylocoagulase activity was determined by measuring the absorbance at 385 nm at 15 minute intervals over a 6 hour time period. It should be noted that a concentration of 795 µM of the coumarin dye is usually required post-culture ($10^6$-$10^8$ bacteria) in order to observe a significant chromogenic response.

Furthermore, to determine the positive/negative/false positive status of coagulase present in bacterial isolates, loopfuls of each respective culture was assessed using a staphylase text kit (Oxoid), under manufacturer's instructions. This particular kit is commonly used in hospital and research laboratories and functions through coagulase mediated clumping of fibrinogen-sensitised ovine blood cells. As opposed to being a colourometric or fluorometric assay, the staphylase kit provides an instant visible coagulation of the reagents following exposure to bacteria following a 24 hour culture. n=3 cultures were assayed in each case.

Figure 13:
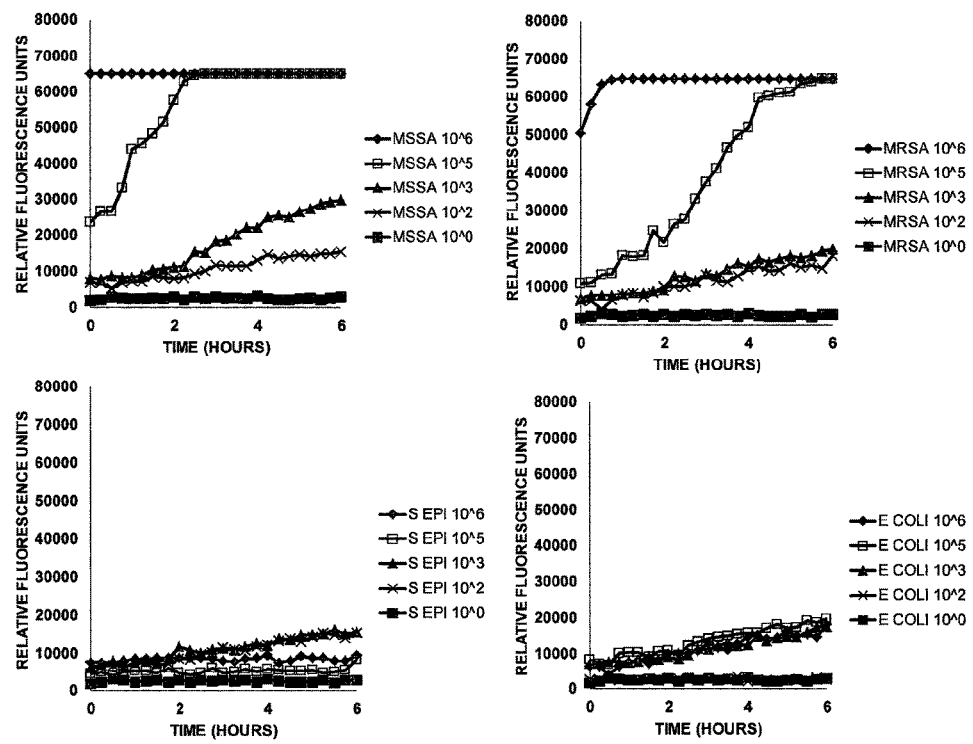
FIG. 13 shows high bacterial concentrations of MRSA, MSSA, *S. epidermidis* and *E. coli* with 50 μM LGX.

FIG. 13 demonstrates the effect of the presence of high concentrations of MRSA, MSSA, S. epidermidis and E. coli on the fluorescence potential of 50 µM LGX following staphylocoagulase mediated cleavage of amide bonds within the compound. It is evident from these results that at high bacterial concentrations of MRSA and MSSA ($10^6$), there was an almost instantaneous reaction, with fluorescence reaching the maximum reading of 65,000 RFU for each sample. However, at a lower concentration ($10^5$) of both MRSA and MSSA, a more gradual increase in fluorescence was observed, with fluorescence reaching a maximum after approximately 3 hours. Further to this, at both high and low concentrations of S. epidermidis and E. coli, no increase in fluorescence was observed and results remained consistently low for both bacterial species over the 6 hour time period.

Figure 14:
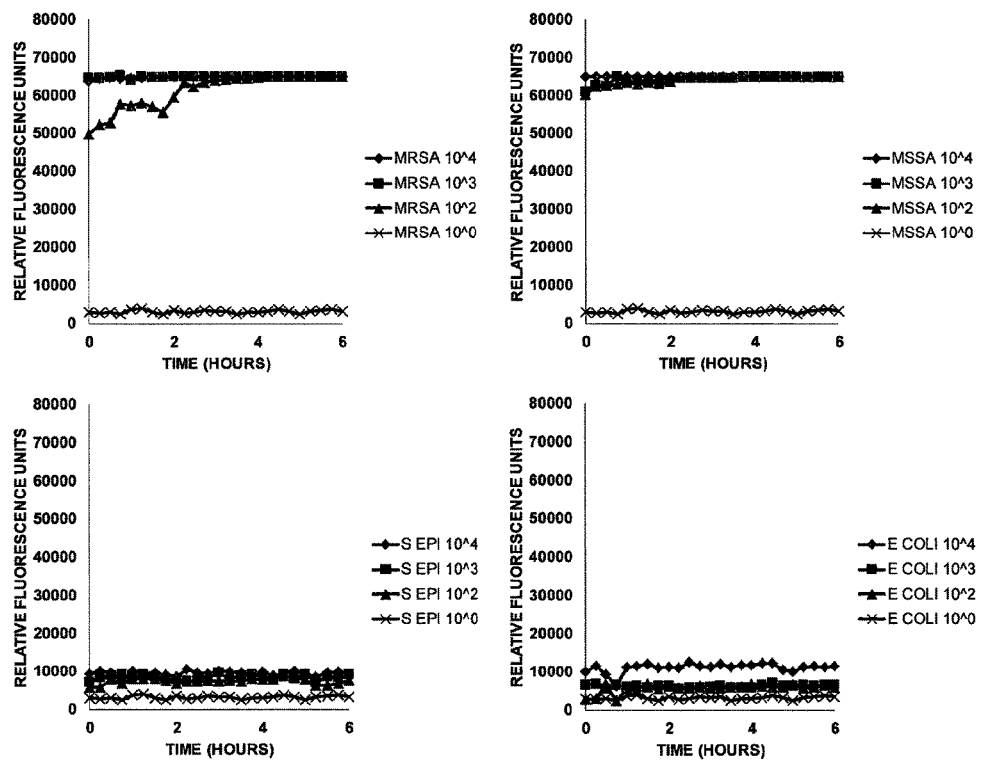
FIG. 14 shows low bacterial concentrations of MRSA, MSSA, *S. epidermidis* and *E. coli* with 100 μM LGX.

FIG. 14 demonstrates the effect of the presence of lower concentrations of MRSA, MSSA, S. epidermidis and E. coli on the fluorescence potential of 100 µM LGX following staphylocoagulase mediated cleavage of amide bonds within the compound. Again, it can be seen that at high bacterial concentrations of MRSA and MSSA ($10^4$ and $10^3$), and $10^2$ concentrations of MSSA, there was an almost instantaneous reaction, with fluorescence reaching the maximum reading of 65,000 RFU for each sample. However, at a lower concentration ($10^2$) of MRSA, a more gradual increase in fluorescence was observed, with fluorescence reaching a maximum after approximately 3 hours. Consistent with the data presented in FIG. 1.1, at both high and low concentrations of S. epidermidis and E. coli, no increase in fluorescence was observed and results remained consistently low for both bacterial species over the 6 hour time period.

Figure 15:
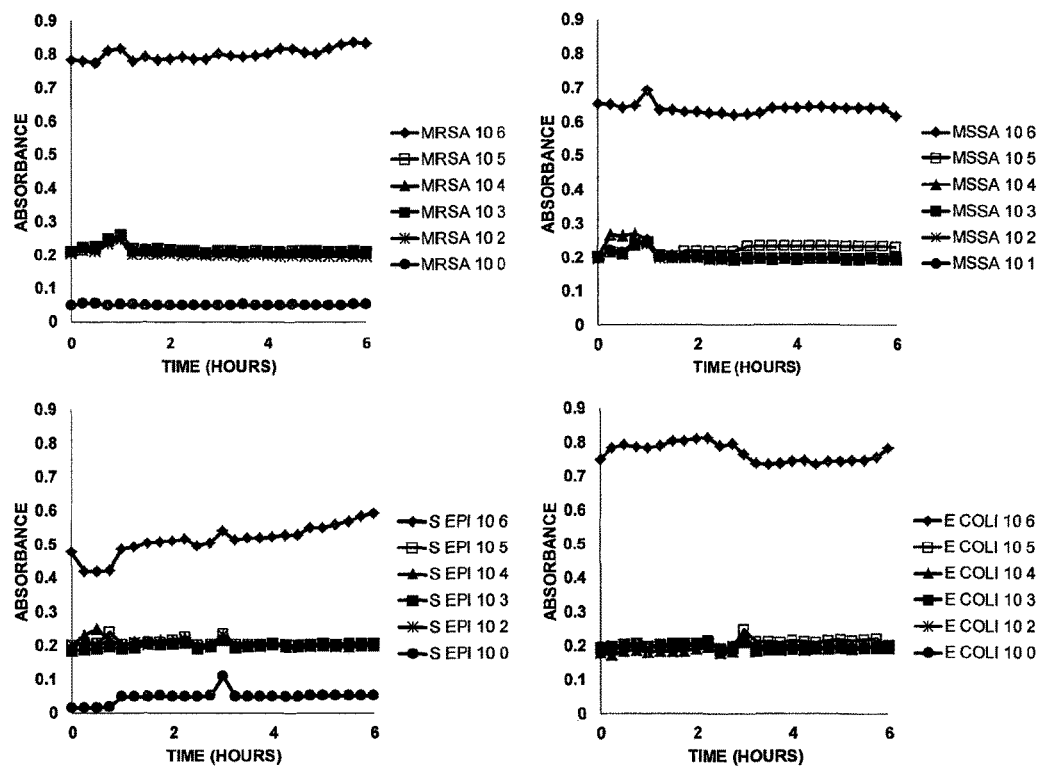
FIG. 15 shows varying bacterial concentrations of MRSA, MSSA, *S. epidermidis* and *E. coli* with 100 μM coumarin.

FIG. 15 details the efficacy of 100 µM N-t-BOC-val-pro-arg-7-amido-4-methylcoumarin as a means of detecting staphylocoagulase and in maintaining a distinct pattern of detection between both MRSA and MSSA, and S. epidermidis and E. coli. As can be observed there is a higher absorbance pattern observed at $10^6$ concentrations of all bacterial types, however, there is little increase over the 6 hour time period. Further to this, at $10^5$, $10^4$, $10^3$ and $10^2$ concentrations, there is no increase or variance between bacterial strains over the 6 hour time period, and absorbance remains consistent for all samples.

Table 1 displays the results of the staphylase test compared to the LGX system, which is based on the agglutination potential of bacterial species and strains, for MRSA, MSSA, E. epidermidis, Encolpia and other known coagulase negative strains of bacteria including S. hominus, S. warneri and M. luteus. The kit used has the ability to distinguish between the presence of coagulase positive and negative bacterial strains, in addition to determining whether a sample is proving to be a false positive. As demonstrated by the table, MRSA and MSSA are both coagulase positive bacteria, as furthermore confirmed by our LGX system and the staphylase test, S. epidermidis, E. coli, S. warneri, S. hominus and M. Luteus are all proven to be coagulate negative, and both LGX and staphylase test showed E. coli and S. epidermidis, S. warneri and S. hominus tested negative for coagulase activity. However, M. luteus provided a false positive result using the staphylase test, but showed to be negative using the LGX system.

TABLE 1

LGX vs Staphylase test data for the detection of coagulase positive samples

| BACTERIAL SPECIES | COAGULASE +/− | LGX SYSTEM | STAPHYLASE TEST |
|---|---|---|---|
| MRSA | + | + | + |
| MSSA | + | + | + |
| S. EPIDERMIDIS | − | − | − |
| E. COLI | − | − | − |
| S. WARNERI | − | − | − |
| S. HOMINUS | − | − | − |
| M. LUTEUS | − | − | False positive |

Based on these data, it is evident that the system according to the present invention is superior to what is already in place for rapidly detect the presence of staphylocoagulase within a bacterial sample, which is relative to the amount of bacteria within a culture.

Using the LGX system an immediate and significant fluorescent response in the presence of only $10^2$ Staphylococcus aureus units at 525 nm (ex 488 nm) is observed. This outperforms the N-t-BOC-val-pro-arg-7-amido-4-methylcoumarin in terms of sensitivity by several orders of magnitude ($10^4$ bacteria).

The LGX system also offers good selectivity for coagulase positive bacteria and quickly discriminates for SA against E. coli and S. epidermidis and other common bacteria, which are shown to give negligible results when tested with N-t-BOC-val-pro-arg-7-amido-4-methylcoumarin at the low bacterial concentrations at which the LGX system shows a clear response. Culturing of SA is essential for its detection using the staphylase test and N-t-BOC-val-pro-arg-7-amido-4-methylcoumarin. The present invention can detect SA at very low bacterial concentrations and can be used at the point of care as a rapid diagnostic tool for the screening of people, materials and surfaces for SA prior to typing of the strain and/or further discriminatory microanalysis.

Furthermore, the use of this method of detection has shown to overrule the provision of false positives within a sample. The rapid detection and the potential applications of this compound as a culture independent means to determine the presence of MRSA and MSSA, will provide a vital tool in diagnosing this infection and may lead to faster and more specific treatment of disease, thus demonstrating that this system has significant diagnostic potential, from both a research and clinical perspective.

Efficacy of a Compound and a Method of the Current Invention, in Combination with Prothrombin or Prethrombin, to Detect S. aureus in Patient Samples This set of experiments was undertaken to assess the efficacy of a method of the current invention in combination with either prothrombin or prethrombin using patient samples. The results were verified using gram staining, cell culturing methods and the staphylase test kit (oxoid).

A population of 113 volunteers were administered a "set" of swabs, comprising two swabs that were pre-moistened with sterile H$_2$O, and one swab that was dry. Each volunteer swabbed the internal periphery of each nostril with the two moistened swabs. Each volunteer then subsequently swabbed the internal periphery of each nostril with the dry swab. The swabs were then placed into amies transport medium to maintain bacterial cell viability. Each sample was anonymous and the study was randomised.

A 100 µL solution of 100 µM LGX with either 1×prothrombin or 1×prethrombin (buffered to pH 8.5 with Tris base and NaCl), was pipetted into sterile 1.5 mL eppendorf tubes. Each moistened swab was placed into the eppendorf tube, and cut to a length to facilitate closure of the tube, with a pair of sterilised scissors. Each tube was subjected to vigorous agitation and the swab tips were removed with sterile forceps. The remaining solution was subsequently pipetted into a microtitre plate (Nunclon 96 well plates). The relative fluorescence of the sample was then recorded every fifteen minutes over a six hour time period ($\lambda$ex.=488 nm and $\lambda$em=525 nm).

In tandem with this, the remaining swabs (in amies transport medium) were transferred onto pre warmed mannitol salt agar (chromogenic agar for the determination of S. aureus) plates and incubated for up to 48 hours at 37° C. The colour change and colony appearance of the bacteria was noted. A colour change from red to yellow demonstrates the presence of S. aureus, due to fermentation of the mannitol, causing a change in pH. Following this, 20 separate, discrete colonies were sub-cultured onto nutrient agar and also onto Baird Parker Agar (agar for the determination of S. aureus and S. epidermidis). After an overnight culture at 37° C., colony morphology and appearance was observed (S. aureus colonies are large with a pale "halo" surrounding the colonies, S. epidermidis colonies are small and black).

Additionally, isolates from the nasal swabs cultured on nutrient agar were tested for coagulase activity using a staphylase test kit (oxoid). Loopfuls of bacteria were assayed based on coagulase mediated clumping of fibrinogen-sensitised ovine blood cells. A coagulase positive bacteria is indicative of S. aureus, and as little as 1 positive isolate is subsequently deemed a S. aureus carrier.

A final test to determine the identification of the bacteria within each sample, a gram stain was performed. This is based on the presence of peptidoglycan in gram positive cells and their ability to retain crystal violet. S. aureus is a gram positive bacterium. Briefly, a drop of sterile dH$_2$O was placed on a microscope slide and a small amount of culture was applied to this and allowed to air dry. The slide was passed though a flame to fix the bacteria. Crystal Violet was applied to each slide, followed by washing with dH$_2$O. Iodine was then added to the slides, followed by washing with dH$_2$O and subsequent decolourisation with ethanol and another wash with dH2O. Each slide was counterstained with carbol fushchin (for gram negative), rinsed again and allowed to dry. Each slide was observed for gram positive bacteria using 40×magnification using a light microscope.

Results

Each swab sample was examined for the presence of S. aureus based on the above identification techniques, and termed "positive" or "negative". The results were compared to the finding of the assay of the current invention (LGX test), with either prethrombin or prothrombin, and plotted on a bar chart as a function of relative fluorescence units.

FIGS. 16A to 16C illustrate the results using 100 µM LGX with 1×prothrombin at 15, 30, and 60 minutes. The lower threshold limit for relative fluorescence units of 20,000 RFU was used to determine if a sample was "positive" or "negative" for S. aureus using the method of the invention. This threshold was based on previous data using clinical strains at a concentration of $10^2$ colony forming units per ml (CFU/mL$^{-1}$). As can be seen from FIGS. 16A and 16C approximately 29 samples tested positive for S. aureus using a method of the current invention after 15 minutes and approximately 34 samples tested positive for S. aureus after 60 minutes using a method of the current invention. As illustrated in FIG. 16C a number of samples tested negative for S. aureus using an assay of the present invention, which tested positive for S. aureus (by demonstrating a prevalence of ≤5% coagulase+bacteria) using other identification techniques. It is considered that this "false negative" result was due to the colony numbers being insufficient to yield a positive results with the method of the current invention. Overall, the use of prothrombin in the assay of the current invention was efficient in detecting S. aureus in as little as 15 minutes.

FIGS. 17A to 17C illustrate the results using 100 µM LGX with 1×prethrombin at 15, 30, 60 and 120 minutes. The lower threshold limit for relative fluorescence units of 20,000 RFU was used to determine if a sample was "positive" or "negative" for S. aureus. This threshold was based on previous data using clinical strains at a concentration of $10^2$ colony forming units per ml (CFU/mL$^{-1}$). As can be seen from FIGS. 17A and 17C approximately 49 samples tested positive for S. aureus after 15 minutes using a method of the current invention and approximately 49 samples tested positive for S. aureus after 60 minutes using a method of the current invention. As illustrated in FIG. 17C a number of samples tested negative for S. aureus using an assay of the present invention, which tested positive for S. aureus (by demonstrating a prevalence of 5% coagulase bacteria) using other identification techniques. It is considered that this "false negative" result was due to the colony numbers being insufficient to yield a positive results with the method of the current invention. Overall, the use of prethrombin in the assay of the current invention was efficient in detecting S. aureus in as little as 15 minutes.

Conclusion

Figure 17:
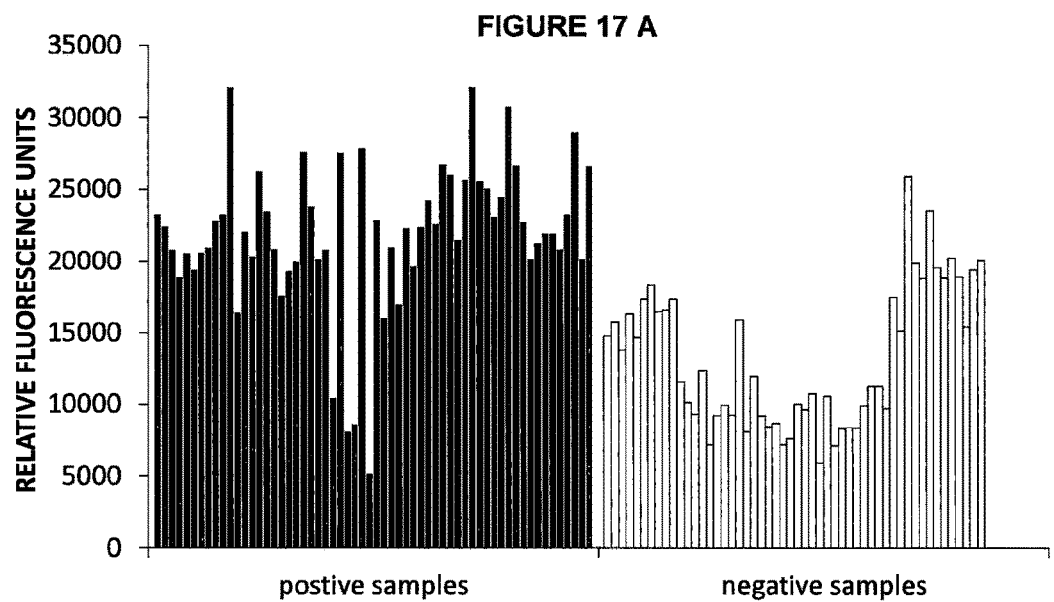
FIG. 17A shows the detection of *S. aureus* in samples by standard techniques and the relative fluorescence of the samples with 100 μM LGX with 1×prethrombin at 15 minutes.
FIG. 17B shows the detection of *S. aureus* in samples by standard techniques and the relative fluorescence of the samples with 100 μM LGX with 1×prethrombin at 30 minutes.
FIG. 17C shows the detection of *S. aureus* in samples by standard techniques and the relative fluorescence of the samples with 100 μM LGX with 1×prethrombin at 60 minutes.
Figure 17:
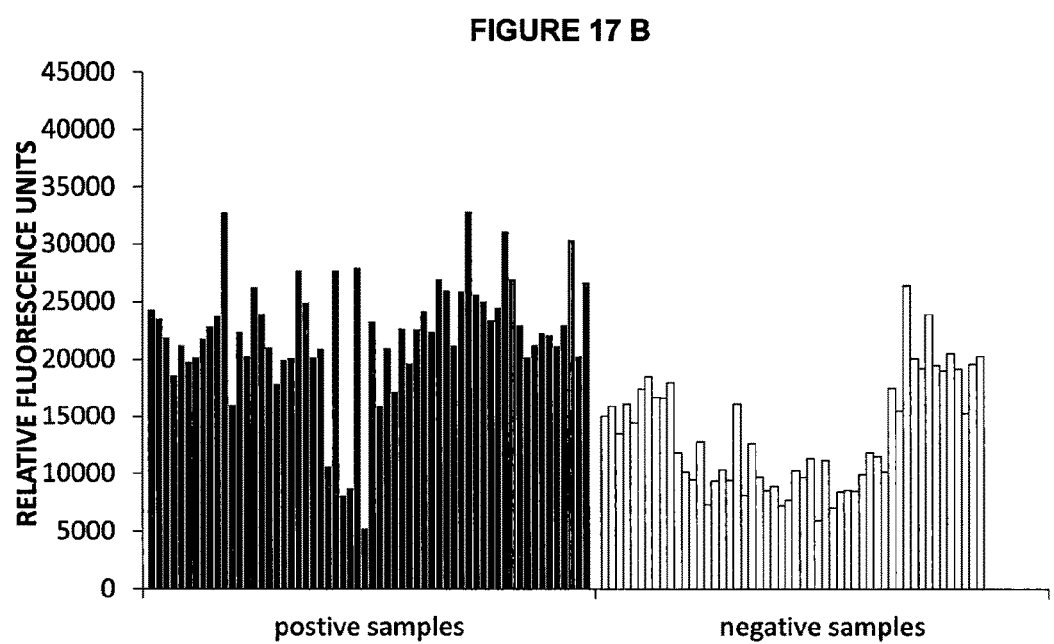
Figure 18:
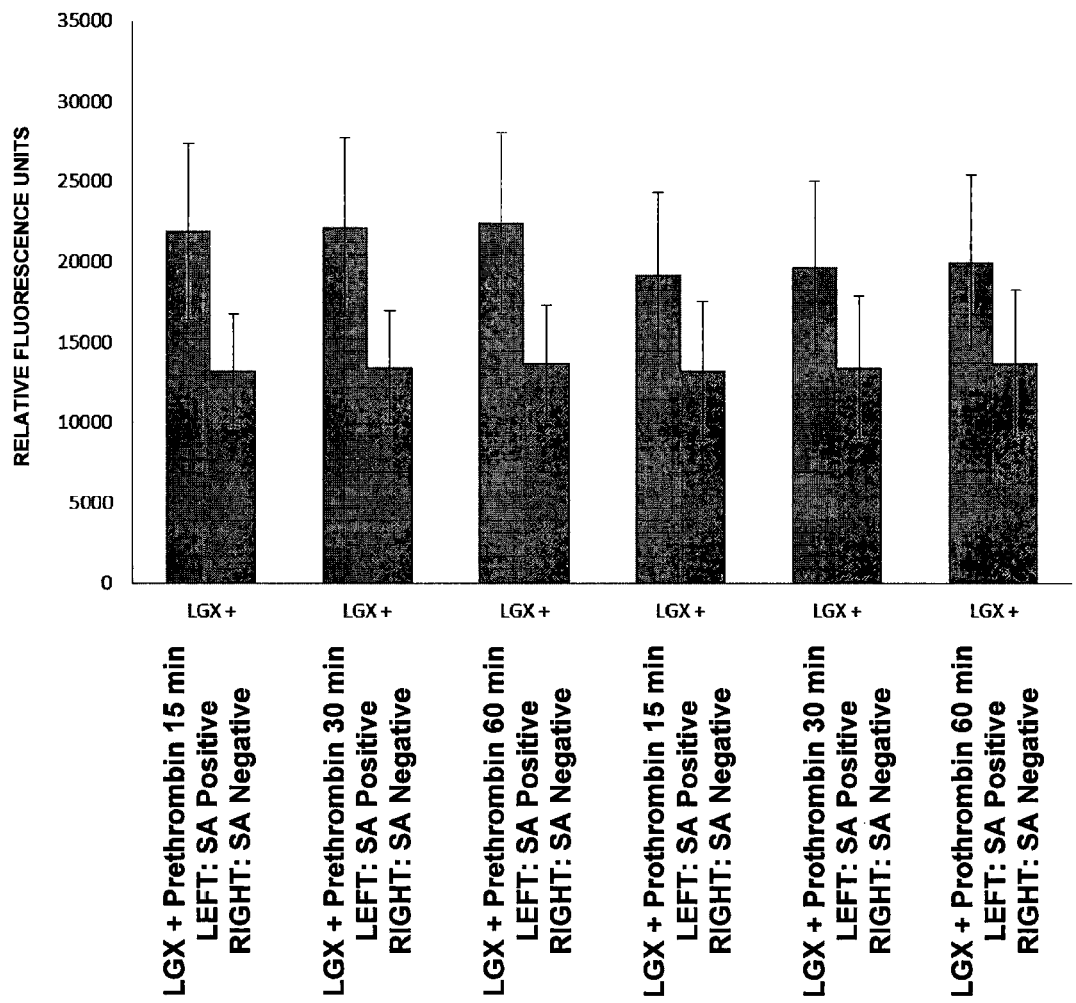
FIG. 18 shows the mean values for *S. aureus* positive and *S. aureus* negative samples

As can be observed from FIGS. 16 and 17, using prethrombin in the assay of the invention provided higher sensitivity and specificity than the use of prothrombin, i.e. there were more true positive results and less "false positive" and "false negative" results. It is considered that this result is due to the fact that prothrombin is not metabolised as quickly as prethrombin and therefore does not demonstrate as potent specificity in terms of detection of coagulase positive bacteria. This is further illustrated by FIG. 18 which shows the mean values for S. aureus positive and S. aureus negative samples at each time interval using the method of the invention with prothrombin and prethrombin.

Synthetic Experimental

Boc-NH-Val-Pro-OMe

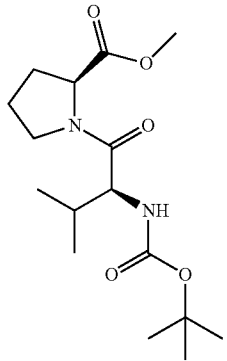 [SMILES: COC(=O)[C@@H]1CCCN1C(=O)[C@@H](NC(=O)OC(C)(C)C)C(C)C]

To a solution of NH-Pro-OMe (3.00 mmol, 0.50 g, 1 eq) and Boc-NH-Val-OH (3.00 mmol, 0.65 g, 1 eq) in anhydrous DMF (6 mL) was added NEt$_3$ (9.00 mmol, 0.91 g, 1.25 ml, 3 eq) and the solution was cooled to 0° C. COMU (3.00 mmol, 1.28 g, 1 eq) was then added to the reaction mixture and stirred for 1 hr at 0° C. before warming to ambient temperature over 4 hrs. The reaction was then diluted with EtOAc (12 mL), washed with saturated aqueous NaHCO$_3$ (2×4 mL), 1M aqueous LiCl (2×4 mL) then dried over NaSO$_4$ and concentrated to give product as a light brown oil which was used without further purification (2.07 mmol, 0.68 g, 69%).

Rho-(Arg-(Z)$_2$-NHBoc)$_2$

To a solution of HO-arg(Z)$_2$NHBoc (4.61 mmol, 2.5 g, 6 eq), EDCI (4.61 mmol, 883 mg, 6 eq), oxyma (4.60 mmol, 654 mg, 6 eq) in anhydrous DMF (5 mL) was added freshly distilled anhydrous pyridine (5 mL) followed by rhodamine 110 (0.763 mmol, 280 mg, 1 eq) and the solution was stirred at room temperature under a nitrogen atmosphere for 10 days. The reaction was then diluted with EtOAc (20 mL), washed with saturated aqueous NaHCO$_3$ (2×10 mL), 1M aqueous LiCl (2×10 mL) and 10% aqueous CuSO$_4$ (3×10 mL), dried over MgSO$_4$ and concentrated to give a green oily solid. This crude product was then purified by column chromatography over silica gel, eluting with 25% EtOAc in CHCl$_3$ to yield the product as a white amorphous solid (0.14 mmol, 200 mg, 18%): $\delta_H$(400 MHz, CDCl$_3$), 9.45 (2H, s, broad, NH-23), 9.29 (2H, s, Broad, NH-21), 9.01 (2H, s, broad, NH-15), 8.02 (1H, dd, $^3J_{HH}$=6.02 Hz, $^4J_{HH}$=2.01 Hz, CH-12), 7.56-7.69 (2H, m, CH-10 and CH-11), 7.43, (2H, s, CH-2), 7.38-7.20 (20H, m, CH-27, CH-28, CH-29, CH-33, CH-34 and CH-35), 7.05 (1H, dd, $^3J_{HH}$=6.02 Hz, $^4J_{HH}$=2.01 Hz, CH-9), 6.77 (2H, d, $^3J_{HH}$=6.02 Hz, CH-4), 6.69 (2H, dd, $^3J_{HH}$=6.02 Hz, CH-5), 5.70, (2H, s, broad, NH-36), 5.30-5.02 (8H, m, CH$_2$-25 and CH$_2$-31), 4.39, (2H, m, CH-17) 4.07-3.87 (4H, m, CH$_2$-20), 1.86-1.62 (8H, m, CH$_2$-18 and CH$_2$-19), 1.41 (18H, s, CH$_3$-39); $\delta_c$ (100 MHz) 171.1, 171.0, 169.5, 163.6, 160.8, 156.2, 155.7, 153.1, 139.6, 136.4, 135.1, 134.4, 134.4, 129.7, 128.9, 128.8, 128.5, 128.4, 128.3, 128.0, 128.0, 126.2, 124.9, 124.1, 115.4, 114.2, 107.9, 82.4, 80.4, 69.1, 67.2, 54.8, 44.0, 28.5, 28.3, 25.01.

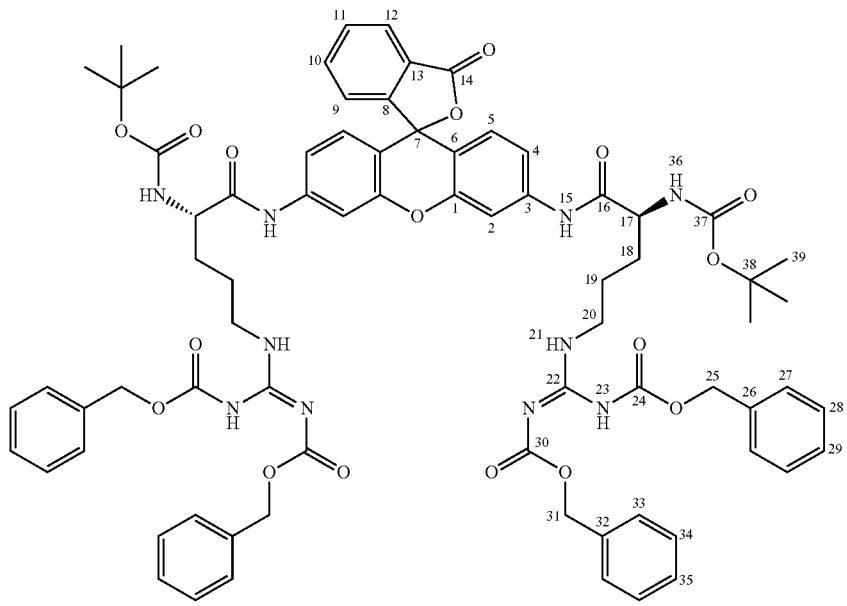 [SMILES: CC(C)(C)OC(=O)N[C@@H](CCCN/C(=N/C(=O)OCc1ccccc1)NC(=O)OCc1ccccc1)C(=O)Nc1ccc2c(c1)Oc1cc(NC(=O)[C@H](CCCN/C(=N/C(=O)OCc3ccccc3)NC(=O)OCc3ccccc3)NC(=O)OC(C)(C)C)ccc1C21OC(=O)c2ccccc21]

Rho-(Arg-(Z)₂—NH₂)₂

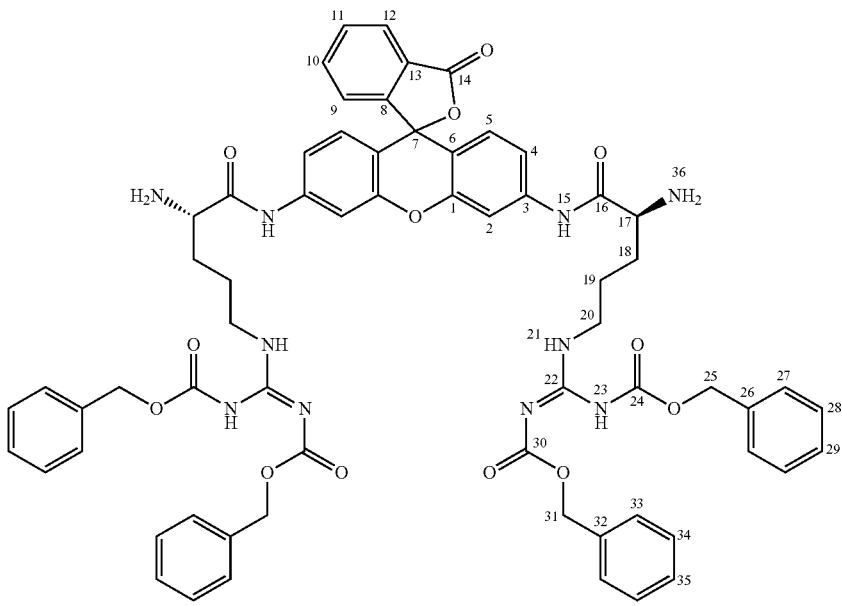 [SMILES: N[C@@H](CCCN/C(=N/C(=O)OCc1ccccc1)NC(=O)OCc1ccccc1)C(=O)Nc1ccc2c(c1)Oc1cc(NC(=O)[C@@H](N)CCCN/C(=N/C(=O)OCc3ccccc3)NC(=O)OCc3ccccc3)ccc1C21OC(=O)c2ccccc21]

To a solution of Rho-(Arg-(Z)₂-NHBoc)₂ (0.14 mmol, 200 mg, 1 eq) in DCM (2 mL) was added TFA (0.3 mL) and the reaction was stirred under nitrogen atmosphere for 6 hours. The reaction was then quenched with 1M aqueous NaOH (1 mL) and extracted. The organic layer was then washed with saturated aqueous NaCl (3×1 mL), dried over MgSO₄ and concentrated to yield product as an amorphous solid which used immediately (0.13 mmol, 156 mg, 94%).

Rho-(Arg-(Z)₂-Pro-Val-NHBoc)₂

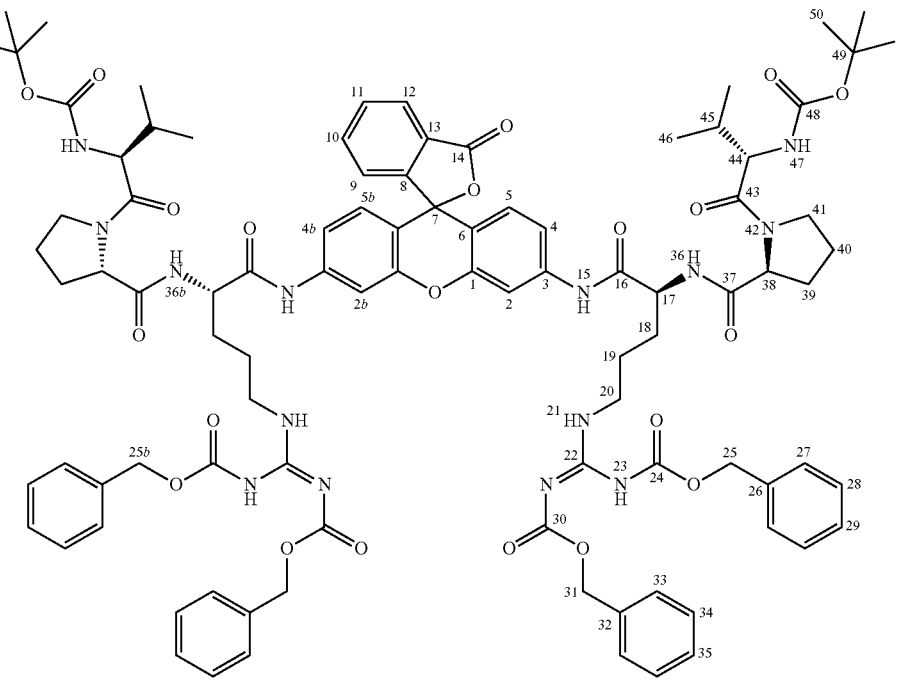

A solution of Rho-(Arg-(Z)₂—NH₂)₂ (0.132 mmol, 156 mg, 1 eq), HO-Pro-Val-NHBoc (0.264 mmol, 92 mg, 2 eq) and NEt₃ (0.396 mmol, 40 mg, 55 µL, 3 eq) in anhydrous DMF (1 mL) was cooled to 0° C. before the addition of COMU (0.264 mmol, 114 mg, 2 eq). The reaction was stirred under a nitrogen atmosphere for 1 hour at 0° C. before warming to room temperature over a further 3 hours. The reaction was then diluted with EtOAc (2 mL), washed with saturated aqueous NaHCO₃ (2×1 mL), 1M aqueous LiCl (3×1 mL) then dried over NaSO₄ and concentrated to give crude product. Product was purified by preparative HPLC to yield the pure product as a colourless glassy solid (0.0182 mmol, 32 mg, 14%): $\delta_H$(600 MHz; CDCl₃) 9.42 (2H, m, NH-23), 8.83, (2H, s, NH-21), 8.05 (1H, d, $^3J_{HH}$=7.6, CH-12), 7.77 (1H, s, CH-2b), 7.70-7.61 (3H, m, CH-2, CH-10 and CH-11), 7.57 (1H, s, NH-36), 7.51 (1H, s, NH-36b), 7.41-7.36 (10H, m, CH-27, CH-28 and CH-29), 7.34-7.30 (4H, m, CH-33), 7.26-7.20 (6H, m, CH-34 and CH-35), 7.10 (1H, d, $^3J_{HH}$=6.4, CH-9), 7.09 (1H, d, $^3J_{HH}$=8.4, CH-4), 7.03 (1H, d, $^3J_{HH}$=8.4, CH-4b), 6.69 (1H, d, $^3J_{HH}$=8.4, CH-5), 6.68 (1H, d, $^3J_{HH}$=8.4, CH-5b), 5.27 (4H, s, CH₂-31), 5.20 (2H, d, $^3J_{HH}$=12.0, CH₂-25), 5.16 (2H, d, $^3J_{HH}$=8.6, NH-47), 5.06 (2H, d, $^3J_{HH}$=12.0, CH₂-25b), 4.53 (2H, m, CH-17), 4.34 (2H, m, CH-38), 4.25 (2H, m, CH-44), 4.07 (4H, m, CH₂-20), 3.73 (2H, m, CHH-41), 3.58 (2H, m, CHH-41), 2.07-1.66 (18H, m, CH₂-18, CH₂-19, CH₂-39, CH₂-40, CH-45), 1.47 (18H, s, CH₃-50), 0.97-0.84 (12H, m, CH₃-46); $\delta_c$ (125 MHz; CDCl₃) 172.0, 170.0, 163.5, 161.1, 155.9, 151.6, 140.0, 136.2, 135.0, 134.5, 129.7, 128.9, 128.9, 128.5, 128.5, 128.4, 128.3, 128.2, 128.1, 126.3, 125.1, 123.9, 114.2, 108.2, 82.6, 79.7, 69.2, 67.2, 60.5, 60.3, 57.3, 57.2, 54.0, 47.7, 44.0, 31.3, 29.7, 28.4, 25.2, 25.0, 19.4, 17.5, 17.5, 14.2.

Rho-(Arg-Pro-Val-NHBoc)₂

To a solution of Rho-(Arg-(Z)₂-Pro-Val-NHBoc)₂ (0.0182 mmol, 32 mg, 1 eq) in anhydrous DMF (0.5 mL) and anhydrous MeOH (0.5 mL) was added 5% Pd/C (1 mg) and the mixture was stirred under a hydrogen atmosphere for 48 hours. The reaction mixture was then concentrated, dissolved in methanol and filtered through celite. Concentration yielded the product as an amorphous white solid (0.0140 mmol, 22 mg, 77%): $\delta_H$(600 MHz; CD₃OD) 10.11 (2H, d, $^3J_{HH}$=7.7, NH-24), 8.48 (2H, d, $^3J_{HH}$=7.0, NH-25), 8.17 (2H, s, NH-15), 8.05 (1H, d, $^3J_{HH}$=7.6, CH-12), 7.89 (1H, s, CH-2b), 7.82 (1H, s, CH-2), 7.79 (1H, dd, $^3J_{HH}$=8.5, $^4J_{HH}$=6.9, CH-11) 7.73 (1H, dd, $^3J_{HH}$=8.5, $^4J_{HH}$=6.9, CH-10), 7.41 (2H, s, NH-21), 7.22 (1H, d, $^3J_{HH}$=7.8, CH-4), 7.21 (1H, d, $^3J_{HH}$=7.8, CH-9), 7.19 (1H, d, $^3J_{HH}$=7.8, CH-4b), 6.75 (2H, d, $^3J_{HH}$=7.8, CH-5), 6.75 (2H, d, $^3J_{HH}$=7.8, CH-5b), 6.65 (2H, $^3J_{HH}$=7.8, NH-35), 4.52-4.96 (4H, m, CH-17 and CH-27), 4.20 (2H, m, CH-32), 3.93 (2H, m, CHH-30), 3.70 (2H, m, CHH-30) 3.24 (4H, m, CH₂-20), 2.28 (4H, m, CH₂-18), 2.12 (2H, m, CHH-28), 2.04-1.96 (6H, m, CHH-28, CHH-29 and CH-33), 1.87 (2H, m, CHH-29) 1.45 (18H, s, CH₃-38) 1.01 (6H, m, CH$_a$-34) 0.96 (6H, m, CH₃-34); $\delta_c$(125 MHz; CD₃OD) 173.2, 172.2, 171.0, 169.8, 163.8, 157.4, 156.7, 151.5, 140.7, 135.4, 130.0, 128.0, 126.2, 124.6, 123.7, 115.6, 114.1, 107.4, 82.7, 79.2, 73.3, 60.4, 58.0, 53.7, 48.6, 48.3, 44.1, 40.7, 35.6, 30.2, 29.4, 29.2, 28.9, 27.3, 24.9, 24.7, 22.3, 18.4, 17.2. (3 additional peaks for C-2b, C-4b and C-5b); m/z (Cl) 618.3317 [M+2H]; HRMS: Found 618.3322 (z=2) [M+2H], C₆₂H₈₆N₁₄O₁₃ [M] requires 1235.4322 (z=1), 617.7161 (z=2).

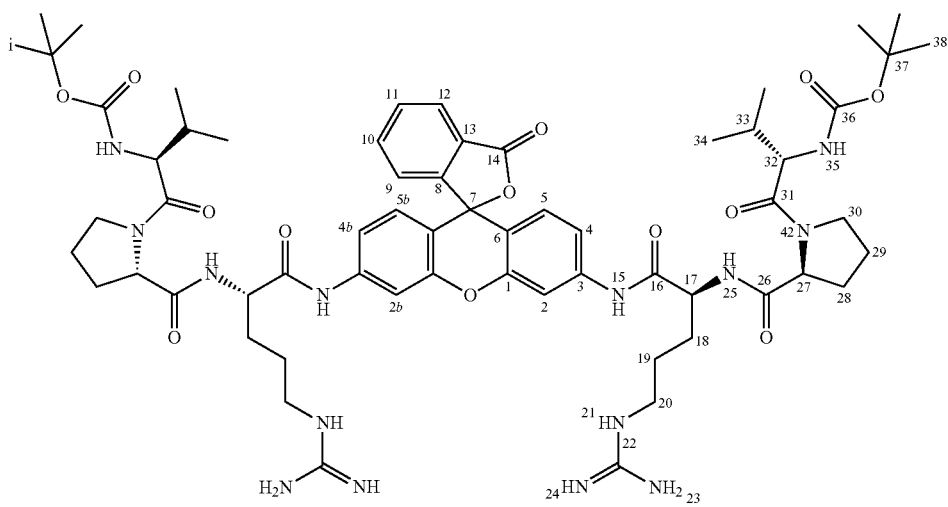

An Optional Synthetic Route for the Compounds of Embodiment 2
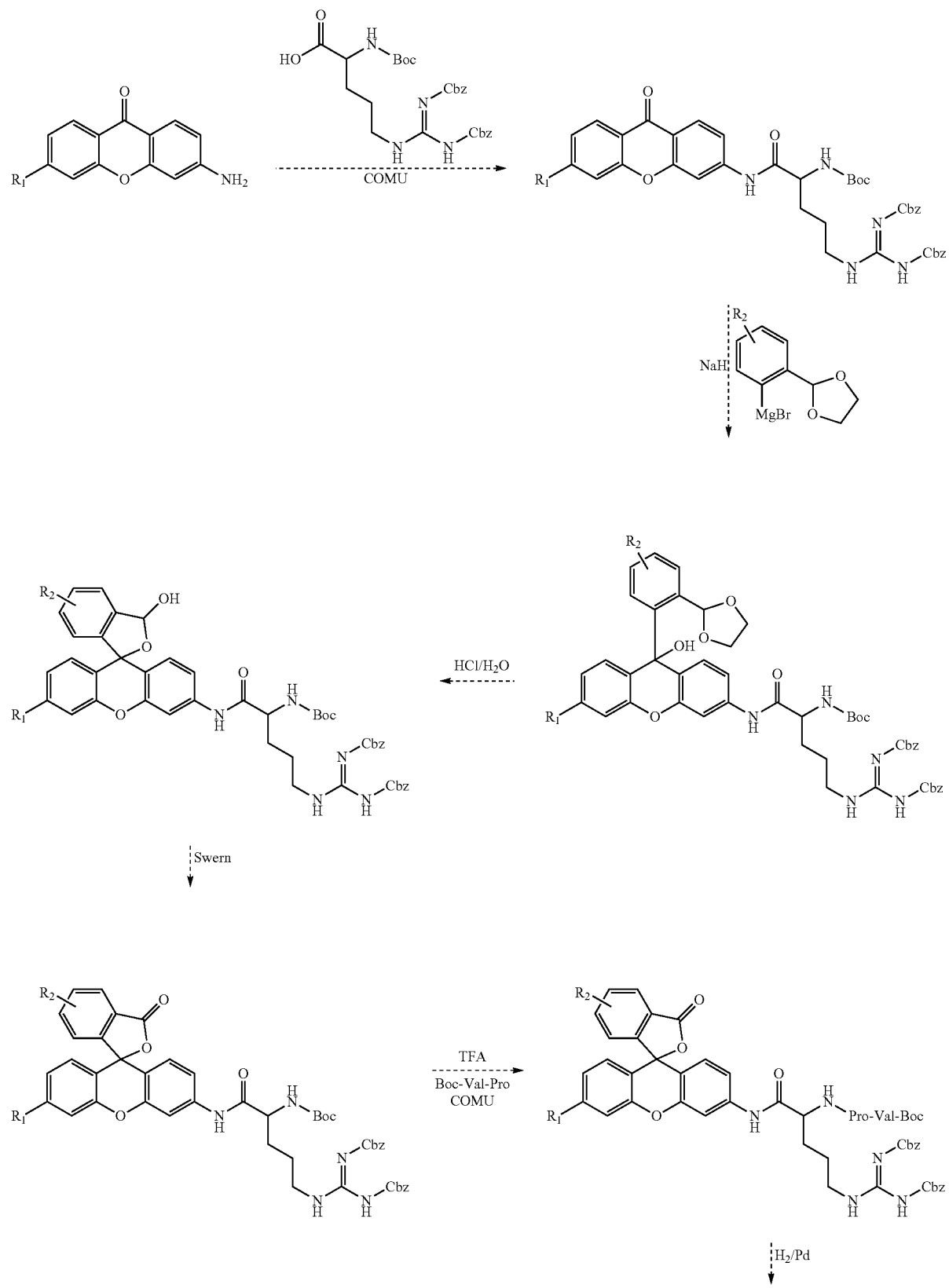

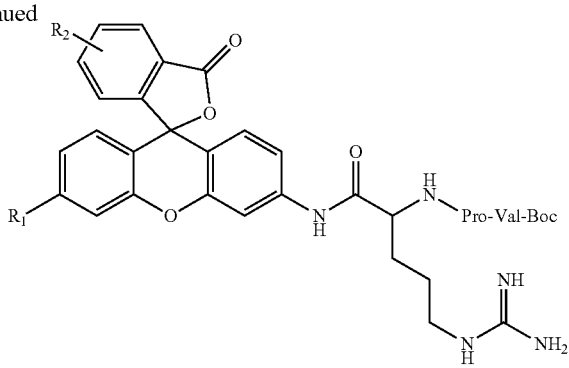

R₁ = H, NO₂, OMe
R₂ = H, NO₂, OMe

Relevant References for Start Material Synthesis

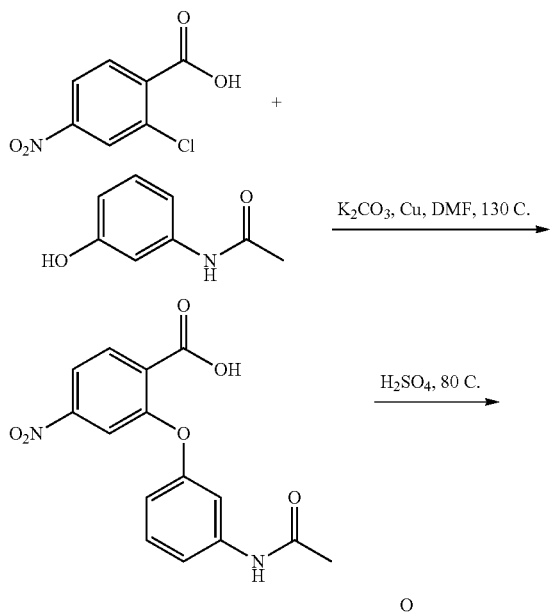

J. Am. Chem. Soc. 2007, 129, 4510-4511

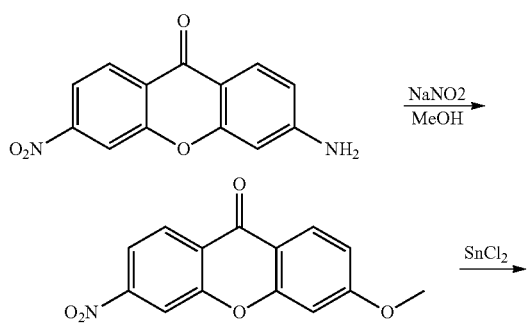

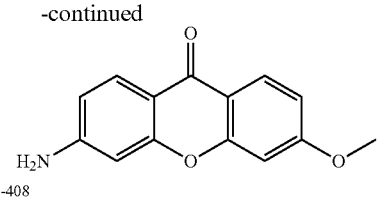

Org. Lett, 2009, 11 (2), pp 405-408

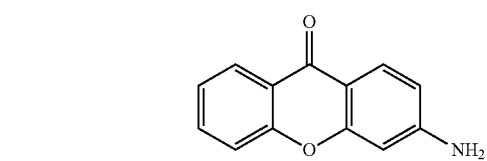

Journal of Medicinal Chemistry, 2000, 43, 1826-1840.

The invention claimed is:

1. A composition for use in detection of a coagulase-producing bacterial strain or strains, said composition comprising 50 µM to 100 µM of a compound of Formula II, 50 µM to 100 µM prothrombin or prethrombin or both, and a bacterial strain, wherein the bacterial strain is *Staphylococcus aureus*, methicillin-resistant *Staphylococcus aureus* (MRSA) or methicillin-susceptible *Staphylococcus aureus* (MSSA), or combinations thereof, and the bacteria is present in a concentration of $10^2$ to $10^6$, wherein the compound of Formula II has the structure:

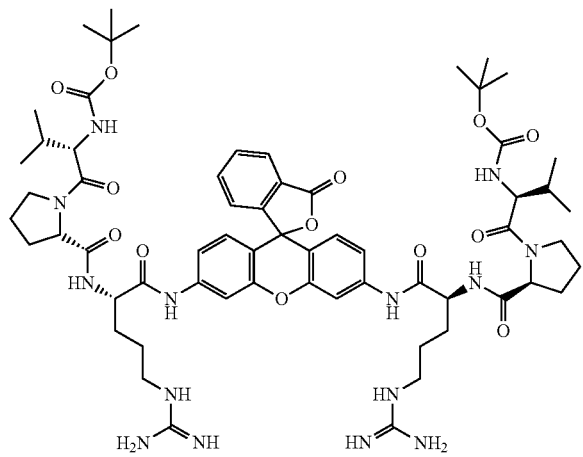

2. The composition of claim 1 wherein said composition comprises 50 μM to 100 μM prothrombin.

3. A method of detecting a coagulase-producing *Staphylococcus aureus* bacterial strain comprising: detecting an optical response in the composition of claim 1.

4. The method according to claim 3, wherein the composition comprises 50 μM to 100 μM prethrombin.

5. The method according to claim 3, wherein the optical response is fluorescence.

6. The method according to claim 3, wherein the bacterial strain is from a sample selected from the group consisting of a biological fluid, a tissue sample, a tissue section, a cell sample and a non-biological fluid or substrate.

7. The method according to claim 3, wherein the bacterial strain is from a human sample or an animal sample.

8. The method according to claim 3, wherein the bacterial strain is from a food sample.

* * * * *